United States Patent
Bell et al.

(10) Patent No.: US 11,198,687 B2
(45) Date of Patent: Dec. 14, 2021

(54) HETEROARYL ALLOSTERIC MODULATORS OF NICOTINIC ACETYLCHOLINE RECEPTORS

(71) Applicant: Merck Sharp & Dohme Corp., Rahway, NJ (US)

(72) Inventors: Ian M. Bell, Harleysville, PA (US); Brendan M. Crowley, Collegeville, PA (US); Peter J. Manley, Harleysville, PA (US); William D. Shipe, Chalfont, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/646,616

(22) PCT Filed: Sep. 14, 2018

(86) PCT No.: PCT/US2018/050975
§ 371 (c)(1),
(2) Date: Mar. 12, 2020

(87) PCT Pub. No.: WO2019/060210
PCT Pub. Date: Mar. 28, 2019

(65) Prior Publication Data
US 2020/0262826 A1    Aug. 20, 2020

Related U.S. Application Data

(60) Provisional application No. 62/560,444, filed on Sep. 19, 2017.

(51) Int. Cl.
| | |
|---|---|
| *C07D 413/08* | (2006.01) |
| *A61P 25/28* | (2006.01) |
| *A61P 25/18* | (2006.01) |
| *A61P 25/16* | (2006.01) |
| *C07D 413/14* | (2006.01) |
| *C07D 417/08* | (2006.01) |
| *C07D 417/14* | (2006.01) |
| *A61K 45/06* | (2006.01) |

(52) U.S. Cl.
CPC .......... *C07D 413/08* (2013.01); *A61P 25/16* (2018.01); *A61P 25/18* (2018.01); *A61P 25/28* (2018.01); *C07D 413/14* (2013.01); *C07D 417/08* (2013.01); *C07D 417/14* (2013.01); *A61K 45/06* (2013.01)

(58) Field of Classification Search
CPC ... C07D 413/08; C07D 413/14; C07D 417/08
See application file for complete search history.

(56) References Cited

U.S. PATENT DOCUMENTS

| 5,736,560 | A | 4/1998 | Cosford et al. | |
|---|---|---|---|---|
| 9,926,285 | B2 * | 3/2018 | Crowley | C07D 271/107 |
| 2014/0031395 | A1 | 1/2014 | Harvey et al. | |
| 2015/0175534 | A1 | 6/2015 | Harvey et al. | |

FOREIGN PATENT DOCUMENTS

| WO | 2012103583 A1 | 8/2012 |
|---|---|---|
| WO | 2014019023 A1 | 2/2014 |
| WO | 2015191799 A1 | 12/2015 |
| WO | 2017165256 A1 | 9/2017 |

* cited by examiner

*Primary Examiner* — Kamal A Saeed

(74) *Attorney, Agent, or Firm* — Patricia A. Shatynski; John C. Todaro

(57) ABSTRACT

The present disclosure relates to compounds of formula I that are useful as modulators of 7 nAChR, compositions comprising such compounds, and the use of such compounds for preventing, treating, or ameliorating disease, particularly disorders of the central nervous system such as cognitive impairments in Alzheimer's disease, Parkinson's disease, and schizophrenia, as well as for L-DOPA induced-dyskinesia and inflammation (I).

(I)

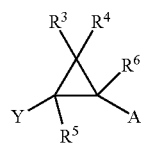

13 Claims, No Drawings

HETEROARYL ALLOSTERIC MODULATORS OF NICOTINIC ACETYLCHOLINE RECEPTORS

CROSS REFERENCE TO RELATED APPLICATIONS

This application is a U.S. National Phase application under 35 U.S.C. § 371 of PCT Application No. PCT/US2018/050975, filed Sep. 14, 2018 which claims priority under 35 U.S.C. § 119(e) from U.S. Provisional Application Serial No. 62/560,444, filed on Sep. 19, 2017.

FIELD OF THE INVENTION

The present disclosure relates to compounds that are useful as modulators of α7 nAChR, compositions comprising such compounds, and the use of such compounds for preventing, treating, or ameliorating disease, particularly disorders of the central nervous system such as cognitive impairments in Alzheimer's disease, Parkinson's disease, and schizophrenia.

BACKGROUND OF THE INVENTION

The α7 nAChR is a fast desensitizing ligand-gated ion channel that has high permeability to $Ca^{2+}$. In human brain, α7 nAChRs are highly expressed in the cortex and hippocampus, regions associated with cognition, see for example, Breese et al. *J. Comp. Neurol.* (1997) 387:385-398. In neurons, α7 nAChRs are localized in both pre-synaptic and post-synaptic structures, where activation of the receptor can modulate neurotransmitter release, neuronal excitability, and intracellular signalling, see for example, Frazier et al. *J. Neurosci.* (1998) 18:1187-1195.

Cognitive impairments are prevalent in many neurological and psychiatric diseases, including Alzheimer's disease (AD), schizophrenia, and Parkinson's disease, and dysfunction in cholinergic signalling contributes to the cognitive impairments of these diseases, see for example, Francis et al. *J. Neurol. Neurosurg. Psychiatry* (1999) 66:137-147. For example, a principal feature of the pathogenesis in AD is the loss of cholinergic neurons in the basal forebrain nuclei, whereas increasing cholinergic transmission via inhibition of acetylcholine esterase is the standard of care for the cognitive symptoms of AD. More specific to the α7 nAChR, it was recently demonstrated that encenicline, a partial agonist of the α7 nAChR, improves cognition in Alzheimer's disease, see for example, Moebius H et al., $67^{th}$ *Annual Meeting. Am. Acad. Neurol.* (AAN) 2015, Abst P7.100. Evidence implicating α7 nAChRs in the etiology of schizophrenia comes from studies demonstrating reduced expression of neuronal α7 nAChRs in the brain of schizophrenic patients and the observation that schizophrenics frequently smoke, which is believed to be a form of self-medication. In addition, variants in the promotor region of the gene coding for the α7 nAChR, CHRNA7, which impacts expression of the α7 nAChR protein, are associated with symptoms of schizophrenia, see for example, Sinkus et al. *Neuropharmacology* (2015) 96:274-288. Moreover, accumulating evidence from clinical trials has indicated that activating α7 nAChR with agonists may have beneficial effects on cognition, see for example, Keefe et al. *Neuropsychopharmacology* (2015) 40:3053-3060 and Bertrand et al. *Pharmacology Reviews* (2015) 67:1025-1073. Therefore, targeting the α7 nAChR represents a therapeutic strategy for the treatment of cognitive impairments associated with various cognitive disorders.

Parkinson's disease (PD) is a neurodegenerative disease characterized by progressive deficits in motor function, such as tremor, bradykinesia, rigidity and impaired postural reflex. The main pathological finding associated with the disease is degeneration of dopaminergic neurons in the substantia nigra, resulting in loss of dopaminergic tone in the striatum. L-DOPA is the current standard treatment for the motor symptoms in PD. However, chronic treatment with L-DOPA in PD patients also induces dyskinesia, a side effect of L-DOPA therapy. New lines of evidence indicate that activating α7 nAChRs acutely alleviates dyskinesia in several animal models, see for example, Zhang et al. *J. Pharmacol. Exp. Ther.* (2014) 351:25-32. In addition, accumulating evidence shows that pretreatment with α7 nAChR agonists may protect against neurodegeneration in nigrostriatal neurons, suggesting α7 activation may have disease modifying properties too, see for example, Suzuki et al. *J. Neurosci. Res.* (2013) 91:462-471. Overall, α7 nAChR is an attractive target for both ameliorating disease progression and managing dyskinesia.

In addition to its expression in the central nervous system, the α7 nAChR is widely expressed in peripheral immune cells including macrophage, monocytes, dendritic cells, and B and T cells, see for example, Rosas-Ballina et al. *Science* (2011) 334:98-101. Activation of peripheral α7 nAChRs is critical for inhibiting the release of proinflammatory cytokines via the cholinergic anti-inflammatory pathway, see for example, Wang et al. *Nature* (2003) 421:384-388. Therefore, α7 nAChR is a potential target for several inflammatory diseases such as rheumatoid arthritis, and atherosclerosis, see for example, W J de Jonge et al. *British J. Pharmacol.* (2007) 151:915-929.

In recent years, α7-selective positive allosteric modulators (PAMs) have been proposed as a therapeutic approach to treating cognitive impairments in AD, PD, and schizophrenia, as well as L-DOPA induced-dyskinesia and inflammation. In contrast to α7 agonists that activate the channel irrespective of endogenous agonist, PAMs increase the potency of the endogenous agonist without perturbing the temporal and spatial integrity of neurotransmission. There are two class of α7 PAMs, type I and type II, which differ based on the functional properties of modulation. The type I PAMs (e.g. NS1738, see for example, Timmermann et al. *J. Pharmacol. Exp. Ther.* (2007) 323:294-307) predominantly affect the peak current with little or no effect on receptor desensitization, while the type II PAMs (e.g. PNU120596, see for example, Hurst et al. *J. Neurosci.* (2005) 25:4396-4405) markedly delay desensitization of the receptor. Additionally, α7 nAChR PAMs may have improved selectivity over related channel targets, presumably through binding to non-conserved regions of the receptor.

The present invention is directed to a new class of compounds that exhibit positive allosteric modulation of the α7 nAChR.

SUMMARY OF THE INVENTION

The present disclosure relates to novel compounds of formula I and pharmaceutically acceptable salts thereof. These compounds may be useful, either as compounds or their pharmaceutically acceptable salts (when appropriate), in the modulation of the α7 nAChR, the prevention, treatment, or amelioration of disease, particularly disorders of the central nervous system such as cognitive impairments in Alzheimer's disease, Parkinson's disease, and schizophrenia and/or as pharmaceutical composition ingredients. As pharmaceutical composition ingredients, these compounds and their salts may be the primary active therapeutic agent, and, when appropriate, may be combined with other therapeutic agents including but not limited to acetylcholinesterase inhibitors, NMDA receptor antagonists, beta-secretase inhibitors, M4 mAChR agonists or PAMs, mGluR2 antagonists or NAMs or PAMs, 5-HT6 antagonists, histamine H3 receptor antagonists, PDE4 inhibitors, PDE9 inhibitors, HDAC6 inhibitors, antipsychotics, MAO-B inhibitors, and levodopa.

In one aspect, the present invention relates to a compound of formula I:

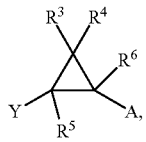

or a pharmaceutically acceptable salt thereof, wherein:
Y is selected from

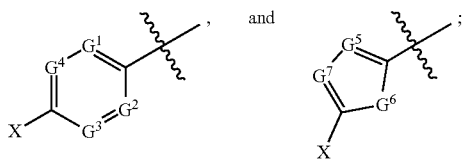

X is selected from

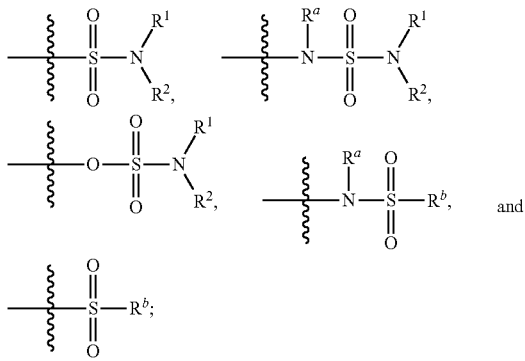

$G^1$ is $CR^9$, or N;
$G^2$ is $CR^9$, or N;
$G^3$ is $CR^9$, or N;
$G^4$ is is $CR^9$, or N;
provided that at least one of $G^1$-$G^4$ is N and at least two of $G^1$-$G^4$ are $CR^9$;
$G^5$ is $CR^9$, or N;
$G^6$ is O, or S;
$G^7$ is $CR^9$, or N;
A is an aryl or heteroaryl which is optionally substituted with 1 to 4 R groups each independently selected from OH, oxo, amino, amido, carboxyl, keto, cyano, alkoxy, $S(O)_m$-alkyl, halogen, aminoalkyl, hydroxyalkyl, alkyl, cycloalkyl, alkynyl, aryl, heteroaryl, and heterocyclyl, wherein said amino, amido, carboxyl, keto, alkoxy, $S(O)_m$-alkyl, aminoalkyl, hydroxyalkyl, alkyl, cycloalkyl, alkynyl, aryl, heteroaryl and heterocyclyl are optionally substituted with one or more substituents independently selected from halogen, OH, oxo, $CF_3$, $OCF_3$, CN, $(C_1$-$C_6)$alkyl, $O(C_1$-$C_4)$alkyl, $S(O)_m$-$(C_1$-$C_4)$alkyl, C=$O(C_1$-$C_4)$alkyl, (C=O)$NR^7R^8$, (C=O)$OR^7$, $(C_2$-$C_4)$alkynyl, $(C_3$-$C_6)$cycloalkyl, $O(C_3$-$C_6)$cycloalkyl, C=$O(C_3$-$C_6)$cycloalkyl, aryl, heteroaryl and heterocyclyl, wherein said alkyl, cycloalkyl, aryl, heteroaryl and heterocyclyl are optionally independently substituted with one or more halogen, $CF_3$, OH and oxo;
$R^1$ is H or $(C_1$-$C_4)$alkyl;
$R^2$ is H or $(C_1$-$C_4)$alkyl;
$R^3$ is H, halogen, $(C_1$-$C_4)$alkyl, wherein said alkyl is optionally substituted with one or more halogen;
$R^4$ is H, halogen or $(C_1$-$C_4)$alkyl, wherein said alkyl is optionally substituted with one or more halogen;
or, $R^3$ and $R^4$ optionally can come to together to form a cyclopropyl, cyclobutyl, cyclopentyl or cyclohexyl ring wherein said ring may be optionally substituted with one or more substituents independently selected from OH, halogen, or $(C_1$-$C_4)$alkyl;
$R^5$ is H or $(C_1$-$C_4)$alkyl;
$R^6$ is H or $(C_1$-$C_4)$alkyl;
$R^7$ and $R^8$ are independently selected from H, $(C_1$-$C_6)$ alkyl, cycloalkyl, aryl, heteroaryl and heterocyclyl, wherein said alkyl, cycloalkyl, aryl, heteroaryl and heterocyclyl are optionally substituted with one or more substituents independently selected from halogen, OH, $CF_3$, $(C_1$-$C_4)$alkyl, $O(C_1$-$C_4)$alkyl, cycloalkyl, CN, aryl, heteroaryl, and heterocyclyl, wherein said alkyl, cycloalkyl, aryl, heteroaryl and heterocyclyl are optionally substituted with one or more substituents independently selected from halogen, OH, $CF_3$, $(C_1$-$C_4)$alkyl, $O(C_1$-$C_4)$alkyl, and CN;
$R^9$ is is H or $(C_1$-$C_4)$alkyl;
$R^a$ is H or $(C_1$-$C_4)$alkyl;
$R^b$ is H or $(C_1$-$C_4)$alkyl; and
m is 0, 1, or 2.

The present invention also includes pharmaceutical compositions containing a compound of the present invention and methods of preparing such pharmaceutical compositions. The present invention further includes methods of preventing, treating, or ameliorating the cognitive impairments associated with Alzheimer's disease, Parkinson's disease, and schizophrenia.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts thereof. The compounds of formula I are positive allosteric modulators of α7 nAChR.

In a first embodiment of the invention, X is

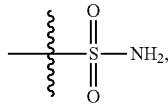

and the other groups are as provided in the general formula above.

In a second embodiment of the invention, $R^9$ is H or methyl.

In a third embodiment of the invention, A is an aryl or heteroaryl which is optionally substituted with 1 to 3 R groups independently selected from halogen, CN, $(C_1-C_6)$ alkyl, $O(C_1-C_6)$alkyl, $NR^7R^8$, $(C_3-C_6)$cycloalkyl, aryl, heteroaryl and heterocyclyl, wherein said alkyl, $NR^7R^8$, $(C_3-C_6)$cycloalkyl, aryl, heteroaryl and heterocyclyl are optionally substituted with one or more substituents independently selected from halogen, CN, $(C_1-C_4)$alkyl, (C=O)$O(C_1-C_4)$alkyl and phenyl, wherein said alkyl is optionally substituted with one or more halogen; and the other groups are as provided in the general formula above, or as in the first or second embodiment.

In a fourth embodiment of the invention, $R^5$, $R^6$, $R^a$ and $R^b$ are independently H or methyl, and the other groups are as provided in the general formula above, or as in the first, second, or third embodiments.

In a fifth embodiment of the invention, $R^3$ and $R^4$ are independently H, F, or methyl, and the other groups are as provided in the general formula above, or as in the first through fourth embodiments.

In a sixth embodiment of the invention, $R^7$ and $R^8$ are independently selected from H, $(C_1-C_6)$alkyl, cyclopentyl and phenyl wherein said alkyl and phenyl are optionally substituted with halogen or phenyl, and the other groups are as provided in the general formula above, or as in the first through fifth embodiments.

In a seventh embodiment of the invention, the compound of the invention has the formula:

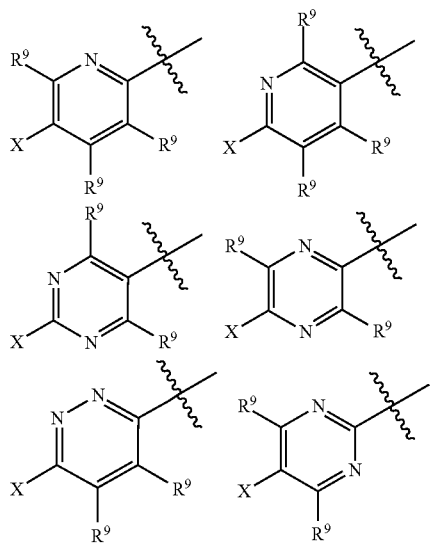
(I)

or a pharmaceutically acceptable salt thereof, wherein:

Y is selected from

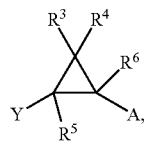

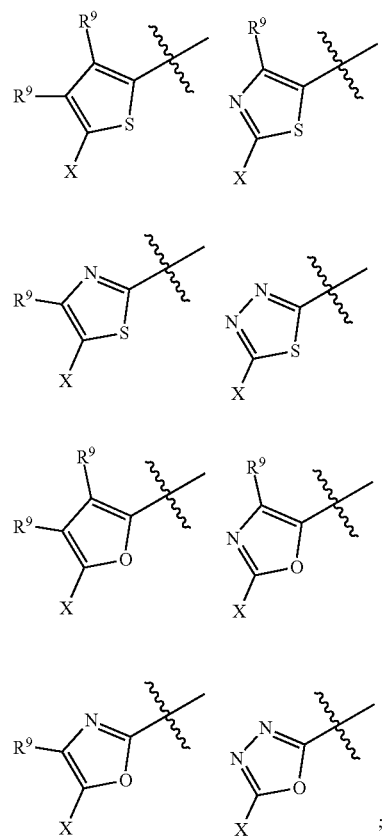

X is

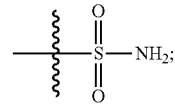 [SMILES: *S(N)(=O)=O]

A is selected from oxazolyl, thiazolyl, oxadiazolyl, thiadiazolyl, isoxazolyl, benzoxazolyl, isothiazolyl, triazolyl, pyrazolyl, quinazolinyl, oxazolopyridinyl, quinoxalinyl, imidazopyridazinyl, benzothiazolyl, naphthyridinyl, pyrazolopyridinyl, cinnolinyl, isoquinolyl, thienopyridinyl, indazolyl, furopyridinyl, phenyl, pyridinyl, pyrimidinyl, pyridazinyl and pyrazinyl each optionally substituted with 1-2 R groups independently selected from $(C_1-C_6)$alkyl, $O(C_1-C_6)$alkyl, $NR^7R^8$, $(C_3-C_6)$cycloalkyl, aryl, heteroaryl and heterocyclyl, wherein each are optionally substituted with one or more substituents independently selected from halogen, $CF_3$, CN, $(C_1-C_4)$alkyl, $O(C_1-C_6)$alkyl, (C=O)O $(C_1-C_4)$alkyl and phenyl;

$R^3$ is H or methyl;

$R^4$ is H or methyl;

$R^5$ is H or methyl;

$R^6$ is H or methyl;

$R^7$ and $R^8$ are independently selected from H, $(C_1-C_6)$alkyl, $(C_3-C_6)$cycloalkyl, aryl, heteroaryl and heterocyclyl; and $R^9$ is independently H or methyl.

In an eighth embodiment of the invention, the compound of the invention has the formula:

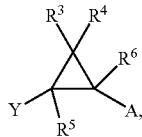

or a pharmaceutically acceptable salt thereof, wherein:
Y is selected from

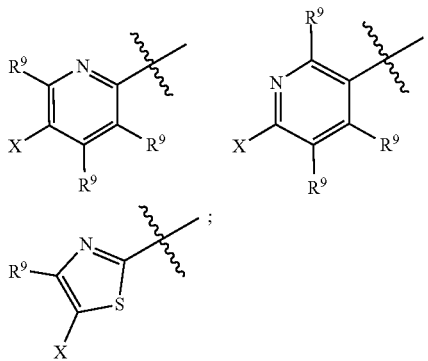

X is

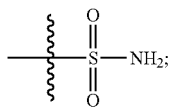

A is selected from oxazolyl, thiazolyl, oxadiazolyl, thiadiazolyl, isoxazolyl, and benzoxazolyl, each optionally substituted with 1 R group selected from $(C_1-C_6)$alkyl, $O(C_1-C_6)$alkyl, $NR^7R^8$, $(C_3-C_6)$cycloalkyl, phenyl, pyridinyl, morpholinyl, imidazolyl, pyrazolyl, oxadiazolyl, pyrrolidinyl, piperazinyl, triazolyl and tetrahydropyranyl wherein each are optionally substituted with one or more substituents independently selected from halogen, $CF_3$, CN, $(C_1-C_4)$ alkyl, $O(C_1-C_6)$alkyl, $(C_3-C_6)$cycloalkyl, $(C=O)O(C_1-C_4)$ alkyl and phenyl;
$R^3$ is H or methyl;
$R^4$ is H or methyl;
$R^5$ is H or methyl;
$R^6$ is H or methyl;
$R^7$ and $R^8$ are independently selected from H, $(C_1-C_6)$ alkyl, cyclopentyl and phenyl, wherein each alkyl, cyclopentyl, and phenyl are optionally substituted with one or more substituents independently selected from halogen and phenyl; and
$R^9$ is H or methyl.

The invention is also directed to a compound, or a pharmaceutically acceptable salt thereof, selected from the following exemplified compounds:
5-[trans-3-(1,3-Benzoxazol-2-yl)-2,2-dimethylcyclopropyl] pyridine-2-sulfonamide;
5-{trans-3-[5-(2,4-Difluorophenyl)-1,3,4-thiadiazol-2-yl]-2,2-dimethylcyclopropyl}pyridine-2-sulfonamide;
5-[(1S,3S)-2,2-Dimethyl-3-(3-phenyl-1,2,4-oxadiazol-5-yl) cyclopropyl]pyridine-2-sulfonamide;
5-[trans-2-(3-Phenyl-1,2,4-oxadiazol-5-yl)cyclopropyl] pyridine-2-sulfonamide;
6-Methyl-5-[trans-2-(3-phenyl-1,2,4-oxadiazol-5-yl)cyclopropyl]pyridine-2-sulfonamide;
2-[(1S,3S)-2,2-Dimethyl-3-(3-phenyl-1,2,4-oxadiazol-5-yl) cyclopropyl]-1,3-thiazole-5-sulfonamide;
5-[(1R,3R)-3-(3-Cyclohexyl-1,2,4-oxadiazol-5-yl)-2,2-dimethylcyclopropyl]pyridine-2-sulfonamide;
5-[(1S,3S)-2,2-Dimethyl-3-(5-phenyl-1,3-oxazol-2-yl)cyclopropyl]pyridine-2-sulfonamide;
5-[(1R,3R)-3-(5-Cyclopentyl-1,3-thiazol-2-yl)-2,2-dimethylcyclopropyl]pyridine-2-sulfonamide;
6-[(1S,3S)-3-(3-Cyclohexyl-1,2,4-oxadiazol-5-yl)-2,2-dimethylcyclopropyl]pyridine-3-sulfonamide;
5-[trans-2,2-Dimethyl-3-(5-phenyl-1,2,4-oxadiazol-3-yl)cyclopropyl]pyridine-2-sulfonamide;
5-[trans-3-(3-Cyclopentylisoxazol-5-yl)-2,2-dimethylcyclopropyl]pyridine-2-sulfonamide;
5-{trans-3-[5-(3-Fluorophenyl)isoxazol-3-yl]-2,2-dimethylcyclopropyl}pyridine-2-sulfonamide;
5-[(1R,3R)-2,2-Dimethyl-3-(3-phenyl-1,2,4-oxadiazol-5-yl) cyclopropyl]pyridine-2-sulfonamide;
5-[(1R,3R)-2,2-Dimethyl-3-{3-[5-(trifluoromethyl)pyridin-3-yl]-1,2,4-oxadiazol-5-yl}cyclopropyl]pyridine-2-sulfonamide;
5-[(1R,3R)-3-(3-Cyclopentyl-1,2,4-oxadiazol-5-yl)-2,2-dimethylcyclopropyl]pyridine-2-sulfonamide;
5-[(1R,3R)-3-(5-Cyclopentyl-1,3-oxazol-2-yl)-2,2-dimethylcyclopropyl]pyridine-2-sulfonamide;
5-[(1R,3R)-2,2-Dimethyl-3-(5-phenyl-1,3-thiazol-2-yl)cyclopropyl]pyridine-2-sulfonamide;
5-{(1R,3R)-3-[3-(5-Chloro-2-methoxyphenyl)-1,2,4-oxadiazol-5-yl]-2,2-dimethylcyclopropyl}pyridine-2-sulfonamide;
5-{(1R,3R)-3-[3-(3-Fluorophenyl)-1,2,4-oxadiazol-5-yl]-2,2-dimethylcyclopropyl}pyridine-2-sulfonamide;
5-{(1R,3R)-3-[3-(2,4-Difluorophenyl)-1,2,4-oxadiazol-5-yl]-2,2-dimethylcyclopropyl}pyridine-2-sulfonamide;
5-{(1R,3R)-3-[3-(5-Fluoropyridin-3-yl)-1,2,4-oxadiazol-5-yl]-2,2-dimethylcyclopropyl}pyridine-2-sulfonamide;
5-[(1R,3R)-2,2-Dimethyl-3-{3-[3-(trifluoromethyl)phenyl]-1,2,4-oxadiazol-5-yl}cyclopropyl]pyridine-2-sulfonamide;
5-{(1R,3R)-3-[3-(3,3-Difluorocyclobutyl)-1,2,4-oxadiazol-5-yl]-2,2-dimethylcyclopropyl}pyridine-2-sulfonamide;
5-[(1R,3R)-3-(3-Cyclobutyl-1,2,4-oxadiazol-5-yl)-2,2-dimethylcyclopropyl]pyridine-2-sulfonamide;
5-{(1R,3R)-3-[3-(Cyclopropylmethyl)-1,2,4-oxadiazol-5-yl]-2,2-dimethylcyclopropyl}pyridine-2-sulfonamide;
5-{(1R,3R)-2,2-Dimethyl-3-[3-(propan-2-yl)-1,2,4-oxadiazol-5-yl]cyclopropyl}pyridine-2-sulfonamide;
5-[(1R,3R)-2,2-Dimethyl-3-(5-phenyl-1,3-oxazol-2-yl)cyclopropyl]pyridine-2-sulfonamide;
5-{(1S,3S)-3-[3-(3-Fluorophenyl)-1,2,4-oxadiazol-5-yl]-2,2-dimethylcyclopropyl}pyridine-2-sulfonamide;
5-{(1S,3S)-3-[3-(5-Chloro-2-methoxyphenyl)-1,2,4-oxadiazol-5-yl]-2,2-dimethylcyclopropyl}pyridine-2-sulfonamide;
5-{(1S,3S)-3-[3-(2,4-Difluorophenyl)-1,2,4-oxadiazol-5-yl]-2,2-dimethylcyclopropyl}pyridine-2-sulfonamide;
5-[(1S,3S)-2,2-Dimethyl-3-{3-[5-(trifluoromethyl)pyridin-3-yl]-1,2,4-oxadiazol-5-yl}cyclopropyl]pyridine-2-sulfonamide;

5-[(1S,3S)-2,2-Dimethyl-3-{3-[3-(trifluoromethyl)phenyl]-1,2,4-oxadiazol-5-yl}cyclopropyl]pyridine-2-sulfonamide;

5-[(1S,3S)-3-(3-Cyclohexyl-1,2,4-oxadiazol-5-yl)-2,2-dimethylcyclopropyl]pyridine-2-sulfonamide;

5-[(1S,3S)-3-(3-Cyclopentyl-1,2,4-oxadiazol-5-yl)-2,2-dimethylcyclopropyl]pyridine-2-sulfonamide;

5-{(1S,3S)-3-[3-(3,3-Difluorocyclobutyl)-1,2,4-oxadiazol-5-yl]-2,2-dimethylcyclopropyl}pyridine-2-sulfonamide;

5-[(1S,3S)-3-(3-Cyclobutyl-1,2,4-oxadiazol-5-yl)-2,2-dimethylcyclopropyl]pyridine-2-sulfonamide;

5-{(1S,3S)-3-[3-(Cyclopropylmethyl)-1,2,4-oxadiazol-5-yl]-2,2-dimethylcyclopropyl}pyridine-2-sulfonamide;

5-[(1S,3S)-3-(3-Cyclopropyl-1,2,4-oxadiazol-5-yl)-2,2-dimethylcyclopropyl]pyridine-2-sulfonamide;

5-[(1S,3S)-3-(3-tert-Butyl-1,2,4-oxadiazol-5-yl)-2,2-dimethylcyclopropyl]pyridine-2-sulfonamide;

5-{(1S,3S)-2,2-Dimethyl-3-[3-(propan-2-yl)-1,2,4-oxadiazol-5-yl]cyclopropyl}pyridine-2-sulfonamide;

5-[(1S,3S)-3-(5-Cyclopentyl-1,3-oxazol-2-yl)-2,2-dimethylcyclopropyl]pyridine-2-sulfonamide;

5-[(1S,3S)-2,2-Dimethyl-3-(5-phenyl-1,3-thiazol-2-yl)cyclopropyl]pyridine-2-sulfonamide;

5-[(1S,3S)-3-(5-Cyclopentyl-1,3-thiazol-2-yl)-2,2-dimethylcyclopropyl]pyridine-2-sulfonamide; 5-{trans-2,2-Dimethyl-3-[5-(2,3,6-trifluorophenyl)-1,2,4-oxadiazol-3-yl]cyclopropyl}pyridine-2-sulfonamide;

5-[trans-3-(5-Cyclopentyl-1,2,4-oxadiazol-3-yl)-2,2-dimethylcyclopropyl]pyridine-2-sulfonamide;

5-{trans-3-[3-(3-Fluorophenyl)isoxazol-5-yl]-2,2-dimethylcycpropyl}pyridine-2-sulfonamide;

5-[trans-3-(1,3-Benzoxazol-2-yl)-2,2-dimethylcyclopropyl]pyridine-2-sulfonamide;

5-[trans-2-(3-Phenyl-1,2,4-oxadiazol-5-yl)cyclopropyl]pyridine-2-sulfonamide;

5-[trans-2,2-Dimethyl-3-(3-phenyl-1,2,4-oxadiazol-5-yl)cyclopropyl]pyridine-2-sulfonamide;

5-[trans-3-(1,3-Benzoxazol-2-yl)-2,2-dimethylcyclopropyl]pyridine-2-sulfonamide;

5-{trans-2-[3-(3-Fluorophenyl)-1,2,4-oxadiazol-5-yl]cyclopropyl}pyridine-2-sulfonamide;

5-[trans-2-(3-Cyclopentyl-1,2,4-oxadiazol-5-yl)cyclopropyl]pyridine-2-sulfonamide;

5-[trans-3-(5-Cyclohexyl-1,2,4-oxadiazol-3-yl)-2,2-dimethylcyclopropyl]pyridine-2-sulfonamide;

5-(trans-2,2-Dimethyl-3-{5-[1-(trifluoromethyl)cyclopropyl]-1,2,4-oxadiazol-3-yl}cyclopropyl)pyridine-2-sulfonamide;

5-{trans-3-[5-(2,6-Difluorophenyl)-1,2,4-oxadiazol-3-yl]-2,2-dimethylcyclopropyl}pyridine-2-sulfonamide;

5-{trans-3-[5-(3-Fluorophenyl)isoxazol-3-yl]-2,2-dimethylcyclopropyl}pyridine-2-sulfonamide;

2-[trans-3-(1,3-Benzoxazol-2-yl)-2,2-dimethylcyclopropyl]-1,3-thiazole-5-sulfonamide;

2-[trans-3-(3-Cyclobutyl-1,2,4-oxadiazol-5-yl)-2,2-dimethylcyclopropyl]-1,3-thiazole-5-sulfonamide;

2-{trans-3-[3-(5-Fluoropyridin-3-yl)-1,2,4-oxadiazol-5-yl]-2,2-dimethylcyclopropyl}-1,3-thiazole-5-sulfonamide;

2-[trans-2,2-Dimethyl-3-(3-phenyl-1,2,4-oxadiazol-5-yl)cyclopropyl]-1,3-thiazole-5-sulfonamide;

2-{trans-2,2-Dimethyl-3-[3-(propan-2-yl)-1,2,4-oxadiazol-5-yl]cyclopropyl}-1,3-thiazole-5-sulfonamide;

2-{trans-3-[3-(3,3-Difluorocyclobutyl)-1,2,4-oxadiazol-5-yl]-2,2-dimethylcyclopropyl}-1,3-thiazole-5-sulfonamide;

2-{trans-3-[3-(5-Chloro-2-methoxyphenyl)-1,2,4-oxadiazol-5-yl]-2,2-dimethylcyclopropyl}-1,3-thiazole-5-sulfonamide;

2-[trans-2-(3-Phenyl-1,2,4-oxadiazol-5-yl)cyclopropyl]-1,3-thiazole-5-sulfonamide;

2-[(1R,3R)-2,2-Dimethyl-3-(3-phenyl-1,2,4-oxadiazol-5-yl)cyclopropyl]-1,3-thiazole-5-sulfonamide;

6-{(1R,3R)-3-[3-(3-Fluorophenyl)-1,2,4-oxadiazol-5-yl]-2,2-dimethylcyclopropyl}pyridine-3-sulfonamide;

6-[(1R,3R)-3-(3-Cyclopentyl-1,2,4-oxadiazol-5-yl)-2,2-dimethylcyclopropyl]pyridine-3-sulfonamide;

6-[(1R,3R)-2,2-Dimethyl-3-(3-phenyl-1,2,4-oxadiazol-5-yl)cyclopropyl]pyridine-3-sulfonamide 6-{(1R,3R)-3-[3-(5-Chloro-2-methoxyphenyl)-1,2,4-oxadiazol-5-yl]-2,2-dimethylcyclopropyl}pyridine-3-sulfonamide;

6-{(1R,3R)-3-[3-(2,4-Difluorophenyl)-1,2,4-oxadiazol-5-yl]-2,2-dimethylcyclopropyl}pyridine-3-sulfonamide;

6-[(1R,3R)-2,2-Dimethyl-3-{3-[3-(trifluoromethyl)phenyl]-1,2,4-oxadiazol-5-yl}cyclopropyl]pyridine-3-sulfonamide;

6-[(1R,3R)-3-(3-Cyclohexyl-1,2,4-oxadiazol-5-yl)-2,2-dimethylcyclopropyl]pyridine-3-sulfonamide;

6-{(1S,3S)-3-[3-(3-Fluorophenyl)-1,2,4-oxadiazol-5-yl]-2,2-dimethylcyclopropyl}pyridine-3-sulfonamide;

6-[(1S,3S)-2,2-Dimethyl-3-{3-[5-(trifluoromethyl)pyridin-3-yl]-1,2,4-oxadiazol-5-yl}cyclopropyl]pyridine-3-sulfonamide;

6-[(1S,3S)-3-(3-Cyclopentyl-1,2,4-oxadiazol-5-yl)-2,2-dimethylcyclopropyl]pyridine-3-sulfonamide.

6-{(1S,3S)-3-[3-(5-Chloro-2-methoxyphenyl)-1,2,4-oxadiazol-5-yl]-2,2-dimethylcyclopropyl}pyridine-3-sulfonamide;

6-{(1S,3S)-3-[3-(2,4-Difluorophenyl)-1,2,4-oxadiazol-5-yl]-2,2-dimethylcyclopropyl}pyridine-3-sulfonamide;

6-[(1S,3S)-2,2-Dimethyl-3-{3-[3-(trifluoromethyl)phenyl]-1,2,4-oxadiazol-5-yl}cyclopropyl]pyridine-3-sulfonamide;

6-{(1S,3S)-3-[3-(Cyclopropylmethyl)-1,2,4-oxadiazol-5-yl]-2,2-dimethylcyclopropyl}pyridine-3-sulfonamide;

6-[(1S,3S)-3-(3-Cyclopropyl-1,2,4-oxadiazol-5-yl)-2,2-dimethylcyclopropyl]pyridine-3-sulfonamide;

6-[(1S,3S)-3-(3-tert-Butyl-1,2,4-oxadiazol-5-yl)-2,2-dimethylcyclopropyl]pyridine-3-sulfonamide;

6-[(1S,3S)-2,2-Dimethyl-3-(3-phenyl-1,2,4-oxadiazol-5-yl)cyclopropyl]pyridine-3-sulfonamide;

6-{(1S,3S)-3-[3-(5-Fluoropyridin-3-yl)-1,2,4-oxadiazol-5-yl]-2,2-dimethylcyclopropyl}pyridine-3-sulfonamide;

6-{(1S,3S)-3-[3-(3,3-Difluorocyclobutyl)-1,2,4-oxadiazol-5-yl]-2,2-dimethylcyclopropyl}pyridine-3-sulfonamide;

6-[(1S,3S)-3-(3-Cyclobutyl-1,2,4-oxadiazol-5-yl)-2,2-dimethylcyclopropyl]pyridine-3-sulfonamide;

6-{(1S,3S)-2,2-Dimethyl-3-[3-(propan-2-yl)-1,2,4-oxadiazol-5-yl]cyclopropyl}pyridine-3-sulfonamide;

6-[trans-3-(1,3-Benzoxazol-2-yl)-2,2-dimethylcyclopropyl]pyridine-3-sulfonamide;

6-[trans-2,2-Dimethyl-3-(3-phenyl-1,2,4-oxadiazol-5-yl)cyclopropyl]pyridine-3-sulfonamide;

6-{trans-2,2-Dimethyl-3-[3-(propan-2-yl)-1,2,4-oxadiazol-5-yl]cyclopropyl}pyridine-3-sulfonamide;

6-[trans-3-(3-Cyclobutyl-1,2,4-oxadiazol-5-yl)-2,2-dimethylcyclopropyl]pyridine-3-sulfonamide;

6-{trans-3-[3-(3,3-Difluorocyclobutyl)-1,2,4-oxadiazol-5-yl]-2,2-dimethylcyclopropyl}pyridine-3-sulfonamide;

6-[trans-2-(3-Phenyl-1,2,4-oxadiazol-5-yl)cyclopropyl]pyridine-3-sulfonamide; and 6-[trans-2-(3-Cyclopentyl-1,2,4-oxadiazol-5-yl)cyclopropyl]pyridine-3-sulfonamide.

Other embodiments of the present invention include the following:

(a) A pharmaceutical composition comprising a compound of formula I and a pharmaceutically acceptable carrier.

(b) The pharmaceutical composition of (a), further comprising a second therapeutic agent selected from the group consisting of acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa.

(c) The pharmaceutical composition of (b), wherein the second therapeutic agent is an antipsychotic selected from the group consisting of clozapine, olanzapine, risperidone, aripiprazole, quetiapine, haloperidol, loxapine, thioridazine, molindone, thiothixene, fluphenazine, mesoridazine, trifluoperazine, chlorpromazine, and perphenazine.

(d) A pharmaceutical combination that is (i) a compound of formula I and (ii) a second therapeutic agent selected from the group consisting of acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa wherein the compound of formula I and the second therapeutic agent are each employed in an amount that renders the combination effective for treating cognitive impairments associated with Alzheimer's disease, Parkinson's disease, and schizophrenia.

(e) The combination of (d), wherein the second therapeutic agent is an antipsychotic selected from the group consisting of clozapine, olanzapine, risperidone, aripiprazole, quetiapine, haloperidol, loxapine, thioridazine, molindone, thiothixene, fluphenazine, mesoridazine, trifluoperazine, chlorpromazine, and perphenazine.

(f) A use of a compound of formula I in the preparation of a medicament for modulating α7 nAChR activity in a subject in need thereof.

(g) A use of a compound of formula I in the preparation of a medicament for treating cognitive impairments associated with Alzheimer's disease, Parkinson's disease, and schizophrenia in a subject in need thereof.

(h) A method of treating cognitive impairments associated with Alzheimer's disease, Parkinson's disease, and schizophrenia and/or reducing the likelihood or severity of symptoms of cognitive impairments associated with Alzheimer's disease, Parkinson's disease, and schizophrenia in a subject in need thereof, which comprises administering to the subject an effective amount of a compound of formula I.

(i) The method of (h), wherein the compound of formula I is administered in combination with an effective amount of at least one second therapeutic agent selected from the group consisting of acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa.

(j) The method of (i), wherein the second therapeutic agent is an antipsychotic selected from the group consisting of clozapine, olanzapine, risperidone, aripiprazole, quetiapine, haloperidol, loxapine, thioridazine, molindone, thiothixene, fluphenazine, mesoridazine, trifluoperazine, chlorpromazine, and perphenazine.

(k) A method of modulating α7 nAChR activity in a subject in need thereof, which comprises administering to the subject the pharmaceutical composition of (a), (b), or (c) or the combination of (d) or (e).

(l) A method of treating cognitive impairments associated with Alzheimer's disease, Parkinson's disease, and schizophrenia and/or reducing the likelihood or severity of symptoms of cognitive impairments associated with Alzheimer's disease, Parkinson's disease, and schizophrenia in a subject in need thereof, which comprises administering to the subject the pharmaceutical composition of (a), (b), or (c) or the combination of (d) or (e).

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (l) above are understood to include all embodiments of the compounds and/or salts, including such embodiments as result from combinations of embodiments.

Additional embodiments of the invention include the pharmaceutical compositions, combinations, uses and methods set forth in (a) through (l) above, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

The present invention also includes a compound of the present invention for use (i) in, (ii) as a medicament for, or (iii) in the preparation of a medicament for: (a) preventing or treating cognitive impairments associated with Alzheimer's disease, Parkinson's disease, schizophrenia, and L-DOPA induced-dyskinesia, or (b) treating cognitive impairments associated with Alzheimer's disease, Parkinson's disease, schizophrenia, and L-DOPA induced-dyskinesia and/or reducing the likelihood or severity of symptoms of cognitive impairments associated with Alzheimer's disease, Parkinson's disease, schizophrenia, and L-DOPA induced-dyskinesia, or (c) use in medicine. In these uses, the compounds of the present invention can optionally be employed in combination with one or more second therapeutic agents selected from acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN- 101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa.

Chemical names, common names, and chemical structures may be used interchangeably to describe the same structure.

As used herein, the term "administration" and variants thereof (e.g., "administering" a compound) in reference to a compound of the invention means providing the compound to the individual in need of treatment. When a compound of the invention is provided in combination with one or more other active agents (e.g., cholinesterase inhibitors such as donepezil, rivastigmine, and galantamine), "administration" and its variants are each understood to include concurrent and sequential provision of the compound or salt and other agents.

The term "alkoxy" refers to an "alkyl-O—" group. Alkoxy groups may be substituted as indicated.

The term "alkyl" refers to an aliphatic hydrocarbon group having one of its hydrogen atoms replaced with a bond. An alkyl group may be straight or branched and contain from 1 to 12 carbon atoms. In different embodiments, an alkyl group contains from 1 to 6 carbon atoms [$(C_1-C_6)$alkyl] or from 1 to 4 carbon atoms [$(C_1-C_4)$alkyl] or from 1 to 3 carbon atoms [$(C_1-C_3)$alkyl]. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

The term "alkynyl" refers to a hydrocarbon radical straight or branched containing from 2 to 12 carbon atoms and at least one carbon to carbon triple bond. Up to three carbon-carbon triple bonds may be present. Thus, "$C_2-C_6$ alkynyl" means an alkynyl radical having from 2 to 6 carbon atoms. Alkynyl groups include ethynyl, propynyl, butynyl, 3-methylbutynyl and so on. In one embodiment, an alkynyl group is linear. In another embodiment, an alkynyl group is branched.

The term "aryl" (or "aryl ring") refers to any mono- and poly-carbocyclic ring systems wherein the individual carbocyclic rings in the polyring systems are fused or attached to each other via a single bond and wherein at least one ring is aromatic. Suitable aryl groups include phenyl, indanyl, naphthyl, tetrahydronaphthyl, and biphenyl. Aryl ring systems may include, where appropriate, an indication of the variable to which a particular ring atom is attached. Unless otherwise indicated, substituents to the aryl ring systems can be attached to any ring atom, provided that such attachment results in formation of a stable ring system.

The term "composition" is intended to encompass a product comprising the specified ingredients, as well as any product which results from combining the specified ingredients.

The term "compound" is intended to encompass chemical agents described by generic formula I in all forms. Such chemical agents can be present in different forms such as hydrates, solvates, and polymorphs.

The term "cycloalkyl" as used herein, refers to a non-aromatic mono- or multicyclic ring system comprising from 3 to 10 ring carbon atoms. In one embodiment, a cycloalkyl contains from 5 to 10 ring carbon atoms. In another embodiment, a cycloalkyl contains from 3 to 7 ring atoms. In another embodiment, a cycloalkyl contains from 3 to 6 ring atoms [$(C_3-C_6)$cycloalkyl]. In another embodiment, a cycloalkyl contains from 5 to 7 ring atoms. In another embodiment, a cycloalkyl contains from 5 to 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl, bicyclo[3.1.0]hexyl and adamantyl. The term "3 to 7-membered cycloalkyl" refers to a cycloalkyl group having from 3 to 7 ring carbon atoms. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

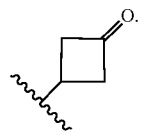 [SMILES: *C1CC(=O)C1]

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. The term also includes herein the amount of active compound sufficient to modulate α7 nAChR activity and thereby elicit the response being sought (i.e., a "therapeutically effective amount"). When the active compound (i.e., active ingredient) is administered as the salt, references to the amount of active ingredient are to the free acid or free base form of the compound.

The term "halogen" (or "halo") refers to atoms of fluorine, chlorine, bromine and iodine (alternatively referred to as fluoro, chloro, bromo, and iodo).

The term "heteroaryl" refers to a stable 5- to 10-membered aromatic heterocycle containing from 1 to 5 heteroatoms selected from the group consisting of O, N, and S, and includes monocyclic or bicyclic groups. Further examples of "heteroaryl" include, but are not limited to the following: benzimidazolyl, benzimidazolonyl, benzofuranyl, benzofurazanyl, benzopyrazolyl, benzothiazolyl, benzotriazolyl, benzothiophenyl, benzoxazolyl, carbazolyl, carbolinyl, cinnolinyl, furanyl, furanylpyrazolyl, furopyridinyl, imidazolyl, imidazopyridazinyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolopyridinyl, oxazolyl, pyrazinyl, pyrazolopyridinyl, pyrazolyl, pyridazinyl, pyridopyridinyl, pyridazinyl, pyridinyl, pyrimidinyl, pyrrolyl, pyrrolylpyrazolyl, quinazolinyl, quinolyl, quinoxalinyl, tetrazolyl, tetrazolopyridyl, thiadiazolyl, thiazolyl, thienopyridinyl, thienyl, thienylpyrazolyl, triazolyl, and the like, and all isomeric forms thereof. Attachment of a heteroaryl substituent can occur via a carbon atom or via a heteroatom.

The term "heterocycle" or "heterocyclyl" as used herein is intended to mean a 3- to 10-membered non-aromatic heterocycle containing from 1 to 4 heteroatoms selected from the group consisting of O, N, and S, and includes monocyclic or bicyclic groups (fused, bridged or spirocyclic). Further examples of "heterocyclyl" include, but are not limited to the following: oxazoline, isoxazoline, oxetanyl, tetrahydropyranyl, azetidinyl, 1,4-dioxanyl, hexahydroazepinyl, piperazinyl, piperidinyl, pyrrolidinyl, morpholinyl, thiomorpholinyl, dihydrofuranyl, dihydroimidazolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydrotetrazolyl, dihydrothiadiazolyl, dihydrothiazolyl, dihydrothienyl, dihydrotriazolyl, tetrahydrofuranyl, and tetrahydrothienyl, and N-oxides thereof. Attachment of a heterocyclyl substituent can occur via a carbon atom or via a heteroatom.

The term "hydroxyalkyl" as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms. The term "C$_1$-C$_4$ hydroxyalkyl" refers to a hydroxyalkyl group having from 1 to 4 carbon atoms. The term "C$_1$-C$_3$ hydroxyalkyl" refers to a hydroxyalkyl group having from 1 to 3 carbon atoms.

As used herein, the term "oxo" or "=O" forms a carbonyl moiety with the carbon atom to which it is attached.

By "pharmaceutically acceptable" is meant that the ingredients of the pharmaceutical composition must be compatible with each other and not deleterious to the recipient thereof.

The term "preventing" as used herein with respect to Alzheimer's disease or other neurological diseases, refers to reducing the likelihood of disease progression.

The term "subject" (alternatively referred to herein as "patient"), as used herein, refers to an animal, preferably a mammal, most preferably a human.

The term "substituted" means that one or more hydrogens on the designated atom is replaced with a selection from the indicated group, provided that the designated atom's normal valency under the existing circumstances is not exceeded, and that the substitution results in a stable compound. Unless expressly stated to the contrary, substitution by a named substituent is permitted on any atom provided such substitution is chemically allowed and results in a stable compound. Combinations of substituents and/or variables are permissible only if such combinations result in stable compounds. A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject).

In another embodiment of formula I, X is selected from

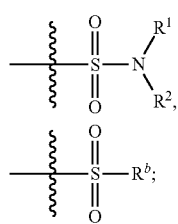 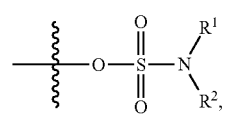

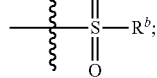

wherein R$^1$, R$^2$, and R$^b$ is H.

In another embodiment of formula I, X is

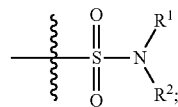

wherein R$^1$ and R$^2$ are H.

In another embodiment of formula I, Y is selected from

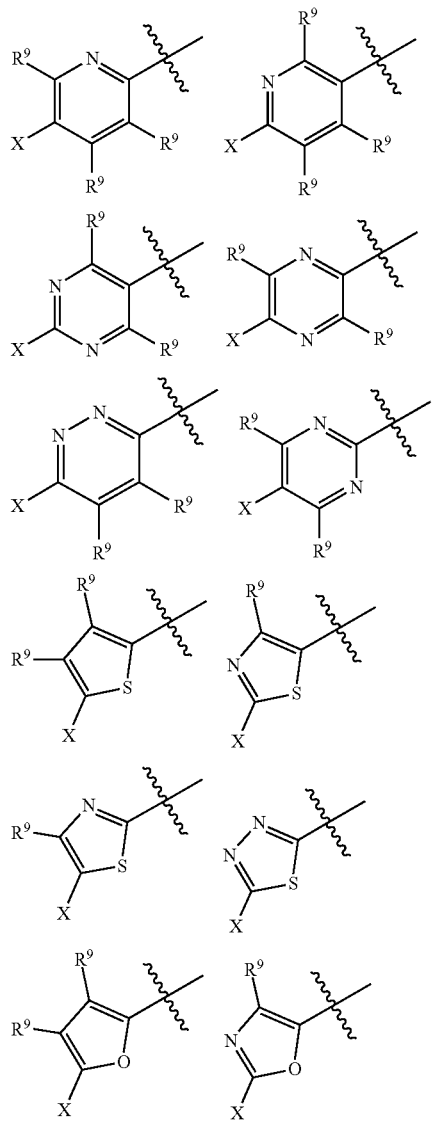

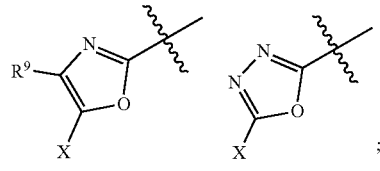

wherein R$^9$ is independently H or methyl.

In another embodiment of formula I, Y is selected from

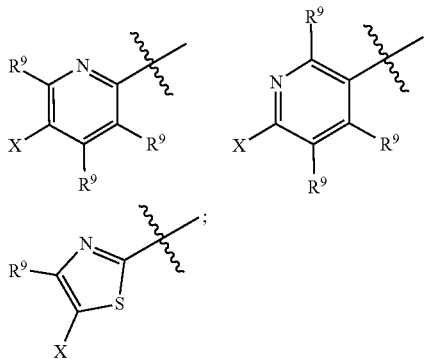

wherein $R^9$ is independently H or methyl.

In another embodiment of formula I, A is an aryl or heteroaryl which is substituted with 1 to 3 R groups independently selected from OH, oxo, halogen, CN, $(C_1-C_6)$alkyl, $O(C_1-C_6)$alkyl, $NR^7R^8$, $(C_3-C_6)$cycloalkyl, aryl, heteroaryl and heterocyclyl, wherein each are optionally substituted with one or more substituents independently selected from halogen, CN, $CF_3$, $(C_1-C_4)$alkyl, $(C_3-C_6)$cycloalkyl, $O(C_1-C_4)$alkyl, $(C=O)O(C_1-C_4)$alkyl and phenyl.

In another embodiment of formula I, A is an aryl or heteroaryl which is substituted with 1 to 2 R groups independently selected from OH, oxo, halogen, CN, $(C_1-C_6)$alkyl, $O(C_1-C_6)$alkyl, $NR^7R^8$, $(C_3-C_6)$cycloalkyl, aryl, heteroaryl and heterocyclyl, wherein each are optionally substituted with one or more substituents independently selected from halogen, CN, $CF_3$, $(C_1-C_4)$alkyl, $(C_3-C_6)$cycloalkyl, $O(C_1-C_4)$alkyl, $(C=O)O(C_1-C_4)$alkyl and phenyl.

In another embodiment of formula I, A is selected from oxazolyl, thiazolyl, oxadiazolyl, thiadiazolyl, isoxazolyl, benzoxazolyl, isothiazolyl, triazolyl, pyrazolyl, quinazolinyl, oxazolopyridinyl, quinoxalinyl, imidazopyridazinyl, benzothiazolyl, naphthyridinyl, pyrazolopyridinyl, cinnolinyl, isoquinolyl, thienopyridinyl, indazolyl, furopyridinyl, pyridinyl, pyrimidinyl, pyridazinyl, and pyrazinyl, each optionally substituted with 1 to 3 R groups independently selected from $(C_1-C_6)$alkyl, $O(C_1-C_6)$alkyl, $NR^7R^8$, $(C_3-C_6)$cycloalkyl, aryl, heteroaryl and heterocyclyl, wherein each are optionally substituted with one or more substituents independently selected from halogen, CN, $CF_3$, $(C_1-C_4)$alkyl, $(C_3-C_6)$cycloalkyl, $O(C_1-C_4)$alkyl, $(C=O)O(C_1-C_4)$alkyl and phenyl.

In another embodiment of formula I, A is selected from oxazolyl, thiazolyl, oxadiazolyl, thiadiazolyl, isoxazolyl, benzoxazolyl, isothiazolyl, pyrazolyl, quinazolinyl, quinoxalinyl, benzothiazolyl, naphthyridinyl, isoquinolyl, indazolyl, pyridinyl, pyrimidinyl, and pyrazinyl, each optionally substituted with 1 to 3 R groups independently selected from $(C_1-C_6)$alkyl, $O(C_1-C_6)$alkyl, $NR^7R^8$, $(C_3-C_6)$cycloalkyl, aryl, heteroaryl and heterocyclyl, wherein each are optionally substituted with one or more substituents independently selected from halogen, CN, $CF_3$, $(C_1-C_4)$alkyl, $(C_3-C_6)$cycloalkyl, $O(C_1-C_4)$alkyl, $(C=O)O(C_1-C_4)$alkyl and phenyl.

In another embodiment of formula I, A is selected from oxazolyl, thiazolyl, oxadiazolyl, thiadiazolyl, isoxazolyl, and benzoxazolyl, each substituted with 1 to 2 R groups independently selected from $(C_1-C_6)$alkyl, $O(C_1-C_6)$alkyl, $NR^7R^8$, $(C_3-C_6)$cycloalkyl, aryl, heteroaryl and heterocyclyl, wherein each are optionally substituted with one or more substituents independently selected from halogen, CN, $CF_3$, $(C_1-C_4)$alkyl, $(C_3-C_6)$cycloalkyl, $O(C_1-C_4)$alkyl, $(C=O)O(C_1-C_4)$alkyl and phenyl.

In another embodiment of formula I, A is selected from oxazolyl, thiazolyl, oxadiazolyl, thiadiazolyl, isoxazolyl, and benzoxazolyl, each substituted with 1 to 3 R groups independently selected from $(C_1-C_6)$alkyl, $O(C_1-C_6)$alkyl, $NR^7R^8$, $(C_3-C_6)$cycloalkyl, phenyl, pyridinyl, and tetrahydropyranyl wherein each are optionally substituted with one or more substituents independently selected from halogen, CN, $CF_3$, $(C_1-C_4)$alkyl, $(C_3-C_6)$cycloalkyl, $O(C_1-C_4)$alkyl, and phenyl.

In another embodiment of formula I, A is selected from oxazolyl, thiazolyl, oxadiazolyl, thiadiazolyl, isoxazolyl, and benzoxazolyl, each optionally substituted with 1 to 2 R groups independently selected from $(C_1-C_6)$alkyl, $O(C_1-C_6)$alkyl, $NR^7R^8$, $(C_3-C_6)$cycloalkyl, phenyl, and pyridinyl wherein each are optionally substituted with one or more substituents independently selected from halogen, CN, $CF_3$, $(C_1-C_4)$alkyl, $(C_3-C_6)$cycloalkyl, methoxy, and phenyl.

In another embodiment of formula I, A is selected from oxazolyl, thiazolyl, oxadiazolyl, thiadiazolyl, isoxazolyl, and benzoxazolyl, each optionally substituted with 1 R group independently selected from $(C_1-C_6)$alkyl, $(C_3-C_6)$cycloalkyl, phenyl, and pyridinyl wherein each are optionally substituted with one or more substituents independently selected from F, Cl, $CF_3$, cyclopropyl, and methoxy.

In another embodiment of formula I, A is selected from oxazolyl, thiazolyl, oxadiazolyl, thiadiazolyl, isoxazolyl, and benzoxazolyl, each substituted with 1 R group independently selected from $(C_1-C_6)$alkyl, $(C_3-C_6)$cycloalkyl, phenyl, and pyridinyl wherein each are optionally substituted with one or more substituents independently selected from F, Cl, $CF_3$, cyclopropyl, and methoxy.

In another embodiment of formula I, $R^1$ is H or methyl.
In another embodiment of formula I, $R^2$ is H or methyl.
In another embodiment of formula I, $R^3$ is H or methyl.
In another embodiment of formula I, $R^4$ is H or methyl.
In another embodiment of formula I, $R^3$ is methyl.
In another embodiment of formula I, $R^4$ is methyl.
In another embodiment of formula I, $R^3$ and $R^4$ optionally can come to together to form a cyclopropyl, cyclobutyl, cyclopentyl or cyclohexyl ring wherein said ring may be optionally substituted with one or more substituents independently selected from OH, halogen, or $(C_1-C_4)$alkyl.
In another embodiment of formula I, $R^3$ and $R^4$ optionally can come to together to form a cyclopropyl, cyclobutyl, cyclopentyl or cyclohexyl ring.
In another embodiment of formula I, $R^5$ is H or methyl.
In another embodiment of formula I, $R^6$ is H or methyl.
In another embodiment of formula I, $R^a$ is H or methyl.
In another embodiment of formula I, $R^b$ is H or methyl.
In another embodiment of formula I, $R^5$ is H.
In another embodiment of formula I, $R^6$ is H.
In another embodiment of formula I, $R^7$ and $R^8$ are independently selected from H, $(C_1-C_6)$alkyl, $(C_3-C_6)$cycloalkyl and phenyl.
In another embodiment of formula I, $R^7$ and $R^8$ are independently selected from H, $(C_1-C_6)$alkyl, cyclopentyl and phenyl.
In another embodiment of formula I, $R^7$ and $R^8$ are independently selected from H and $(C_1-C_4)$alkyl.
In another embodiment of formula I, $R^7$ and $R^8$ are independently selected from H and methyl.

In another embodiment of formula I, $R^9$ is independently H or methyl.

In another embodiment of formula I, $R^a$ is H.

In another embodiment of formula I, $R^b$ is H.

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of formula I. For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within formula I can be prepared without undue experimentation by conventional techniques well known to those skilled in the art or by processes analogous to those described in the Schemes and Examples herein using appropriate isotopically-enriched reagents and/or intermediates.

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

It is understood by one skilled in the art that carbon atoms in organic molecules may often be replaced by silicon atoms to give analogous stable compounds. For example, carbon atoms in alkoxy, alkyl, cycloalkyl, heteroaryl, heterocyclyl, and hydroxyalkyl groups may often be replaced by silicon atoms to provide stable compounds. All such compounds are within the scope of the present invention.

When any variable (for example, R) occurs more than one time in any constituent or in formula I or in any other formula depicting and describing compounds of the invention, its definition on each occurrence is independent of its definition at every other occurrence. Also, combinations of substituents and/or variables are permissible only if such combinations result in stable compounds.

Certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

Certain of the compounds of the present invention can exist as tautomers. For the purposes of the present invention a reference to a compound of formula I is a reference to the compound per se, or to any one of its tautomers per se, or to mixtures of two or more tautomers.

The compounds of the present invention may have utility in preventing, treating, or ameliorating Alzheimer's disease. The compounds may also be useful in preventing, treating, or ameliorating other diseases mediated by the α7 nAChR, such as schizophrenia, sleep disorders, Parkinson's disease, autism, microdeletion syndrome, inflammatory diseases, pain disorders (including acute pain, inflammatory pain and neuropathic pain) and cognitive disorders (including mild cognitive impairment). Other conditions that may be prevented, treated, or ameliorated by the compounds of the invention include pulmonary hypertension, chronic obstructive pulmonary disease (COPD), asthma, urinary incontinence, glaucoma, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, kidney diseases, cancer, and atherosclerosis.

In preferred embodiments, the compounds of the invention may be useful in preventing, treating, or ameliorating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

Thus, in another specific embodiment, the present invention provides a method for preventing, treating, or ameliorating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression; emotional/mood disorders; as well as sleep walking and enuresis; and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis); repetitive motion pain; dental pain; cancer pain; myofascial pain (muscular injury, fibromyalgia); perioperative pain (general surgery, gynecological); chronic pain; dysmennorhea, as well as pain associated with angina, and inflammatory pain of varied origins (e.g. osteoarthritis, rheumatoid arthritis, rheumatic disease, teno-synovitis and gout); headache; migraine and cluster headache; primary hyperalgesia; secondary hyperalgesia; primary allodynia; secondary allodynia; or other pain caused by central sensitization.

Potential conditions or disorders that have a strong inflammatory component for which the compounds of the invention may be useful include one or more of the following conditions or diseases: diabetes (systemic inflammation in diabetes marked by increases in blood cytokines e.g. IL-6 and TNFα which may lead to insulin resistance); asthma; arthritis; cystic fibrosis; sepsis; ulcerative colitis; inflammatory bowel disease; atherosclerosis; neuroinflammation associated with neurodegenerative diseases (e.g. Alzheimer's disease, Parkinson's disease, Creutzfeldt-Jacob disease, frontotemporal dementia, corticobasal degeneration, Pick's disease, progressive supranuclear palsy, traumatic brain injury, Huntington's disease, amyotrophic lateral sclerosis).

Compounds of the invention may also be used to treat or prevent or ameliorate dyskinesia and protect against neurodegeneration in nigrostriatal neurons in Parkinson's disease. Furthermore, compounds of the invention may be used to decrease tolerance and/or dependence to opioid treatment of pain, and for treatment of withdrawal syndrome of e.g., alcohol, opioids, and cocaine.

The compounds of the present invention may be administered in the form of pharmaceutically acceptable salts. The term "pharmaceutically acceptable salt" refers to a salt that possesses the effectiveness of the parent compound and that is not biologically or otherwise undesirable (e.g., is neither toxic nor otherwise deleterious to the recipient thereof). Suitable salts include acid addition salts that may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1):1-19; P. Gould, *International J. of Pharmaceutics* (1986) 33:201-217; Anderson et al, *The Practice of Medicinal Chemistry* (1996), Academic Press, New York; and in *The Orange Book* (Food & Drug Administration, Washington, D.C. on their website).

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For the purposes of preventing, treating, or ameliorating the cognitive impairments in Alzheimer's disease, Parkinson's disease, schizophrenia, L-DOPA induced-dyskinesia, and inflammation, the compounds of the present invention, optionally in the form of a salt, can be administered by any means that produces contact of the active agent with the agent's site of action. They can be administered by one or more conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following: orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in Remington's Pharmaceutical Sciences, 18$^{th}$ edition (ed. A. R. Gennaro, Mack Publishing Co., 1990).

The compounds of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, and 500 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, and the severity of the particular condition.

As noted above, the present invention also relates to a method of preventing, treating, or ameliorating the cognitive impairments in Alzheimer's disease, Parkinson's disease, schizophrenia, L-DOPA induced-dyskinesia, and inflammation with a compound of the present invention in combination with one or more therapeutic agents and a pharmaceutical composition comprising a compound of the present invention and one or more therapeutic agents selected from the group consisting of anti-Alzheimer's Disease agents, for example beta-secretase inhibitors such as verubecestat; M1 mAChR agonist or PAMs; M4 mAChR agonists or PAMs; mGluR2 antagonists or NAMs or PAMs; ADAM 10 ligands or activators; gamma-secretase inhibitors, such as LY450139 and TAK 070; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; LRRK2 inhibitors; HMG-CoA reductase inhibitors; NSAIDs including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine H3 receptor antagonists such as ABT-834, ABT 829, GSK 189254 and CEP16795; AMPA agonists or AMPA modulators, such as CX-717, LY 451395, LY404187 and S-18986; PDE IV inhibitors, including MEM1414, HT0712 and AVE8112; GABA$_A$ inverse agonists; GSK3β inhibitors, including AZD1080, SAR502250 and CEP16805; neuronal nicotinic agonists; selective M1 agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of combinations of the compounds of the instant invention include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the compounds of the instant invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride; COMT inhibitors such as entacapone, MAO-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the compound of the instant invention may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the compounds of the instant invention may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the compounds of the instant invention may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds of the instant invention include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase Bl5 ("MAO-B") inhibitors; 5HT receptor agonists or antagonists; mGlu5 antagonists, such as AZD9272; alpha agonists, such as AGN XX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

Compounds of the instant invention are useful for the treatment of moderate to severe dementia of the Alzheimer's type alone or in combination with an NMDA receptor antagonist, such as memantine, or in combination with an acetylcholinesterase inhibitor (AChEI) such as donepezil.

Compounds of the instant invention are useful for the treatment of mild to moderate dementia of the Alzheimer's type alone or in combination with either galantamine, rivastigmine, or donepezil.

Compounds of the instant invention are useful for the treatment of dementia associated with Parkinson's disease alone or in combination with rivastigmine.

Compounds of the instant invention are useful for the treatment of motor fluctuations in patients with advanced Parkinson's disease alone or in combination with carbidopa and levodopa.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). A compound of the invention and an additional therapeutic agent may be present in fixed amounts (dosage amounts) in a single dosage unit (e.g., a capsule, a tablet and the like).

The α7 nAChR positive allosteric modulator (PAM) activity of the present compounds may be tested using assays known in the art. The α7 nAChR PAMs described herein have activities in an automated patch-clamp electrophysiology functional assay as described in the examples. The assay was performed using the IonFlux HT in a whole-cell, population patch configuration. See Golden et al. *Assay Drug Dev. Technol.* (2011) 9:608-619. The compounds were assessed for their ability to modulate the function of the human α7 nAChR stably expressed in a HEK cell line both in the presence, and in the absence of the natural α7 agonist acetylcholine. By performing a series of such measurements at different concentrations, the effective concentration of the α7 nAChR PAMs ($EC_{50}$) was determined. See Spencer et al. *Assay Drug Dev. Technol.* (2012) 10:313-324.

General Schemes

The compounds of the present invention can be prepared readily according to the following Schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

A number of compounds of the present invention may be prepared according to Scheme 1, in which acid 1.1 is first reacted with Ghosez's reagent and the resulting acid chloride treated with aminophenol 1.2 in 1,4-dioxane at elevated temperature to afford the corresponding amide. The resultant amide is then treated with TsOH at elevated temperature to give benzoxazole 1.3. Other coupling conditions, including reagents such as EDC and HOAt, and dehydrating reagents, such as phosphorous oxychloride, can be employed in these transformations. Other methods of forming the benzoxazole may also be employed, such as treating a solution of 1.1 and 1.2 with trimethylsilyl polyphosphate at elevated temperature. Additionally, the benzothiazole variant of 1.3 may be obtained by employing an aminothiophenol in place of aminophenol 1.2. Thioether 1.3 can be converted to the corresponding sulfonamide by treatment of 1.3 with DCDMH followed by reaction of the resultant sulfonyl chloride with ammonium hydroxide to afford product 1.4. If 1.4 is a mixture of enantiomers or diastereomers, the mixture may be separated by chiral chromatography. Alternatively, 1.1 and 1.2 may be employed as single enantiomers or diastereomers to obtain 1.4 enriched in a single enantiomer or diastereomer. Additionally, other heterocycles, such as thiazoles, can be utilized in place of the pyridine found in 1.1.

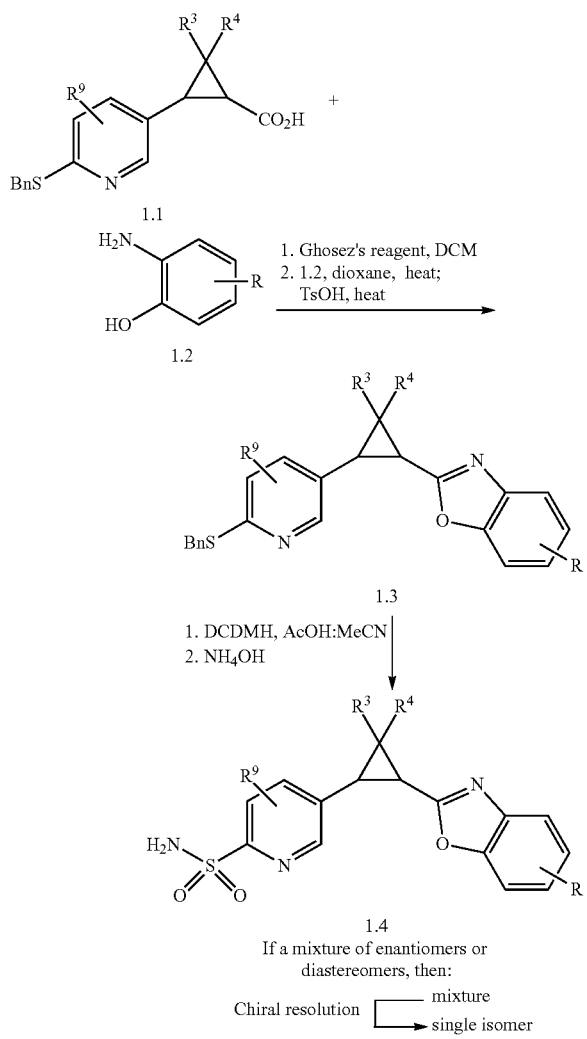

In addition, compounds in the present invention may be prepared according to Scheme 2, in which acid 2.1 is first reacted with Ghosez's reagent and the resulting acid chloride treated with acyl hydrazine 2.2 in the presence of triethylamine to afford the corresponding diacyl hydrazide. Other coupling reagents and conditions can be employed to effect this transformation. The resulting diacyl hydrazide is then treated with Lawesson's reagent and warmed to elevated temperature to afford thiadiazole product 2.3. Other thionating reagents, such $P_4S_{10}$ and hexamethyldisiloxane or hexamethyldisilathiane, and solvents, such as 1,4-dioxane, can be used for this transformation. Additionally, dehydrating reagents, such as PTSA, can be employed to complete the formation of the heterocycle after thionation. Further, other heterocycles, such as thiazoles, can be utilized in place of the six-membered heterocycle found in 2.1.

SCHEME 2

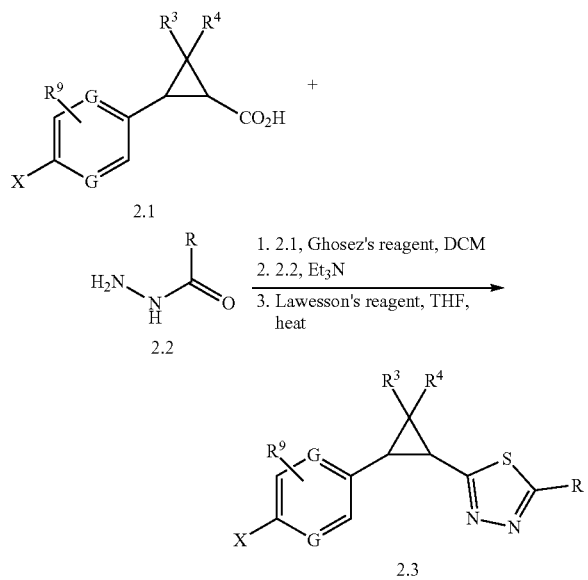

Many compounds of the present invention may be prepared according to Scheme 3, in which acid 2.1 is reacted with CDI in dioxane and then treated with amide oxime 3.1 in 1,4-dioxane at elevated temperature to afford oxadiazole 3.2. Other coupling reagents, such as EDC and HOAt, and solvents, such as toluene, can be employed in this transformation. If 3.2 is a mixture of enantiomers or diastereomers, the mixture may be separated by chiral chromatography. Alternatively, 2.1 and 3.1 may be employed as single enantiomers or diastereomers to obtain 3.2 enriched in a single enantiomer or diastereomer. Other methods of forming the oxadiazole may also be employed, such as reacting the corresponding ester of acid 2.1 with amide oxime 3.1 in the presence of potassium carbonate (or other bases) in ethanol (or other solvents) at elevated temperature or by reacting acid 2.1 with amide oxime 3.1 in the presence of EDC and HOAt followed either by adding T3P to the reaction mixture or by treating the isolated intermediate with TBAF in THF. Additionally, other heterocycles, such as thiazoles, can be utilized in place of the six-membered heterocycle found in 2.1.

SCHEME 3

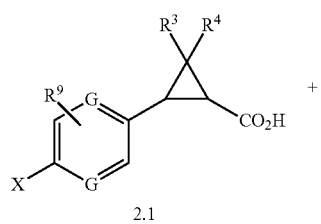

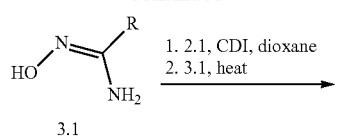

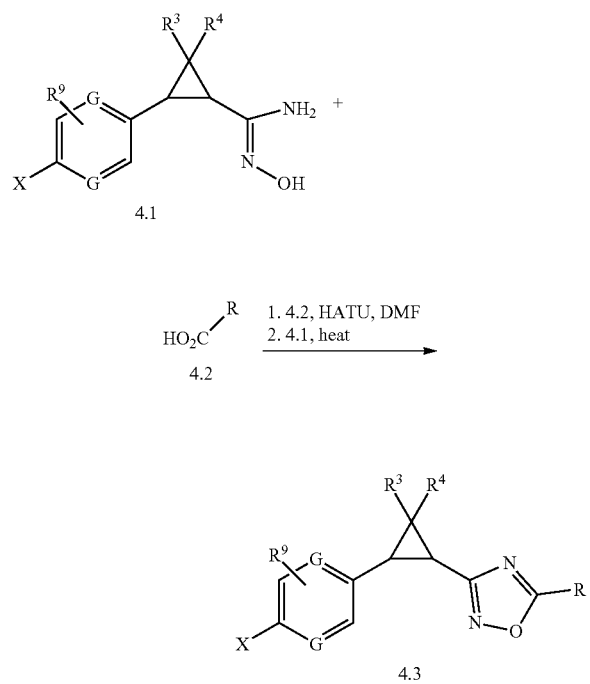

Additional compounds in the present invention may be prepared according to Scheme 4, in which the cyclopropane intermediate 4.1 now bears an amide oxime moiety. Acid 4.2 is reacted with HATU in the presence of Hunig's base in DMF and then treated with amide oxime 4.1 and warmed to elevated temperature to afford product 4.3.

SCHEME 4

Further compounds in the present invention may be prepared according to Scheme 5, in which acid 2.1 is reacted with HATU in DMF and then treated with amino ketone 5.1 followed by cyclodehydration of the resultant amide by treatment with POCl$_3$ to afford oxazole 5.2. Other coupling and dehydrating reagents and conditions can be employed to effect this transformation. Additionally, the corresponding thiazole may be prepared in place of the oxaxole by treating the product of step one with Lawesson's reagent in THF at elevated temperature instead of POCl$_3$.

SCHEME 5

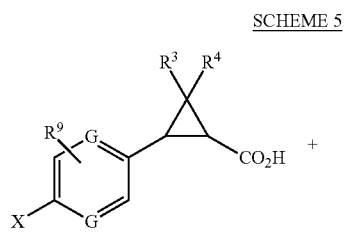

2.1

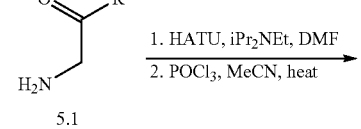

5.1

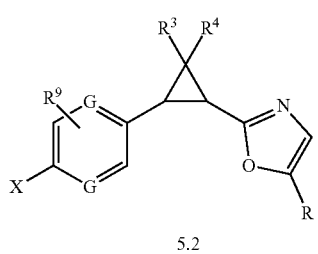

5.2

In addition, compounds in the present invention may be prepared according to Scheme 6, in which alkyne 6.1 participates in a [3+2] cycloaddition with a nitrile oxide (formed in situ by treatment of oxime 6.2 with PIFA) to afford isoxazole 6.3. Other nitrile oxide precursors, such as nitroalkanes or chlorooximes, activating reagents for oximes, such as PIDA, can be employed to effect this transformation. Further, a cyclopropyloxime may be utilized in place of cyclopropylalkyne 6.1 in this sequence and reacted with a suitable alkyne to afford the regioisomeric isoxazole.

SCHEME 6

6.1 + 6.2 → 6.3

Intermediates like 2.1 in the present invention may be prepared according to Scheme 7, in which heteroaryl bromide (or chloride, iodide, triflate, or tosylate) 7.1 is reacted with acrylate 7.2 under palladium-catalyzed conditions to afford product 7.3. A variety of different catalysts (including other metals such as nickel), ligands, bases, and solvents can be employed in this reaction. Heteroaryl cinnamate 7.3 is then cyclopropanated by reaction with the sulfur ylide generated by treatment of ylide precursor 7.4 with phenyllithium to afford product 7.5. Ester 7.5 is then converted to the corresponding acid 2.1 by treatment with TFA. If 2.1 is a mixture of enantiomers or diastereomers, the mixture may be separated by chiral chromatography. Additionally, a cyanoacrylate can be utilized in place of 7.2 in this sequence and the eventual cyclopropyl nitrile converted to amide oximes like 4.1 by treatment with hydroxylamine.

SCHEME 7

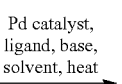

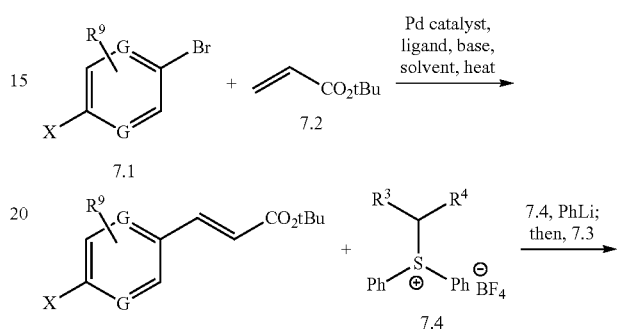

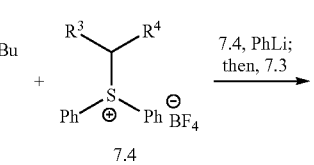

7.5

TFA ↓

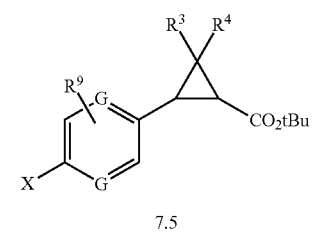

2.1
If a mixture of enantiomers or diastereomers, then:
Chiral resolution: mixture → single isomer Intermediates like 8.7 in the present invention may be prepared according to Scheme 8, which starts with Wittig olefination of heteroaryl aldehyde 8.1 by reaction with phosphorane 8.2 at elevated temperature to afford product 8.3. Heteroaryl cinnamate 8.3 is then cyclopropanated by reaction with the sulfur ylide generated by treatment of ylide precursor 7.4 with phenyllithium to afford product 8.4. Chlorothiazole 8.4 is then reacted with phenylmethanethiol in the presence of palladacycle Josiphos SL-J009-1 Pd G3 and Hunig's base at elevated temperature to afford product 8.5. Other palladium catalysts (such as tris(dibenzylideneacetone)dipalladium(0)), ligands (such as Xantphos), and bases (such as triethylamine) may be used in this transformation. Thioether 8.5 can then be treated with DCDMH followed by ammonium hydroxide to afford product 8.6. Ester 8.6 is then converted to acid 8.7 by treatment with TFA.

SCHEME 8

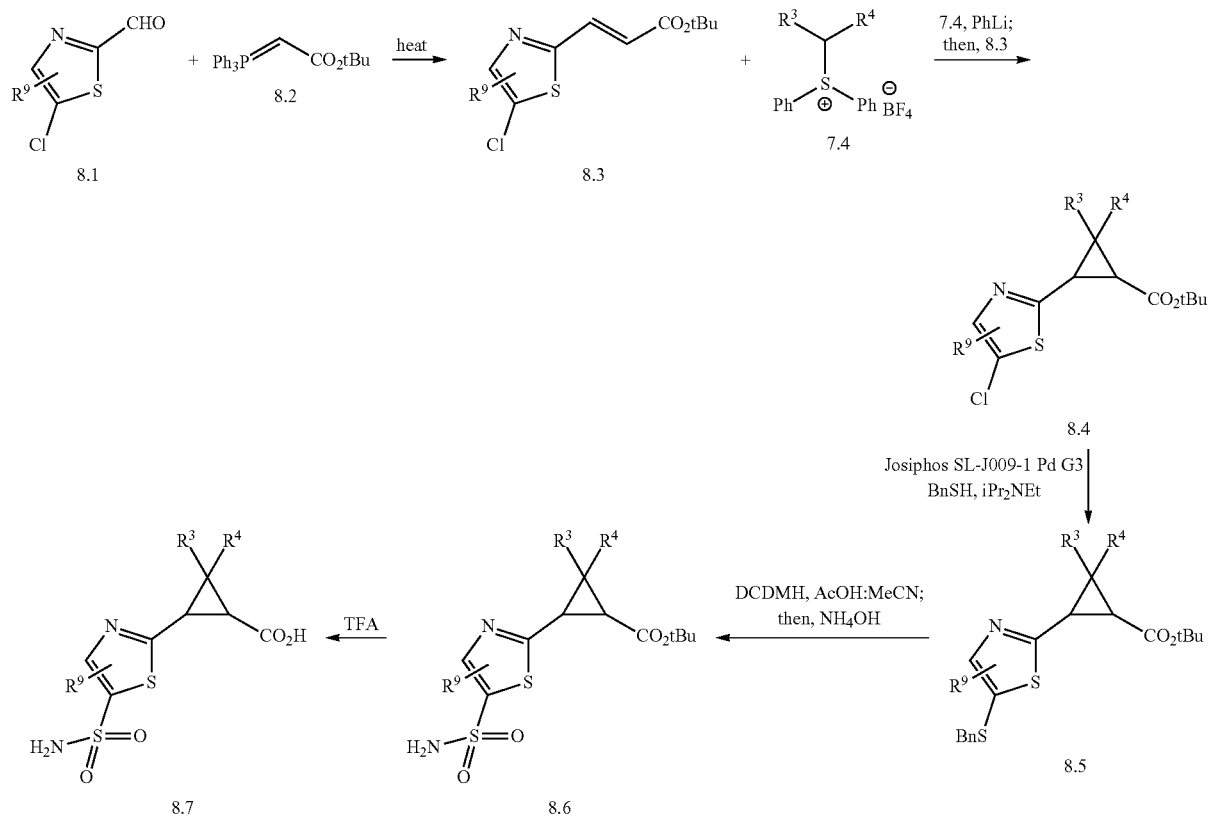

Further, intermediates like 9.3 in the present invention may be prepared according to Scheme 9, in which heteroaryl bromide (or chloride, iodide, triflate, or tosylate) 7.1 is reacted with cyclopropylboronate 9.1 under palladium-catalyzed conditions to afford product 9.2. A variety of different catalysts (including other metals such as nickel), ligands, bases, and solvents can be employed in this reaction. Ester 9.2 can then be saponified by treatment with sodium hydroxide to afford acid 9.3.

SCHEME 9

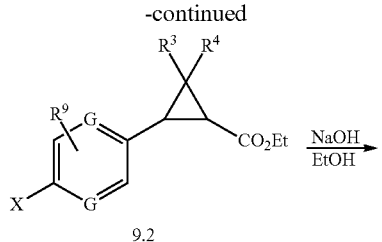

-continued

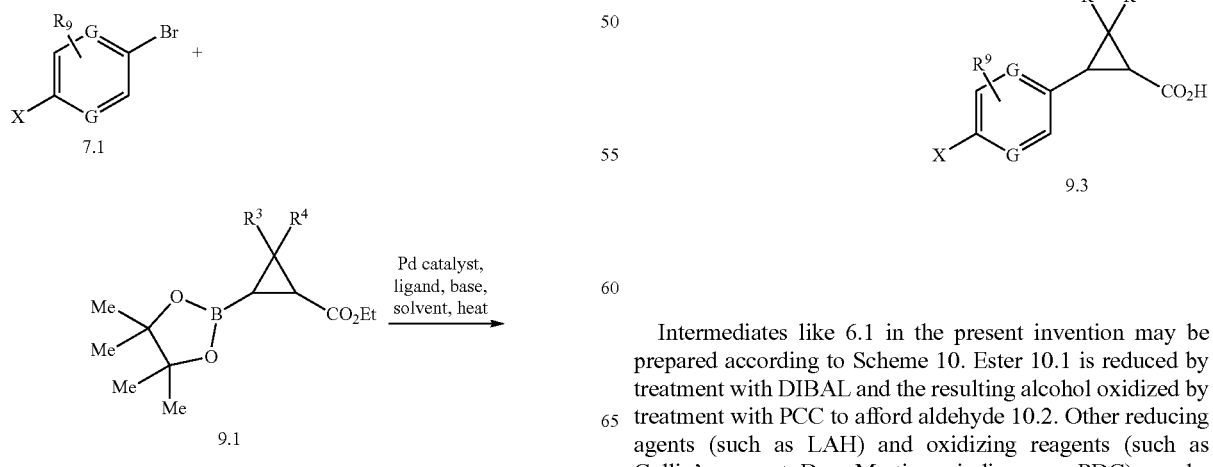

Intermediates like 6.1 in the present invention may be prepared according to Scheme 10. Ester 10.1 is reduced by treatment with DIBAL and the resulting alcohol oxidized by treatment with PCC to afford aldehyde 10.2. Other reducing agents (such as LAH) and oxidizing reagents (such as Collin's reagent, Dess-Martin periodinane, or PDC) may be used in these transformations. Aldehyde 10.2 can then be reacted with dimethyl (1-diazo-2-oxopropyl)phosphonate in the presence of potassium carbonate to afford alkyne 6.1. Other bases can be employed in this transformation.

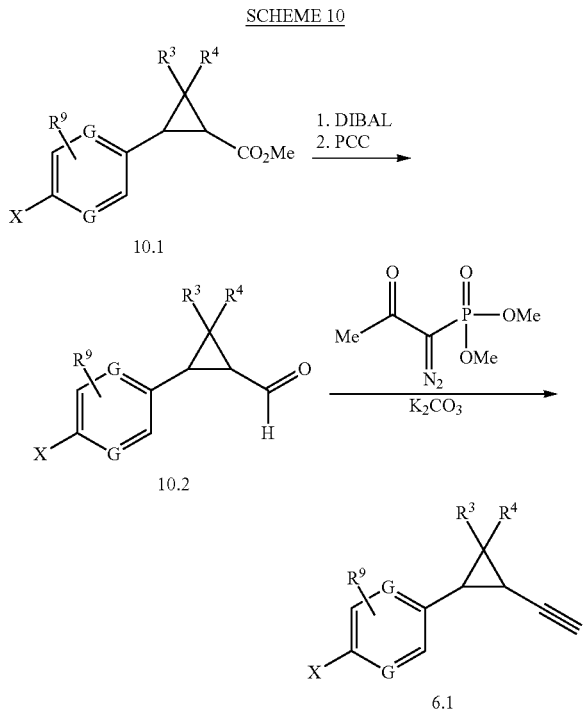

SCHEME 10

In some cases the order of carrying out the foregoing reaction schemes may be varied to facilitate the reaction or to avoid unwanted reaction products. Additionally, various protecting group strategies may be employed to facilitate the reaction or to avoid unwanted reaction products. The following examples are provided so that the invention might be more fully understood. These examples are illustrative only and should not be construed as limiting the invention in any way. Wherein a racemic mixture is produced, the enantiomers may be separated using SFC reverse or normal phase chiral resolution conditions either after isolation of the final product or at a suitable intermediate, followed by processing of the single isomers individually. It is understood that alternative methodologies may also be employed in the synthesis of these key intermediates. Asymmetric methodologies (e.g. chiral catalysis, auxiliaries) may be used where possible and appropriate. The exact choice of reagents, solvents, temperatures, and other reaction conditions, depends upon the nature of the intended product.

It is understood that the compounds and intermediates in the foregoing reaction schemes may be employed as synthetic intermediates in other schemes that involve similar intermediates to produce alternative compounds of the present invention.

In some cases the order of carrying out the foregoing reaction schemes may be varied to facilitate the reaction or to avoid unwanted reaction products. Additionally, various protecting group strategies familiar to one skilled in the art of organic synthesis may be employed to facilitate the reaction or to avoid unwanted reaction products.

In some cases the final product may be further modified, for example, by manipulation of substituents. These manipulations may include, but are not limited to, reduction, oxidation, alkylation, acylation, and hydrolysis reactions which are commonly known to those skilled in the art.

The following examples are provided so that the invention might be more fully understood. These examples are illustrative only and should not be construed as limiting the invention in any way. Wherein a racemic mixture is produced, the enantiomers may be separated using SFC reverse or normal phase chiral resolution conditions either after isolation of the final product or at a suitable intermediate, followed by processing of the single isomers individually. It is understood that alternative methodologies may also be employed in the synthesis of these key intermediates and examples. Asymmetric methodologies (e.g. chiral catalysis, auxiliaries) may be used where possible and appropriate. The exact choice of reagents, solvents, temperatures, and other reaction conditions, depends upon the nature of the intended product.

The following abbreviations are used throughout the text:

| | |
|---|---|
| Ac | Acetyl |
| AIBN | 2,2'-azobisisobutyronitrile |
| aq | Aqueous |
| Ar | Aryl |
| $B_2(Pin)_2$ | bis(pinacolato)diboron |
| BINAP | 2,2'-bis(diphenylphosphino)-1,1'-binaphthalene |
| Bn | Benzyl |
| Boc | tert-butoxycarbonyl |
| BOP | (benzotriazol-1-yloxy)tris(dimethylamino) phosphonium hexafluorophosphate |
| br | Broad |
| BSA | bovine serum albumin |
| Bu | Butyl |
| ca | circa (approximately) |
| CAN | ammonium cerium(IV) nitrate |
| Cbz | Carboxybenzyl |
| CDI | 1,1'-carbonyldiimidazole |
| d | Doublet |
| DABCO | diazabicyclo[2.2.2]octane |
| DAST | (diethylamino)sulfur trifluoride |
| dba | Dibenzylideneacetone |
| DBU | 1,8-diazabicyclo[5.4.0]undec-7-ene |
| DCDMH | 1,3-Dichloro-5,5-dimethylhydantoin; 1,3-dichloro-5,5-dimethylimidazolidine-2,4-dione |
| DCE | 1,2-dichloroethane |
| dd | doublet of doublets |
| DIBAL | diisobutylaluminum hydride |
| DIEA | N,N-diisopropylethylamine |
| DMA | N,N-dimethylacetamide |
| DMAP | 4-(dimethylamino)pyridine |
| DMEM: | Dulbecco's Modified Eagle Medium (High Glucose) |
| DMF | N,N-dimethylformamide |
| DMF—DMA | N,N-dimethylformamide dimethylacetal |
| DMPU | N,N'-dimethylpropyleneurea |
| DMSO | Dimethylsulfoxide |
| DPBF | 1,3-diphenylisobenzofuran |
| dppf | 1,1'-bis(diphenylphosphino)ferrocene |
| EDC | N-(3-dimethylaminopropyl)-N'-ethylcarbodiimide hydrochloride |
| EDTA | ethylenediaminetetraacetic acid |
| eq | Equivalents |
| ESI | electrospray ionization |
| Et | Ethyl |
| FBS | fetal bovine serum |
| Ghosez's reagent | 1-chloro-N,N,2-trimethylpropenylamine |
| h | Hours |
| HATU | O-(7-azabenzotriazol-1-yl)-N,N,N'N'-tetramethyluronium hexafluorophosphate |
| HEPES | N-(2-hydroxyethyl)piperazine-N'-(2-ethanesulfonic acid) |
| HMDS | Hexamethyldisilazane |
| HMTA | Hexamethylenetetramine |
| HOAt | 1-hydroxy-7-azabenzotriazole |
| HOBt | 1-hydroxybenzotriazole |
| HPLC | high performance liquid chromatography |

| | |
|---|---|
| Hz | Hertz |
| imid | Imidazole |
| i-Pr | Isopropyl |
| J | coupling constant |
| Josiphos SL-J009-1 | {(R)-1-[(Sp)-2-(Dicyclohexylphosphino)ferrocenyl] ethyldi-tert-butylphosphine}[2-(2'-amino-1,1'-biphenyl)]palladium(II) methanesulfonate |
| Pd G3 | |
| LAH | lithium aluminum hydride |
| LCMS | liquid chromatography-mass spectrometry |
| LDA | lithium diisopropylamide |
| m/z | mass to charge ratio |
| m | Multiplet |
| mCPBA | 3-chloroperbenzoic acid |
| Me | Methyl |
| min | Minutes |
| MP | macroporous polystyrene |
| Ms | Methanesulfonyl |
| MTBE | methyl tert-butyl ether |
| MW | molecular weight |
| NBS | N-bromosuccinimide |
| NHS | N-hydroxysuccinimide |
| n-BuLi | n-butyllithium |
| n-HexLi | n-hexyllithium |
| NMM | N-methyl morpholine |
| NMP | 1-methyl-2-pyrrolidinone |
| NMR | nuclear magnetic resonance |
| OAc | Acetate |
| p | Pentet |
| PBPB | pyridinium bromide perbromide |
| PBS | phosphate-buffered saline |
| PCC | pyridinium chlorochromate |
| PDC | pyridinium dichromate |
| Pd/C | palladium on carbon |
| Ph | Phenyl |
| PIDA | (diacetoxyiodo)benzene |
| PIFA | [bis(trifluoroacetoxy)iodo]benzene |
| PMBCl | 4-methoxybenzyl chloride |
| PS | polymer supported |
| psi | pounds per square inch |
| p-Ts | 4-toluenesulfonyl |
| PTSA | para-toluensulfonic acid |
| Py | Pyridyl |
| q | Quartet |
| rt | room temperature |
| s | Singlet |
| SEM | 2-trimethylsilyletrhoxymethyl |
| SEMCl | 2-trimethylsilyletrhoxymethyl chloride |
| SFC | supercritical fluid chromatography |
| SM | starting material |
| t | Triplet |
| T3P | 2,4,6-tripropyl-1,3,5,2,4,6-trioxatriphosphorinane-2,4,6-trioxide |
| TBAF | n-tetrabutylammonium fluoride |
| TBDPS | tert-butyldiphenylsilyl |
| TBDPSCl | tert-butyldiphenylsilyl chloride |
| t-Bu | tert-butyl |
| TCCA | trichloroisocyanuric acid |
| TEA | Trimethylamine |
| TFA | trifluoroacetic acid |
| Tf | Trifluoromethanesulfonyl |
| TCFH | tetramethylchloroformamidinium hexafluorophosphate |
| THF | Tetrahydrofuran |
| TMG | Tetramethylguanidine |
| TMSD | Trimethylsilyldiazomethane |
| trisyl | 2,4,6-triisopropylbenzenesulfonyl |
| V/V | volume to volume |
| X-Phos | 2-dicyclohexylphosphino-2',4',6'-triisopropylbiphenyl |

Intermediate 1

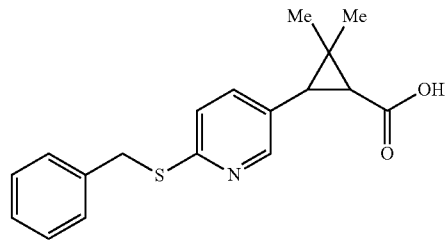 [SMILES: CC1(C)C(C(=O)O)C1c1ccc(SCc2ccccc2)nc1]

trans-3-[6-(Benzylsulfanyl)pyridin-3-yl]-2,2-dimethylcyclopropanecarboxylic Acid Step A: 2-(Benzylsulfanyl)-5-bromopyridine To a solution of 5-bromo-2-fluoropyridine (0.585 mL, 5.68 mmol) and phenylmethanethiol (0.867 mL, 7.39 mmol) in N,N-dimethylformamide (20 mL) at 0° C. was added NaH (60% dispersion in mineral oil, 0.295 g, 7.39 mmol) portionwise. Once gas evolution had ceased the reaction mixture was allowed to warm to ambient temperature and stir for 2 h. The reaction mixture was diluted with water and extracted with diethyl ether (3×). The combined organic extracts were dried (magnesium sulfate), filtered through a pad of Celite®, washing with diethyl ether, and the filtrate was concentrated under reduced pressure. The residue was purified by silica gel chromatography, eluting with a gradient of ethyl acetate:heptane—0:100 to 10:90 to afford the title compound. MS: m/z=280.0, 282.0 [M+H].

Step B: tert-Butyl 3-[6-(benzylsulfanyl)pyridin-3-yl]prop-2-enoate

To a mixture of 2-(benzylsulfanyl)-5-bromopyridine (500 mg, 1.79 mmol), tert-butyl acrylate (0.325 mL, 2.23 mmol), N,N-dicyclohexylmethylamine (0.764 mL, 3.57 mmol), and bis(tri-tert-butylphosphine)palladium(0) (91 mg, 0.18 mmol) in a sealable vial was added 1,4-dioxane (8 mL). The reaction mixture was deoxygenated, sealed, warmed to 100° C., and allowed to stir for 18 h. The reaction mixture was allowed to cool, diluted with ethyl acetate, filtered through a pad of Celite®, washing with ethyl acetate, and the filtrate was concentrated under reduced pressure. The residue was purified by silica gel chromatography, eluting with a gradient of ethyl acetate:heptane—0:100 to 10:90 to afford the title compound. MS: m/z=328.0 [M+H].

Step C: tert-Butyl trans-3-[6-(benzylsulfanyl)pyridin-3-yl]-2,2-dimethylcyclopropanecarboxylate To a solution of isopropyldiphenylsulfonium tetrafluoroborate (1.043 g, 3.298 mmol) in tetrahydrofuran (5 mL) at −78° C. was added a solution of phenyllithium in dibutyl ether (2 M, 1.65 mL, 3.30 mmol) slowly and the reaction mixture allowed to stir for 45 min. A solution of tert-butyl 3-[6-(benzylsulfanyl)pyridin-3-yl]prop-2-enoate (360 mg, 1.10 mmol) in tetrahydrofuran (2 mL) was added slowly. The reaction mixture was allowed to warm to ambient temperature and stir for 3 h. The reaction mixture was diluted with saturated aqueous ammonium chloride and extracted with ethyl acetate (3×). The combined organic extracts were dried (magnesium sulfate), filtered, and concentrated under reduced pressure. The residue was purified by silica gel chromatography, eluting with a gradient of ethyl acetate:heptane—0:100 to 10:90 to afford the title compound. MS: m/z=370.1 [M+H].

Step D: trans-3-[6-(Benzylsulfanyl)pyridin-3-yl]-2,2-dimethylcyclopropanecarboxylic Acid To a vessel containing tert-butyl trans-3-[6-(benzylsulfanyl)pyridin-3-yl]-2,2-dimethylcyclopropanecarboxylate (313 mg, 0.847 mmol) at ambient temperature was added trifluoroacetic acid (5 mL) and the reaction mixture allowed to stir for 1 h. The reaction mixture was concentrated under reduced pressure and the residue co-evaporated with toluene (2×5 mL) to afford the title compound in sufficient purity for use in the next step. MS: m/z=314.2 [M+H].

Intermediate 2

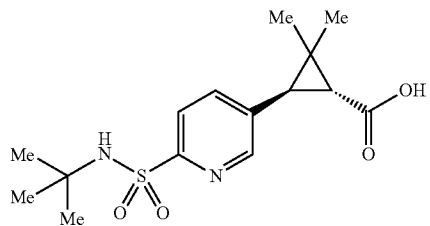 [SMILES: CC(C)(C)NS(=O)(=O)c1ccc([C@@H]2[C@@H](C(=O)O)C2(C)C)cn1]

(1R,3R)-3-[6-(tert-Butylsulfamoyl)pyridin-3-yl]-2,2-dimethylcyclopropanecarboxylic Acid Step A:
5-Bromo-N-tert-butylpyridine-2-sulfonamide To a solution of 2-methylpropan-2-amine (10.5 mL, 100 mmol) in dichloromethane (100 mL) at 0° C. was added a suspension of 5-bromopyridine-2-sulfonyl chloride (5 g, 19.49 mmol) in dichloromethane (25 mL) slowly and the reaction mixture allowed to stir for 3 h. The reaction mixture was concentrated under reduced pressure and the residue dissolved in ethyl acetate (50 mL) and sonicated for 2 min. Heptane (50 mL) was added and the reaction mixture sonicated for 2 min and filtered through a pad of silica gel washing with ethyl acetate:heptane—50:50. The filtrate was concentrated under reduced pressure to afford the title compound in sufficient purity for use in the next step. $^1$H NMR (600 MHz, CDCl$_3$) δ 8.74 (s, 1H), 8.11-7.95 (m, 1H), 7.91 (d, J=8.2 Hz, 1H), 4.89 (s, 1H), 1.23 (br s, 9H).

Step B: Ethyl 3-[6-(tert-butylsulfamoyl)pyridin-3-yl]prop-2-enoate

To a solution of 5-bromo-N-(tert-butyl)pyridine-2-sulfonamide (5.277 g, 18.00 mmol) in 1,4-dioxane (100 mL) was added ethyl acrylate (2.9 mL, 26.6 mmol) and N,N-dicyclohexylmethylamine (8 mL, 37.3 mmol). The reaction mixture was deoxygenated and chloro[(tri-tert-butylphosphine)-2-(2-aminobiphenyl)]palladium(II) (0.922 g, 1.80 mmol) was added. The reaction mixture was deoxygenated and warmed to 100° C. and allowed to stir for 18 h. The reaction mixture was allowed to cool, diluted with ethyl acetate, filtered through a pad of Celite®, washing with ethyl acetate, and the filtrate was concentrated under reduced pressure. The residue was purified by silica gel chromatography, eluting with a gradient of ethyl acetate:heptane—0:100 to 50:50. The product-containing fractions were combined and concentrated under reduced pressure. To the residue was added ethyl acetate:heptane—10:90 (50 mL) and the mixture sonicated for 2 min. The mixture was filtered and the solid washed with heptane to afford the title compound. MS: m/z=313.1 [M+H].

Step C: Ethyl trans-3-[6-(tert-butylsulfamoyl)pyridin-3-yl]-2,2-dimethylcyclopropanecarboxylate To a solution of isopropyldiphenylsulfonium tetrafluoroborate (15.79 g, 49.9 mmol) in tetrahydrofuran (100 mL) at −78° C. was added a solution of phenyllithium in dibutylether (1.9 M, 26.3 mL, 49.9 mmol) and the reaction mixture allowed to stir for 2 h. A solution of ethyl trans-3-[6-(tert-butylsulfamoyl)pyridin-3-yl]prop-2-enoate (5.2 g, 16.65 mmol) in tetrahydrofuran (20 mL) was added slowly. The reaction mixture was allowed to warm to ambient temperature and stir for 2 h. The reaction mixture was diluted with saturated aqueous ammonium chloride and extracted with ethyl acetate (3×). The combined organic extracts were dried (magnesium sulfate), filtered, and concentrated under reduced pressure. The residue was purified by silica gel chromatography, eluting with a gradient of ethyl acetate:heptane—0:100 to 50:50. The product containing fractions were combined and concentrated under reduced pressure and the residue triturated with diethyl ether, filtered, washed with diethyl ether to afford the title compound. MS: m/z=355.2 [M+H].

Step D: Ethyl (1R,3R)-3-[6-(tert-butylsulfamoyl)pyridin-3-yl]-2,2-dimethylcyclopropanecarboxylate Ethyl trans-3-[6-(tert-butylsulfamoyl)pyridin-3-yl]-2,2-dimethylcyclopropanecarboxylate was resolved by SFC, utilizing a Chromega Chiral CC4 column, eluting with methanol:carbon dioxide:diethylamine—30:70:0.1. The first major peak to elute was ethyl (1S,3S)-3-[6-(tert-butylsulfamoyl)pyridin-3-yl]-2,2-dimethylcyclopropanecarboxylate and the second major peak to elute was ethyl (1R,3R)-3-[6-(tert-butylsulfamoyl)pyridin-3-yl]-2,2-dimethylcyclopropanecarboxylate, the title compound. $^1$H NMR (600 MHz, CDCl$_3$) δ 8.52 (d, J=1.5 Hz, 1H), 7.94 (d, J=8.0 Hz, 1H), 7.63 (dd, J=8.1, 2.1 Hz, 1H), 4.92 (s, 1H), 4.20 (qd, J=7.1, 1.8 Hz, 2H), 2.70 (d, J=5.9 Hz, 1H), 2.06 (d, J=5.9 Hz, 1H), 1.41 (s, 3H), 1.31 (t, J=7.1 Hz, 3H), 1.20 (s, 9H), 0.94 (s, 3H).

Step E: (1R,3R)-3-[6-(tert-Butylsulfamoyl)pyridin-3-yl]-2,2-dimethylcyclopropanecarboxylic Acid To a solution of ethyl (1R,3R)-3-[6-(tert-butylsulfamoyl)pyridin-3-yl]-2,2-dimethylcyclopropanecarboxylate (982 mg, 2.77 mmol) in ethanol (15 mL) was added an aqueous solution of sodium hydroxide (2 M, 4.5 mL, 9.00 mmol) and the reaction mixture warmed to reflux and allowed to stir for 18 h. The reaction mixture was cooled and concentrated under reduced pressure. The residue was taken up in a small amount of water and an aqueous solution of HCl (1 M, 9 mL, 9 mmol) was added. The mixture was filtered and the solid washed with water and dried under reduced pressure to afford the title compound. MS: m/z=327.1 [M+H].

Intermediate 3

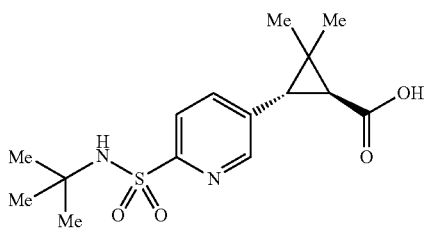 [SMILES: CC(C)(C)NS(=O)(=O)c1ccc([C@H]2[C@H](C(=O)O)C2(C)C)cn1]

(1S,3S)-3-[6-(tert-Butylsulfamoyl)pyridin-3-yl]-2,2-dimethylcyclopropanecarboxylic Acid Essentially following the procedures described in Intermediate 2, but using ethyl (1S,3S)-3-[6-(tert-butylsulfamoyl)pyri din-3-yl]-2,2-dimethylcyclopropanecarboxylate (described in Intermediate 2) in place of ethyl (1R,3R)-3-[6-(tert-butylsulfamoyl)pyridin-3-yl]-2,2-dimethylcyclopropanecarboxylate, the title compound was obtained. MS: m/z=327.1 [M+H].

Intermediate 4

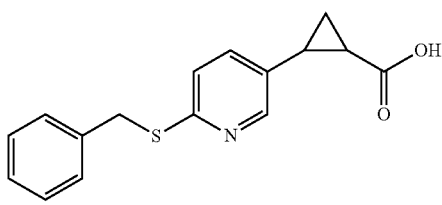 [SMILES: O=C(O)C1CC1c1ccc(SCc2ccccc2)nc1]

trans-2-[6-(Benzylsulfanyl)pyridin-3-yl]cyclopropanecarboxylic Acid

Step A: Ethyl trans-2-[6-(benzylsulfanyl)pyridin-3-yl]cyclopropanecarboxylate

To a deoxygenated solution of 2-(benzylthio)-5-bromopyridine (1.29 g, 4.60 mmol) and ethyl trans-2-(4,4,5,5-tetramethyl-1,3,2-dioxaborolan-2-yl)cyclopropanecarboxylate (1.44 g, 6.00 mmol) in toluene (20 mL) was added cesium carbonate (3.00 g, 9.21 mmol), palladium(II) acetate (0.103 g, 0.460 mmol), di(1-adamantyl)-N-butylphosphine (0.330 g, 0.921 mmol), and water (2.0 mL). The reaction mixture was deoxygenated and warmed to 100° C. and allowed to stir for 18 h. The reaction mixture was allowed to cool then diluted with ethyl acetate, filtered through a pad of Celite® washing with ethyl acetate, and concentrated under reduced pressure. The residue was purified by silica gel chromatography, eluting with a gradient of ethyl acetate:heptane—0:100 to 25:75 to afford the title compound. MS: m/z=314.3 [M+H].

Step B: trans-2-[6-(Benzylsulfanyl)pyridin-3-yl]cyclopropanecarboxylic Acid

To a solution of ethyl trans-2-[6-(benzylsulfanyl)pyridin-3-yl]cyclopropanecarboxylate (1.19 g, 3.80 mmol) in ethanol (20 mL) at ambient temperature was added an aqueous solution of sodium hydroxide (2 M, 5.70 mL, 11.4 mmol) and the reaction mixture allowed to stir for 18 h. The reaction mixture was concentrated under reduced pressure and an aqueous solution of HCl (12.1 M, 0.935 mL, 11.3 mmol) was added slowly. The reaction mixture was allowed to stir for 10 min and then concentrated under reduced pressure. The residue was dissolved in ethyl acetate and sonicated for 2 min. The resulting mixture was filtered through a pad of Celite®, washing with ethyl acetate, and concentrated under reduced pressure to afford the title compound. MS: m/z=286.1 [M+H].

Intermediate 5

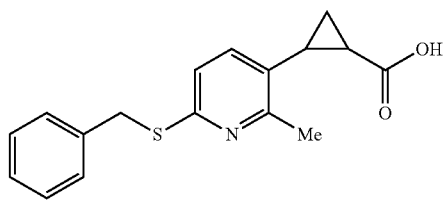 [SMILES: Cc1nc(SCc2ccccc2)ccc1C1CC1C(=O)O]

2-[6-(Benzylsulfanyl)-2-methylpyridin-3-yl]cyclopropanecarboxylic Acid

Step A: 6-(Benzyl sulfanyl)-3-bromo-2-methylpyridine

To a solution of 3-bromo-6-fluoro-2-methylpyridine (250 mg, 1.32 mmol) in N,N-dimethylformamide (5 mL) at ambient temperature was added phenylmethanethiol (0.201 mL, 1.71 mmol) and sodium hydride (60% dispersion in mineral oil, 69 mg, 1.7 mmol) sequentially and the reaction mixture allowed to stir for 18 h. The reaction mixture was concentrated under reduced pressure and the residue purified by silica gel chromatography, eluting with a gradient of ethyl acetate:heptane—0:100 to 10:90 to afford the title compound. MS: m/z=294.0, 296.0 [M+H].

Step B: Ethyl 2-[6-(benzylsulfanyl)-2-methylpyridin-3-yl]cyclopropanecarboxylate To a sealable vial containing 6-(benzylsulfanyl)-3-bromo-2-methylpyridine (367 mg, 1.25 mmol) at ambient temperature was added ethyl trans-2-(4,4,5,5-tetramethyl-1,3,2-dioxaborolan-2-yl)cyclopropanecarboxylate (389 mg, 1.62 mmol), palladium(II) acetate (28.0 mg, 0.125 mmol), di(1-adamantyl)-N-butylphosphine (89 mg, 0.249 mmol), toluene (5 mL), and an aqueous solution of cesium carbonate (5 M, 0.499 mL, 2.50 mmol) sequentially. The reaction mixture was deoxygenated, the vessel sealed, and the reaction mixture warmed to 100° C. and allowed to stir for 18 h. The reaction mixture was allowed to cool, diluted with ethyl acetate, filtered through a pad of Celite®, washing with ethyl acetate, and concentrated under reduced pressure. The residue was purified by silica gel chromatography, eluting with a gradient of ethyl acetate:heptane—0:100 to 20:80 to afford the title compound. MS: m/z=329.1 [M+H].

Step C: trans-2-[6-(Benzylsulfanyl)-2-methylpyridin-3-yl]cyclopropanecarboxylic Acid To a solution of ethyl trans-2-[6-(benzylsulfanyl)-2-methylpyridin-3-yl]cyclopropanecarboxylate (286 mg, 0.873 mmol) in ethanol (5 mL) at ambient temperature was added an aqueous solution of sodium hydroxide (2 M, 1.31 mL, 2.62 mmol) and the reaction mixture allowed to stir for 18 h. The reaction mixture was concentrated under reduced pressure, an aqueous solution of HCl (12.1 M, 0.215 mL, 2.60 mmol) was added, and the mixture allowed to stir for 10 min. The mixture was diluted with ethyl acetate, stirred for 10 min, filtered through a pad of silica gel eluting with ethyl acetate, and the filtrate concentrated under reduced pressure to afford the title compound. MS: m/z=300.1 [M+H].

Intermediate 6

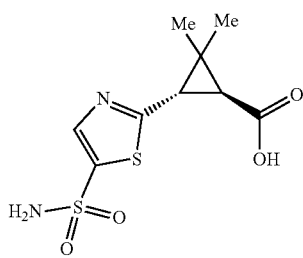 [SMILES: CC1(C)[C@@H](C(=O)O)[C@@H]1c1ncc(S(N)(=O)=O)s1]

(1S,3S)-2,2-Dimethyl-3-(5-sulfamoyl-1,3-thiazol-2-yl)cyclopropanecarboxylic Acid Step A: tert-Butyl 3-(5-chloro-1,3-thiazol-2-yl)prop-2-enoate To a solution of 5-chlorothiazole-2-carbaldehyde (5 g, 33.9 mmol) in toluene (150 mL) was added tert-butyl 2-(triphenylphosphoranylidene)acetate (19.13 g, 50.8 mmol) portionwise and the reaction mixture warmed to 80° C. and allowed to stir for 18 h. The reaction mixture was cooled then concentrated under reduced pressure. The residue was dissolved in diethyl ether (100 mL), the mixture filtered, washing with diethyl ether, and the filtrate was concentrated under reduced pressure. The residue was dissolved in diethyl ether:heptane (5:95), filtered, washing with heptane, and the filtrate was concentrated under reduced pressure. The residue was purified by silica gel chromatography, eluting with a gradient of ethyl acetate:heptane—0:100 to 10:90 to afford the title compound. MS: m/z=246.1 [M+H].

Step B: tert-Butyl trans-3-(5-chloro-1,3-thiazol-2-yl)-2,2-dimethylcyclopropanecarboxylate To a mixture of isopropyldiphenylsulfonium tetrafluoroborate (10.3 g, 32.6 mmol) in tetrahydrofuran (80 mL) at −78° C. was added a solution of phenyllithium in dibutyl ether (2 M, 17.2 mL, 34.4 mmol) slowly and the reaction mixture allowed to stir for 90 min. A solution of tert-butyl (5-chloro-1,3-thiazol-2-yl)prop-2-enoate (4 g, 16.3 mmol) in tetrahydrofuran (20 mL) was added slowly and the reaction mixture allowed to warm to ambient temperature and stir for 3 h. The reaction mixture was diluted with saturated aqueous ammonium chloride and extracted with dichloromethane (3×). The combined organic extracts were dried (magnesium sulfate), filtered, and concentrated under reduced pressure. The residue was dissolved in dichloromethane:heptane (25:75, 100 mL), filtered (washing with dichloromethane:heptane (25:75)), and the filtrate was concentrated under reduced pressure. The residue was purified by silica gel chromatography, eluting with a gradient of ethyl acetate:heptane—0:100 to 10:90 to afford the title compound. MS: m/z=288.1 [M+H].

Step C: tert-Butyl trans-3-[5-(benzylsulfanyl)-1,3-thiazol-2-yl]-2,2-dimethylcyclopropanecarboxylate To a solution of tert-butyl trans-3-(5-chloro-1,3-thiazol-2-yl)-2,2-dimethylcyclopropanecarboxylate (3.66 g, 12.7 mmol) in 1,4-dioxane (60 mL) in a sealable vessel was added diisopropylethylamine (4.5 mL, 25.8 mmol) and phenylmethanethiol (1.9 mL, 16.2 mmol) and the reaction mixture was deoxygenated. {(R)-1-[(Sp)-2-(Dicyclohexylphosphino)ferrocenyl]ethyldi-tert-butylphosphine}[2-(2'-amino-1,1'-biphenyl)]palladium(II) methanesulfonate (0.588 g, 0.636 mmol) was added, the reaction mixture deoxygenated, the vessel sealed, and the reaction mixture warmed to 110° C. and allowed to stir for 18 h. The reaction mixture was cooled, diluted with ethyl acetate, filtered through a pad of Celite®, washing with ethyl acetate, and the filtrate was concentrated under reduced pressure. The residue was purified by silica gel chromatography, eluting with a gradient of ethyl acetate:heptane—0:100 to 10:90 to afford the title compound. MS: m/z=376.3 [M+H].

Step D: tert-Butyl trans-2,2-dimethyl-3-(5-sulfamoyl-1,3-thiazol-2-yl)cyclopropanecarboxylate To a solution of tert-butyl trans-3-[5-(benzylsulfanyl)-1,3-thiazol-2-yl]-2,2-dimethylcyclopropanecarboxylate (4.91 g, 13.1 mmol) in acetonitrile (60 mL) at 0° C. was added acetic acid (2.250 mL) and water (1.500 mL) and the reaction mixture allowed to stir for 1 min. 1,3-Dichloro-5,5-dimethylimidazolidine-2,4-dione (5.15 g, 26.1 mmol) was added and the reaction mixture allowed to stir for 60 min. Ammonium hydroxide (19 mL, 137 mmol) was added, the reaction mixture allowed to warm to ambient temperature and stir for 2 h. The reaction mixture was diluted with water and extracted with ethyl acetate (3×). The combined organic extracts were dried (magnesium sulfate), filtered, and concentrated under reduced pressure. The residue was purified by silica gel chromatography, eluting with a gradient of ethyl acetate:heptane—0:100 to 10:90 to afford the title compound. MS: m/z=333.1 [M+H].

Step E: tert-Butyl (1S,3S)-2,2-dimethyl-3-(5-sulfamoyl-1,3-thiazol-2-yl)cyclopropanecarboxylate Racemic tert-butyl trans-2,2-dimethyl-3-(5-sulfamoyl-1,3-thiazol-2-yl)cyclopropanecarboxylate was resolved by SFC, utilizing a ChiralPak AD-H column, eluting with 2-propanol:carbon dioxide:diethylamine—15:85:0.1. The first major peak to elute was tert-butyl (1S,3S)-2,2-dimethyl-3-(5-sulfamoyl-1,3-thiazol-2-yl)cyclopropanecarboxylate, the title compound, and the second major peak to elute was tert-butyl (1R,3R)-2,2-dimethyl-3-(5-sulfamoyl-1,3-thiazol-2-yl)cyclopropanecarboxylate. $^1$H NMR (500 MHz, CDCl$_3$) δ 8.08 (s, 1H), 5.13 (s, 2H), 2.79 (d, J=5.6 Hz, 1H), 2.45 (d, J=5.6 Hz, 1H), 1.48 (s, 9H), 1.36 (s, 3H), 1.18 (s, 3H).

Step F: (1S,3S)-2,2-Dimethyl-3-(5-sulfamoyl-1,3-thiazol-2-yl)cyclopropanecarboxylic Acid To a vessel containing tert-butyl (1S,3S)-2,2-dimethyl-3-(5-sulfamoyl-1,3-thiazol-2-yl)cyclopropanecarboxylate (100 mg, 0.301 mmol) at ambient temperature was added trifluoroacetic acid (2 mL) and the reaction mixture allowed to stir for 3 h. The reaction mixture was concentrated under reduced pressure and the residue co-evaporated with dichloromethane:heptane (1:1, 3×) to afford the title compound. MS: m/z=277.0 [M+H].

Intermediate 7

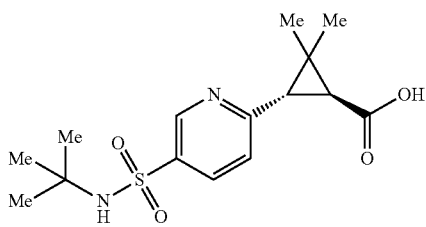 [SMILES: CC(C)(C)NS(=O)(=O)c1ccc([C@H]2[C@H](C(=O)O)C2(C)C)nc1]

(1S,3S)-3-[5-(tert-Butylsulfamoyl)pyridin-2-yl]-2,2-dimethylcyclopropanecarboxylic Acid Step A: N-tert-Butyl-6-chloropyridine-3-sulfonamide To a solution of 2-methylpropan-2-amine (12.4 mL, 118 mmol) in dichloromethane (100 mL) at 0° C. was added a suspension of 6-chloropyridine-3-sulfonyl chloride (5 g, 23.58 mmol) in dichloromethane (25 mL) slowly and the reaction mixture allowed to stir for 3 h. The reaction mixture was concentrated under reduced pressure and the residue dissolved in ethyl acetate (50 mL) and sonicated for 2 min. Heptane (50 mL) was added and the mixture sonicated for 2 min and filtered through a pad of silica gel (washing with ethyl acetate:heptane, 1:1). The filtrate was concentrated under reduced pressure to afford the title compound in sufficient purity for use in the next step. MS: m/z=249.0 [M+H].

Step B: Ethyl 3-[5-(tert-butylsulfamoyl)pyridin-2-yl]prop-2-enoate

To a solution of N-tert-butyl-6-chloropyridine-3-sulfonamide (5.47 g, 22.0 mmol) in toluene (100 mL) and water (10.00 mL) was added ethyl 3-(4,4,5,5-tetramethyl-1,3,2-dioxaborolan-2-yl)acrylate (6.46 g, 28.6 mmol) and cesium carbonate (14.33 g, 44.0 mmol). The reaction mixture was deoxygenated and chloro(2-dicyclohexylphosphino-2',4',6'-triisopropyl-1,1'-biphenyl)[2-(2'-amino-1,1'-biphenyl)]palladium(II) (1.730 g, 2.199 mmol) was added. The reaction mixture was deoxygenated, warmed to 100° C. and allowed to stir for 18 h. The reaction mixture was allowed to cool then diluted with water and extracted with ethyl acetate (3×). The combined organic extracts were dried (magnesium sulfate), filtered, and concentrated under reduced pressure. The residue was purified by silica gel chromatography, eluting with a gradient of ethyl acetate:heptane—0:100 to 50:50 to afford the title compound. MS: m/z=313.1 [M+H].

Step C: Ethyl trans-3-[5-(tert-butylsulfamoyl)pyridin-2-yl]-2,2-dimethylcyclopropanecarboxylate To a mixture of isopropyldiphenylsulfonium tetrafluoroborate (9.44 g, 29.9 mmol) in tetrahydrofuran (80 mL) at −78° C. was added a solution of phenyllithium in dibutyl ether (1.9 M, 15.7 mL, 29.9 mmol) slowly and the reaction mixture allowed to stir for 2 h. A solution of ethyl 3-[5-(tert-butylsulfamoyl)pyridin-2-yl]prop-2-enoate (3.11 g, 9.96 mmol) in tetrahydrofuran (20 mL) was added slowly and the reaction mixture allowed to warm to ambient temperature and stir for 2 h. The reaction mixture was diluted with saturated aqueous ammonium chloride and extracted with ethyl acetate (3×). The combined organic extracts were dried (magnesium sulfate), filtered through a pad of silica gel, washing with ethyl acetate, and the filtrate was concentrated under reduced pressure. The residue was purified by silica gel chromatography, eluting with a gradient of ethyl acetate:heptane—0:100 to 50:50 to afford the title compound. MS: m/z=355.2 [M+H].

Step D: trans-3-[5-(tert-Butylsulfamoyl)pyridin-2-yl]-2,2-dimethylcyclopropanecarboxylic Acid To a solution of ethyl trans-3-[5-(tert-butylsulfamoyl)pyridin-2-yl]-2,2-dimethylcyclopropanecarboxylate (3.2 g, 9.0 mmol) in ethanol (50 mL) was added an aqueous solution of sodium hydroxide (2 M, 15 mL, 30.0 mmol) and the reaction mixture warmed to 80° C. and allowed to stir for 5 h. The reaction mixture was allowed to cool and concentrated under reduced pressure. The residue was dissolved in water, the pH adjusted to 3, and the mixture extracted with dichloromethane (3×). The combined organic extracts were filtered through a pad of Celite®, washing with dichloromethane then concentrated under reduced pressure to afford the title compound. MS: m/z=327.1 [M+H].

Step E: (1S,3S)-3-[5-(tert-Butylsulfamoyl)pyridin-2-yl]-2,2-dimethylcyclopropanecarboxylic Acid Racemic trans-3-[5-(tert-butylsulfamoyl)pyridin-2-yl]-2,2-dimethylcyclopropanecarboxylic acid was resolved by SFC, utilizing a ChiralPak AD column, eluting with methanol:carbon dioxide:trifluoroacetic acid—40:60:0.1. The first major peak to elute was (1S,3S)-3-[5-(tert-butylsulfamoyl)pyridin-2-yl]-2,2-dimethylcyclopropanecarboxylic acid, the title compound, and the second major peak to elute was (1R,3R)-3-[5-(tert-butylsulfamoyl)pyridin-2-yl]-2,2-dimethylcyclopropanecarboxylic acid. MS: m/z=327.1 [M+H].

Intermediate 8

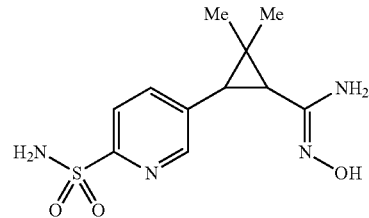 [SMILES: CC1(C)C(/C(N)=N/O)C1c1ccc(S(N)(=O)=O)nc1]

trans-N'-Hydroxy-2,2-dimethyl-3-(6-sulfamoylpyridin-3-yl)cyclopropanecarboximidamide Step A: 3-[6-(Benzylsulfanyl)pyridin-3-yl]prop-2-enenitrile To a solution of 2-(benzylsulfanyl)-5-bromopyridine (5.00 g, 17.9 mmol) in 1,4-dioxane (30 mL) was added N-cyclohexyl-N-methylcyclohexanamine (6.97 g, 35.7 mmol), acrylonitrile (1.89 g, 35.7 mmol), and bis(tri-tert-butylphosphine)palladium(0) (0.27 g, 0.54 mmol). The reaction mixture was warmed to 100° C. and allowed to stir for 4 h. The reaction mixture was allowed to cool then concentrated under reduced pressure. The residue was purified by silica gel chromatography, eluting with ethyl acetate:petroleum ether—25:75 to afford the title compound. MS: m/z=253.1 [M+H].

Step B: trans-3-[6-(Benzylsulfanyl)pyridin-3-yl]-2,2-dimethylcyclopropanecarbonitrile To a mixture of isopropyldiphenylsulfonium tetrafluoroborate (6.39 g, 20.2 mmol) and tetrahydrofuran (20 mL) at −78° C. was added phenyllithium in dibutyl ether (1.9 M, 10.64 mL, 20.21 mmol) slowly and the reaction mixture allowed to stir for 1 h. A solution of ethyl 3-[6-(benzylsulfanyl)pyridin-3-yl]prop-2-enenitrile (1.7 g, 6.74 mmol) in tetrahydrofuran (5 mL) was added slowly and the reaction mixture allowed to warm to ambient temperature and stir for 1 h. The reaction mixture was diluted with water and ethyl acetate and the aqueous layer extracted with ethyl acetate. The combined organic extracts were washed with saturated aqueous sodium chloride, dried (magnesium sulfate) and concentrated under reduced pressure. The residue was purified by silica gel chromatography, eluting with ethyl acetate:petroleum ether—12:88 to afford the title compound. MS: m/z=295.1 [M+H].

Step C: 5-(trans-3-Cyano-2,2-dimethylcyclopropyl)pyridine-2-sulfonamide

To a solution of trans-3-[6-(benzylsulfanyl)pyridin-3-yl]-2,2-dimethylcyclopropanecarbonitrile (500 mg, 1.70 mmol) in a mixture of acetonitrile (6 mL), acetic acid (0.15 mL), and water (0.15 mL) at 0° C. was added 1,3-dichloro-5,5-dimethylimidazolidine-2,4-dione (502 mg, 2.55 mmol) and the reaction mixture allowed to stir for 30 min. Ammonium hydroxide (28%, 4.72 mL, 34.0 mmol) was added and the reaction mixture allowed to warm to ambient temperature and stir for 30 min. The reaction mixture was diluted with water and ethyl acetate and the aqueous layer extracted with ethyl acetate. The combined organic extracts were washed with saturated aqueous sodium chloride, dried (magnesium sulfate) and concentrated under reduced pressure. The residue was purified by silica gel chromatography, eluting with a gradient of ethyl acetate:heptane—0:100 to 50:50 to afford the title compound. MS: m/z=252.0 [M+H].

Step D: trans-N'-Hydroxy-2,2-dimethyl-3-(6-sulfamoylpyridin-3-yl)cyclopropanecarboximidamide To a solution of 5-(trans-3-cyano-2,2-dimethylcyclopropyl)pyridine-2-sulfonamide (550 mg, 2.20 mmol) in ethanol (10 mL) was added triethylamine (1.23 mL, 8.79 mmol) and hydroxylamine hydrochloride (305 mg, 4.39 mmol). The reaction mixture was warmed to 85° C. and allowed to stir for 6 h. The reaction mixture was allowed to cool and concentrated under reduced pressure to afford the title compound in sufficient purity for use in the next step. MS: m/z=285.1 [M+H].

Intermediate 9

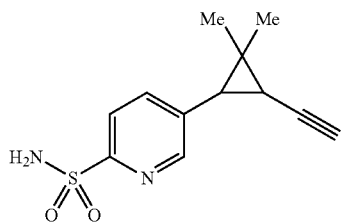 [SMILES: C#CC1C(c2ccc(S(N)(=O)=O)nc2)C1(C)C]

5-(trans-3-Ethynyl-2,2-dimethylcyclopropyl)pyridine-2-sulfonamide

Step A: Methyl trans-2,2-dimethyl-3-(6-sulfamoylpyridin-3-yl)cyclopropanecarboxylate To a vessel containing 5-(trans-3-cyano-2,2-dimethylcyclopropyl)pyridine-2-sulfonamide (1.2 g, 4.78 mmol) was added a solution of HCl in methanol (4 M, 10 mL, 40 mmol) and the reaction mixture warmed to 80° C. and allowed to stir for 48 h. The reaction mixture was concentrated under reduced pressure to afford the title compound in sufficient purity for use in the next step. MS: m/z=285.0 [M+H]

Step B: 5-[trans-3-(Hydroxymethyl)-2,2-dimethylcyclopropyl]pyridine-2-sulfonamide To a solution of methyl trans-2,2-dimethyl-3-(6-sulfamoylpyridin-3-yl)cyclopropanecarboxylate (1.3 g, 4.4 mmol) in tetrahydrofuran (15 mL) at 0° C. was added a solution of diisobutylaluminum hydride in toluene (1 M, 26.1 mL, 26.1 mmol) and the reaction mixture allowed to stir for 1 h. Water (5 mL) was added, the mixture filtered, and the filtrate concentrated under reduced pressure to afford the title compound in sufficient purity for use in the next step. MS: m/z=256.8 [M+H].

Step C: 5-(trans-3-Formyl-2,2-dimethylcyclopropyl)pyridine-2-sulfonamide

To a solution of 5-[trans-3-(hydroxymethyl)-2,2-dimethylcyclopropyl]pyridine-2-sulfonamide (400 mg, 1.56 mmol) in tetrahydrofuran (5 mL) at 0° C. was added PCC (673 mg, 3.12 mmol) and the reaction mixture allowed to stir for 10 min. The reaction mixture was concentrated under reduced pressure and the residue purified by silica gel chromatography, eluting with a gradient of ethyl acetate:petroleum ether—20:80 to 50:50 to afford the title compound. MS: m/z=255.1 [M+H].

Step D: 5-(trans-3-Ethynyl-2,2-dimethylcyclopropyl)pyridine-2-sulfonamide

To a solution of 5-(trans-3-formyl-2,2-dimethylcyclopropyl)pyridine-2-sulfonamide (200 mg, 0.79 mmol) in methanol (3 mL) was added potassium carbonate (435 mg, 3.15 mmol) and dimethyl (1-diazo-2-oxopropyl)phosphonate (181 mg, 0.94 mmol). The reaction mixture was warmed to 50° C. and allowed to stir for 4 h. The reaction mixture was allowed to cool, poured into water (5 mL), and extracted with ethyl acetate (2×5 mL). The combined organic extracts were dried (sodium sulfate), filtered, and concentrated under reduced pressure. The residue was purified by silica gel chromatography, eluting with ethyl acetate:petroleum ether—33:67 to afford the title compound. MS: m/z=251.1 [M+H].

Intermediate 10

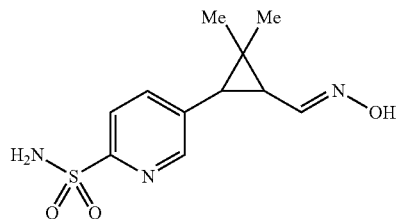 [SMILES: CC1(C)C(/C=N/O)C1c1ccc(S(N)(=O)=O)nc1]

5-{trans-3-[(Hydroxyimino)methyl]-2,2-dimethylcyclopropyl}pyridine-2-sulfonamide To a solution of 5-(trans-3-formyl-2,2-dimethylcyclopropyl)pyridine-2-sulfonamide (described in Intermediate 9) (180 mg, 0.71 mmol) in ethanol (5 mL) at ambient temperature was added hydroxylamine hydrochloride (148 mg, 2.12 mmol) and sodium carbonate (225 mg, 2.12 mmol) and the reaction mixture allowed to stir overnight. The reaction mixture was concentrated under reduced pressure, water (5 mL) was added to the residue and the resulting mixture was extracted with ethyl acetate (2×5 mL). The combined organic extracts were dried (sodium sulfate), filtered, then concentrated under reduced pressure to afford the title compound in sufficient purity for use in the next step. MS: m/z=270.0 [M+H].

Example 1

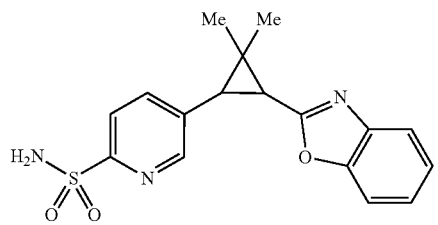 [SMILES: CC1(C)C(c2ccc(S(N)(=O)=O)nc2)C1c1nc2ccccc2o1]

5-[trans-3-(1,3-Benzoxazol-2-yl)-2,2-dimethylcyclopropyl]pyridine-2-sulfonamide, Enantiomer A Step A: trans-3-[6-(Benzylsulfanyl)pyridin-3-yl]-N-(2-hydroxyphenyl)-2,2-dimethylcyclopropanecarboxamide To a solution of trans-3-[6-(benzylsulfanyl)pyridin-3-yl]-2,2-dimethylcyclopropanecarboxylic acid (Intermediate 1) (247 mg, 0.788 mmol) in dichloromethane (5 mL) at ambient temperature was added 1-chloro-N,N,2-trimethylpropenylamine (0.313 mL, 2.37 mmol) and the reaction mixture allowed to stir for 18 h. The reaction mixture was concentrated under reduced pressure. The residue was dissolved in dichloromethane (2 mL) at ambient temperature and added to a solution of 2-aminophenol (215 mg, 1.97 mmol) and triethylamine (0.55 mL, 3.95 mmol) in dichloromethane (3 mL). The reaction mixture was allowed to stir for 3 h and was then concentrated under reduced pressure. The residue was purified by silica gel chromatography, eluting with a gradient of ethyl acetate:ethanol:heptane—0:0:100 to 22:8:70 to afford the title compound. MS: m/z=405.2 [M+H].

Step B: 2-{trans-3-[6-(Benzylsulfanyl)pyridin-3-yl]-2,2-dimethylcyclopropyl}-1,3-benzoxazole To a solution of trans-3-[6-(benzylsulfanyl)pyridin-3-yl]-N-(2-hydroxyphenyl)-2,2-dimethylcyclopropanecarboxamide (283 mg, 0.700 mmol) in toluene (5 mL) was added p-toluenesulfonic acid (166 mg, 0.874 mmol) and the reaction mixture warmed to reflux and allowed to stir for 4 d. The reaction mixture was allowed to cool, diluted with saturated aqueous sodium bicarbonate, and extracted with ethyl acetate (3×). The combined organic extracts were dried (magnesium sulfate), filtered, and concentrated under reduced pressure. The residue was purified by silica gel chromatography, eluting with a gradient of ethyl acetate:heptane—0:100 to 10:90 to afford the title compound. MS: m/z=387.1 [M+H].

Step C: 5-[trans-3-(1,3-Benzoxazol-2-yl)-2,2-dimethylcyclopropyl]pyridine-2-sulfonamide To a solution of 2-{trans-3-[6-(benzylsulfanyl)pyridin-3-yl]-2,2-dimethylcyclopropyl}-1,3-benzoxazole (156 mg, 0.404 mmol) in acetonitrile (1.7 mL) at 0° C. were added acetic acid (0.064 mL) and water (0.043 mL) and the reaction mixture allowed to stir for 1 min. 1,3-Dichloro-5,5-dimethylimidazolidine-2,4-dione (159 mg, 0.807 mmol) was added and the reaction mixture allowed to stir for 90 min. Ammonium hydroxide (0.6 mL, 4.3 mmol) was added and the reaction mixture allowed to warm to ambient temperature and stir for 18 h. The reaction mixture was concentrated under reduced pressure. Water was added and the mixture extracted with ethyl acetate (3×). The combined organic extracts were filtered through a pad of Celite® washing with ethyl acetate then concentrated under reduced pressure. The residue was purified by silica gel chromatography, eluting with a gradient of ethyl acetate:heptane—0:100 to 50:50 to afford the title compound. MS: m/z=344.1 [M+H].

5-[trans-3-(1,3-Benzoxazol-2-yl)-2,2-dimethylcyclopropyl]pyridine-2-sulfonamide, Enantiomer A Racemic 5-[trans-3-(1,3-benzoxazol-2-yl)-2,2-dimethylcyclopropyl]pyridine-2-sulfonamide was resolved by SFC, utilizing a ChiralPak OZ-H column, eluting with methanol:carbon dioxide:diethylamine—25:75:0.1. The first major peak to elute was 5-[trans-3-(1,3-benzoxazol-2-yl)-2,2-dimethylcyclopropyl]pyridine-2-sulfonamide, enantiomer A, the title compound, and the second major peak to elute was 5-[trans-3-(1,3-benzoxazol-2-yl)-2,2-dimethylcyclopropyl] pyridine-2-sulfonamide, enantiomer B. MS: m/z=344.1 [M+H]. $^1$H NMR (500 MHz, DMSO-d$_6$) δ 8.76 (d, J=1.9 Hz, 1H), 8.05 (dd, J=8.2, 2.1 Hz, 1H), 7.88 (d, J=8.1 Hz, 1H), 7.72-7.66 (m, 2H), 7.43 (br s, 2H), 7.40-7.32 (m, 2H), 3.10-3.01 (m, 2H), 1.29 (s, 3H), 1.02 (s, 3H).

Example 2

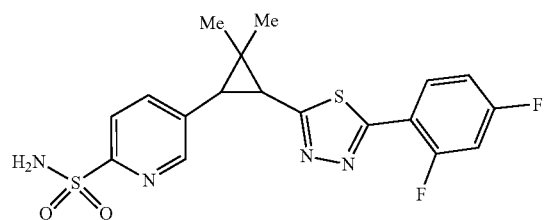 [SMILES: CC1(C)C(c2ccc(S(N)(=O)=O)nc2)C1c1nnc(-c2ccc(F)cc2F)s1]

5-{trans-3-[5-(2,4-Difluorophenyl)-1,3,4-thiadiazol-2-yl]-2,2-dimethylcyclopropyl}pyridine-2-sulfonamide Step A: trans-3-[6-(Benzylsulfanyl)pyridin-3-yl]-2,2-dimethylcyclopropanecarbonyl Chloride To a solution of trans-3-[6-(benzylsulfanyl)pyridin-3-yl]-2,2-dimethylcyclopropanecarboxylic acid (Intermediate 1) (147 mg, 0.468 mmol) in dichloromethane (2 mL) was added 1-chloro-N,N,2-trimethylpropenylamine (0.186 mL, 1.40 mmol) at ambient temperature and the reaction mixture allowed to stir for 3 h. The reaction mixture was concentrated under reduced pressure to afford the title compound in sufficient purity for use in the next step.

Step B: N'-({trans-3-[6-(Benzylsulfanyl)pyridin-3-yl]-2,2-dimethylcyclopropyl}carbonyl)-2,4-difluorobenzohydrazide To a solution of 2,4-difluorobenzohydrazide (201 mg, 1.17 mmol) in dichloromethane (3 mL) at 0° C. was added triethylamine (0.326 mL, 2.34 mmol) and the reaction mixture allowed to stir for 1 min. A solution of trans-3-[6-(benzylsulfanyl)pyridin-3-yl]-2,2-dimethylcyclopropanecarbonyl chloride in dichloromethane (2 mL) was added slowly and the reaction mixture allowed to warm to ambient temperature and stir for 18 h. The reaction mixture was concentrated under reduced pressure and the residue purified by silica gel chromatography, eluting with a gradient of ethyl acetate:heptane—0:100 to 50:50 to afford the title compound. MS: m/z=468.2 [M+H].

Step C: 2-(Benzylsulfanyl)-5-{trans-3-[5-(2,4-difluorophenyl)-1,3,4-thiadiazol-2-yl]-2,2-dimethylcyclopropyl}pyridine To a solution of N'-({trans-3-[6-(benzylsulfanyl)pyridin-3-yl]-2,2-dimethylcyclopropyl}carbonyl)-2,4-difluorobenzohydrazide (47 mg, 0.101 mmol) in tetrahydrofuran (2 mL) was added Lawesson's reagent (142 mg, 0.352 mmol) and the reaction mixture refluxed for 4 h. The reaction mixture was allowed to cool then concentrated under reduced pressure. The residue was purified by silica gel chromatography, eluting with a gradient of ethyl acetate:heptane—0:100 to 25:75 to afford the title compound. MS: m/z=466.2 [M+H].

Step D: 5-{trans-3-[5-(2,4-Difluorophenyl)-1,3,4-thiadiazol-2-yl]-2,2-dimethylcyclopropyl}pyridine-2-sulfonamide To a solution of 2-(benzylsulfanyl)-5-{trans-3-[5-(2,4-difluorophenyl)-1,3,4-thiadiazol-2-yl]-2,2-dimethylcyclopropyl}pyridine (47 mg, 0.101 mmol) in acetonitrile (1 mL) at 0° C. were added acetic acid (0.038 mL) and water (0.025 mL) and the reaction mixture allowed to stir for 1 min. 1,3-Dichloro-5,5-dimethylimidazolidine-2,4-dione (40 mg, 0.203 mmol) was added and the reaction mixture allowed to stir for 90 min. Ammonium hydroxide (0.140 mL, 1.01 mmol) was added slowly and the reaction mixture allowed to stir for 1 h. The reaction mixture was warmed to ambient temperature and concentrated under reduced pressure. The residue was purified by silica gel chromatography, eluting with a gradient of ethyl acetate:heptane—0:100 to 50:50 to afford the title compound. MS: m/z=423.1 [M+H]. $^1$H NMR (500 MHz, CDCl$_3$) δ 8.63 (s, 1H), 8.50-8.33 (m, 1H), 7.99 (d, J=8.1 Hz, 1H), 7.80 (dd, J=8.1, 1.2 Hz, 1H), 7.07 (td, J=8.9, 2.4 Hz, 1H), 7.04-6.90 (m, 1H), 5.05 (s, 2H), 3.16 (d, J=6.0 Hz, 1H), 2.78 (d, J=6.0 Hz, 1H), 1.31 (s, 3H), 1.09 (s, 3H).

Example 3

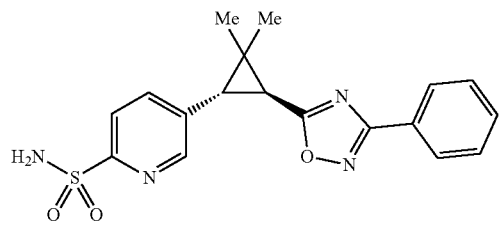 [SMILES: CC1(C)[C@@H](c2ccc(S(N)(=O)=O)nc2)[C@@H]1c1nc(-c2ccccc2)no1]

5-[(1S,3S)-2,2-Dimethyl-3-(3-phenyl-1,2,4-oxadiazol-5-yl)cyclopropyl]pyridine-2-sulfonamide Step A: N-tert-Butyl-5-[(1S,3S)-2,2-dimethyl-3-(3-phenyl-1,2,4-oxadiazol-5-yl)cyclopropyl]pyridine-2-sulfonamide To a sealable vessel containing ethyl (1S,3S)-3-[6-(tert-butylsulfamoyl)pyridin-3-yl]-2,2-dimethylcyclopropanecarboxylate (described in Intermediate 2) (100 mg, 0.282 mmol) were added N'-hydroxybenzimidamide (77 mg, 0.56 mmol), potassium carbonate (117 mg, 0.846 mmol), and toluene (2 mL) sequentially. The vessel was sealed and the reaction mixture warmed to 120° C. and allowed to stir for 18 h. The vessel was cooled, unsealed, and N-hydroxybenzimidamide (77 mg, 0.56 mmol) and potassium carbonate (117 mg, 0.846 mmol) were added. The vessel was sealed and the reaction mixture warmed to 120° C. and allowed to stir overnight. The reaction mixture was allowed to cool, diluted with ethyl acetate, filtered through a pad of Celite®, washing with ethyl acetate, and concentrated under reduced pressure. The residue was purified by silica gel chromatography, eluting with a gradient of ethyl acetate:heptane—0:100 to 50:50 to afford the title compound. MS: m/z=427.2 [M+H].

Step B: 5-[(1S,3S)-2,2-Dimethyl-3-(3-phenyl-1,2,4-oxadiazol-5-yl)cyclopropyl]pyridine-2-sulfonamide To a vessel containing N-tert-butyl-5-[(1S,3S)-2,2-dimethyl-3-(3-phenyl-1,2,4-oxadiazol-5-yl)cyclopropyl]pyridine-2-sulfonamide (111 mg, 0.260 mmol) was added trifluoroacetic acid (3 mL) and the reaction mixture warmed to 60° C. and allowed to stir for 2 h. The reaction mixture was allowed to cool and then concentrated under reduced pressure. The residue was taken up in saturated aqueous sodium bicarbonate and extracted with ethyl acetate (3×). The combined organic extracts were dried (magnesium sulfate), filtered, and concentrated under reduced pressure and the residue co-evaporated with diethyl ether/heptane (3×) to afford the title compound. MS: m/z=371.1 [M+H]. $^1$H NMR (600 MHz, CDCl$_3$) δ 8.61 (s, 1H), 8.08 (d, J=6.5 Hz, 2H), 8.00 (d, J=8.1 Hz, 1H), 7.78 (d, J=6.2 Hz, 1H), 7.61-7.40 (m, 3H), 5.02 (s, 2H), 3.07 (d, J=6.2 Hz, 1H), 2.66 (d, J=6.0 Hz, 1H), 1.46 (s, 3H), 1.09 (s, 3H).

Example 4

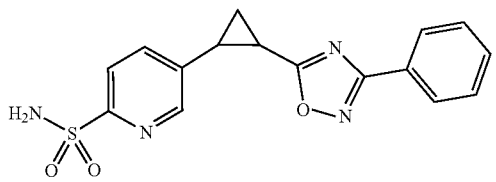 [SMILES: NS(=O)(=O)c1ccc(C2CC2c2nc(-c3ccccc3)no2)cn1]

5-[trans-2-(3-Phenyl-1,2,4-oxadiazol-5-yl)cyclopropyl]pyridine-2-sulfonamide

Step A: 2-(Benzylsulfanyl)-5-[2-(3-phenyl-1,2,4-oxadiazol-5-yl)cyclopropyl]pyridine To a solution of 2-[6-(benzylsulfanyl)pyridin-3-yl]cyclopropanecarboxylic acid (Intermediate 4) (350 mg, 1.227 mmol) in 1,4-dioxane (10 mL) was added 1,1'-carbonyldiimidazole (298 mg, 1.84 mmol) and the reaction mixture warmed to 60° C. and allowed to stir for 2 h. N-Hydroxybenzimidamide (334 mg, 2.453 mmol) was added and the reaction mixture warmed to 100° C. and allowed to stir for 3 h. The reaction mixture was allowed to cool then concentrated under reduced pressure. The residue was purified by silica gel chromatography, eluting with a gradient of ethyl acetate:heptane—0:100 to 25:75 to afford the title compound. MS: m/z=386.2 [M+H].

Step B: 5-[trans-2-(3-Phenyl-1,2,4-oxadiazol-5-yl)cyclopropyl]pyridine-2-sulfonamide To a solution of trans-2-(benzylsulfanyl)-5-[2-(3-phenyl-1,2,4-oxadiazol-5-yl)cyclopropyl]pyridine (312 mg, 0.809 mmol) in acetonitrile (4 mL) at 0° C. were added acetic acid (0.150 mL) and water (0.100 mL) and the reaction mixture allowed to stir for 1 minute. 1,3-Dichloro-5,5-dimethylimidazolidine-2,4-dione (319 mg, 1.62 mmol) was added and the reaction mixture allowed to stir for 90 min. Ammonium hydroxide (1.2 mL, 8.6 mmol) was added slowly and then the reaction mixture was warmed to ambient temperature and allowed to stir for 1 h. The reaction mixture was concentrated under reduced pressure and the residue purified by silica gel chromatography, eluting with a gradient of ethyl acetate:heptane—0:100 to 75:25 to afford the title compound. MS: m/z=343.1 [M+H].

Step C: 5-[trans-2-(3-Phenyl-1,2,4-oxadiazol-5-yl)cyclopropyl]pyridine-2-sulfonamide, Enantiomer B Racemic 5-[trans-2-(3-phenyl-1,2,4-oxadiazol-5-yl)cyclopropyl]pyridine-2-sulfonamide was resolved by SFC, utilizing a ChromegaChiral CC4 column, eluting with methanol:carbon dioxide:diethylamine—35:65:0.1. The first major peak to elute was 5-[trans-2-(3-phenyl-1,2,4-oxadiazol-5-yl)cyclopropyl]pyridine-2-sulfonamide, enantiomer A, and the second major peak to elute was 5-[trans-2-(3-phenyl-1,2,4-oxadiazol-5-yl)cyclopropyl]pyridine-2-sulfonamide, enantiomer B, the title compound. MS: m/z=343.1 [M+H]. $^1$H NMR (500 MHz, CDCl$_3$) δ 8.59 (d, J=2.0 Hz, 1H), 8.16-8.02 (m, 2H), 7.99 (d, J=8.2 Hz, 1H), 7.66 (dd, J=8.1, 2.2 Hz, 1H), 7.59-7.41 (m, 3H), 5.03 (s, 2H), 3.01-2.83 (m, 1H), 2.63 (dt, J=9.1, 5.1 Hz, 1H), 2.09 (dt, J=9.3, 5.6 Hz, 1H), 1.80 (dt, J=8.9, 6.0 Hz, 1H).

Example 5

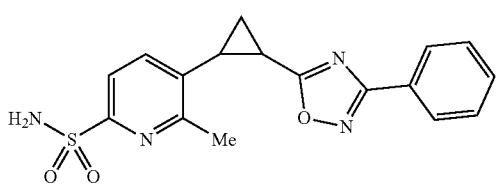 [SMILES: Cc1nc(S(N)(=O)=O)ccc1C1CC1c1nc(-c2ccccc2)no1]

6-Methyl-5-[trans-2-(3-phenyl-1,2,4-oxadiazol-5-yl)cyclopropyl]pyridine-2-sulfonamide Step A: 6-(Benzylsulfanyl)-2-methyl-3-[trans-2-(3-phenyl-1,2,4-oxadiazol-5-yl)cyclopropyl]pyridine To a solution of trans-2-[6-(benzylsulfanyl)-2-methylpyridin-3-yl]cyclopropanecarboxylic acid (Intermediate 5) (265 mg, 0.885 mmol) in 2-methyltetrahydrofuran (5 mL) at ambient temperature in a sealable vessel were added N-hydroxybenzimidamide (157 mg, 1.15 mmol), diisopropylethylamine (0.464 mL, 2.66 mmol), and 2,4,6-tripropyl-1,3,5,2,4,6-trioxatriphosphorinane-2,4,6-trioxide (0.685 mL, 1.15 mmol) and the reaction mixture allowed to stir for 30 min. N-Hydroxybenzimidamide (157 mg, 1.15 mmol) and 2,4,6-tripropyl-1,3,5,2,4,6-trioxatriphosphorinane-2,4,6-trioxide (0.685 mL, 1.15 mmol) were added and the reaction mixture allowed to stir for 1 h. The vessel was sealed and then the reaction mixture was warmed to 120° C. and allowed to stir for 30 min. The reaction mixture was cooled, diluted with saturated aqueous sodium bicarbonate, and extracted with dichloromethane (3×). The combined organic extracts were dried (magnesium sulfate), filtered, and concentrated under reduced pressure. The residue was purified by silica gel chromatography, eluting with a gradient of ethyl acetate:heptane—0:100 to 25:75 to afford the title compound. MS: m/z=400.2 [M+H].

Step B: 6-Methyl-5-[trans-2-(3-phenyl-1,2,4-oxadiazol-5-yl)cyclopropyl]pyridine-2-sulfonamide To a solution of 6-(benzylsulfanyl)-2-methyl-3-[trans-2-(3-phenyl-1,2,4-oxadiazol-5-yl)cyclopropyl]pyridine (140 mg, 0.350 mmol) in acetonitrile (3 mL) at 0° C. were added acetic acid (0.113 mL) and water (0.075 mL) and the reaction mixture allowed to stir for 1 min. 1,3-Dichloro-5,5-dimethylimidazolidine-2,4-dione (138 mg, 0.701 mmol) was added and the reaction mixture allowed to stir for 90 min. Ammonium hydroxide (0.487 mL, 3.50 mmol) was added slowly and then the reaction mixture was warmed to ambient temperature and allowed to stir for 2 h. The reaction mixture was diluted with dichloromethane, filtered through a pad of Celite®, washing with dichloromethane, and concentrated under reduced pressure. The residue was purified by silica gel chromatography, eluting with a gradient of ethyl acetate:heptane—0:100 to 75:25 to afford the title compound. MS: m/z=357.1 [M+H]. ¹H NMR (500 MHz, CDCl₃) δ 8.19-7.97 (m, 2H), 7.84 (d, J=7.9 Hz, 1H), 7.58 (d, J=7.9 Hz, 1H), 7.56-7.39 (m, 3H), 4.98 (s, 2H), 2.98-2.81 (m, 1H), 2.71 (s, 3H), 2.49 (dt, J=9.6, 5.1 Hz, 1H), 2.03 (dt, J=10.3, 5.3 Hz, 1H), 1.80-1.63 (m, 1H).

Example 6

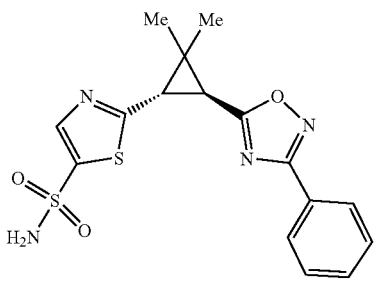 [SMILES: CC1(C)[C@@H](c2nc(-c3ccccc3)no2)[C@@H]1c1ncc(S(N)(=O)=O)s1]

2-[(1S,3S)-2,2-dimethyl-3-(3-phenyl-1,2,4-oxadiazol-5-yl)cyclopropyl]-1,3-thiazole-5-sulfonamide To a solution of (1S,3S)-2,2-dimethyl-3-(5-sulfamoyl-1,3-thiazol-2-yl)cyclopropanecarboxylic acid (Intermediate 6) (83 mg, 0.301 mmol) in 1,4-dioxane (2 mL) was added 1,1'-carbonyldiimidazole (61.0 mg, 0.376 mmol) and the reaction mixture warmed to 50° C. and allowed to stir for 2 h. N'-hydroxybenzimidamide (61.5 mg, 0.452 mmol) was added and the reaction mixture warmed to 100° C. and allowed to stir for 18 h. The reaction mixture was cooled, concentrated under reduced pressure, and the residue purified by silica gel chromatography, eluting with a gradient of ethyl acetate:heptane—0:100 to 50:50 to afford the title compound. MS: m/z=377.1 [M+H]. ¹H NMR (500 MHz, CDCl₃) δ 8.14 (s, 1H), 8.12-7.98 (m, 2H), 7.49 (m, 3H), 5.09 (s, 2H), 3.26-3.12 (m, 2H), 1.42 (s, 3H), 1.32 (s, 3H).

Example 7

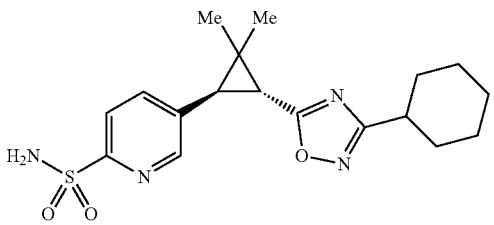 [SMILES: CC1(C)[C@H](c2ccc(S(N)(=O)=O)nc2)[C@H]1c1nc(C2CCCCC2)no1]

5-[(1R,3R)-3-(3-Cyclohexyl-1,2,4-oxadiazol-5-yl)-2,2-dimethylcyclopropyl]pyridine-2-sulfonamide Step A: N-tert-Butyl-5-[(1R,3R)-3-(3-cyclohexyl-1,2,4-oxadiazol-5-yl)-2,2-dimethylcyclopropyl]pyridine-2-sulfonamide To a solution of (1R,3R)-3-[6-(tert-butylsulfamoyl)pyridin-3-yl]-2,2-dimethylcyclopropanecarboxylic acid (Intermediate 2) (175 mg, 0.536 mmol) in 1,4-dioxane (3 mL) was added 1,1'-carbonyldiimidazole (109 mg, 0.670 mmol) and the reaction mixture warmed to 50° C. and allowed to stir for 2 h. N'-hydroxycyclohexanecarboximidamide (95 mg, 0.67 mmol) was added and the mixture was warmed to 100° C. and allowed to stir for 18 h. The reaction mixture was cooled then concentrated under reduced pressure. The residue was purified by silica gel chromatography, eluting with a gradient of ethyl acetate:heptane—0:100 to 25:75 to afford the title compound. MS: m/z=433.3 [M+H].

Step B: 5-[(1R,3R)-3-(3-Cyclohexyl-1,2,4-oxadiazol-5-yl)-2,2-dimethylcyclopropyl]pyridine-2-sulfonamide To a vessel containing N-tert-butyl-5-[(1R,3R)-3-(3-cyclohexyl-1,2,4-oxadiazol-5-yl)-2,2-dimethylcyclopropyl]pyridine-2-sulfonamide (212 mg, 0.490 mmol) was added trifluoroacetic acid (3 mL) and the reaction mixture warmed to 60° C. and allowed to stir for 4 h. The reaction mixture was allowed to cool then concentrated under reduced pressure. The residue was dissolved in dichloromethane and excess PS-diisopropylethylamine resin was added. The mixture was aged for 10 min, filtered (washing with dichloromethane), and the filtrate concentrated under reduced pressure. The residue was purified by silica gel chromatography, eluting with a gradient of ethyl acetate:ethanol:heptane—0:0:100 to 19:6:75 to afford the title compound. MS: m/z=377.2 [M+H]. ¹H NMR (600 MHz, DMSO-d₆) δ 8.70 (d, J=1.7 Hz, 1H), 8.00 (dd, J=8.2, 1.9 Hz, 1H), 7.84 (d, J=8.1 Hz, 1H), 7.42 (br s, 2H), 3.08 (d, J=6.2 Hz, 1H), 2.93 (d, J=6.1 Hz, 1H), 2.75 (tt, J=11.1, 3.5 Hz, 1H), 1.90 (d, J=12.6 Hz, 2H), 1.71 (dd, J=13.1, 3.5 Hz, 2H), 1.46 (q, J=12.2 Hz, 2H), 1.39-1.27 (m, 2H), 1.25 (s, 3H), 1.14 (d, J=6.4 Hz, 2H), 0.95 (s, 3H).

Example 8

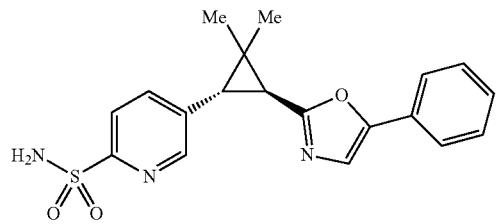 [SMILES: CC1(C)[C@@H](c2ccc(S(N)(=O)=O)nc2)[C@@H]1c1ncc(-c2ccccc2)o1]

5-[(1S,3S)-2,2-Dimethyl-3-(5-phenyl-1,3-oxazol-2-yl)cyclopropyl]pyridine-2-sulfonamide Step A: (1S,3S)-3-[6-(tert-Butylsulfamoyl)pyridin-3-yl]-2,2-dimethyl-N-(2-oxo-2-phenylethyl)cyclopropanecarboxamide To a solution of (1S,3S)-3-[6-(tert-butylsulfamoyl)pyridin-3-yl]-2,2-dimethylcyclopropanecarboxylic acid (100 mg, 0.306 mmol) (Intermediate 3) in N,N-dimethylformamide (3 mL) at ambient temperature were added HATU (151 mg, 0.398 mmol) and diisopropylethylamine (0.17 mL, 0.97 mmol) sequentially and the reaction mixture allowed to stir for 30 min. 2-Amino-1-phenylethanone hydrochloride (79 mg, 0.46 mmol) was added and the reaction mixture allowed to stir for 18 h. The reaction mixture was concentrated under reduced pressure and the residue purified by silica gel chromatography, eluting with a gradient of ethyl acetate:heptane—0:100 to 100:0 to afford the title compound. MS: m/z=444.2 [M+H].

Step B: 5-[(1S,3S)-2,2-Dimethyl-3-(5-phenyl-1,3-oxazol-2-yl)cyclopropyl]pyridine-2-sulfonamide To a solution of (1S,3S)-3-[6-(tert-butylsulfamoyl)pyridin-3-yl]-2,2-dimethyl-N-(2-oxo-2-phenylethyl)cyclopropanecarboxamide (67.9 mg, 0.153 mmol) in acetonitrile (1 mL) was added phosphorous oxychloride (70 µL, 0.75 mmol) the reaction mixture warmed to 80° C. and allowed to stir for 18 h. The reaction mixture was allowed to cool, trifluoroacetic acid (0.5 mL) was added, and the reaction mixture was warmed to 60° C. and allowed to stir for 2 h. The reaction mixture was allowed to cool then concentrated under reduced pressure. The residue was dissolved in methanol (0.5 mL) and an aqueous solution of ammonium hydroxide (15 M, 0.5 mL, 7.5 mmol) was added and the reaction mixture heated to 50° C. and allowed to stir for 2 h. The reaction mixture was allowed to cool then concentrated under reduced pressure. The residue was dissolved in DMSO (1.5 mL), filtered, then purified by preparative HPLC, eluting with a gradient of acetonitrile:water:trifluoroacetic acid—20:80:0.1 to 65:35:0.1. The product-containing fractions were concentrated under reduced pressure and the residue dissolved in dichloromethane and excess PS-diisopropylethylamine resin added. The mixture was aged for 10 min then filtered, washing with dichloromethane, and the filtrate was concentrated under reduced pressure to afford the title compound. MS: m/z=370.1 [M+H]. $^1$H NMR (600 MHz, CDCl$_3$) δ 8.61 (s, 1H), 7.97 (d, J=8.2 Hz, 1H), 7.77 (d, J=6.2 Hz, 1H), 7.63 (d, J=7.5 Hz, 2H), 7.43 (t, J=7.8 Hz, 2H), 7.33 (t, J=7.5 Hz, 1H), 7.27 (s, 1H), 5.03 (s, 2H), 2.91 (d, J=6.0 Hz, 1H), 2.56 (d, J=6.0 Hz, 1H), 1.36 (s, 3H), 1.04 (s, 3H).

Example 9

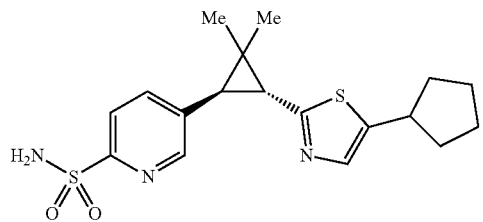 [SMILES: CC1(C)[C@H](c2ccc(S(N)(=O)=O)nc2)[C@H]1c1ncc(C2CCCC2)s1]

5-[(1R,3R)-3-(5-Cyclopentyl-1,3-thiazol-2-yl)-2,2-dimethylcyclopropyl]pyridine-2-sulfonamide Step A: (1R,3R)-3-[6-(tert-Butylsulfamoyl)pyridin-3-yl]-N-(2-cyclopentyl-2-oxoethyl)-2,2-dimethylcyclopropanecarboxamide To a solution of (1R,3R)-3-[6-(tert-butylsulfamoyl)pyridin-3-yl]-2,2-dimethylcyclopropanecarboxylic acid (Intermediate 2) (100 mg, 0.306 mmol) in N,N-dimethylformamide (3 mL) at ambient temperature were added HATU (151 mg, 0.398 mmol) and diisopropylethylamine (0.17 mL, 0.973 mmol) sequentially and the reaction mixture allowed to stir for 30 min. 2-Amino-1-cyclopentylethanone hydrochloride (75 mg, 0.460 mmol) was added and the reaction mixture allowed to stir for 18 h. The reaction mixture was concentrated under reduced pressure and the residue purified by silica gel chromatography, eluting with a gradient of ethyl acetate:heptane—0:100 to 100:0 to afford the title compound. MS: m/z=436.2 [M+H].

Step B: 5-[(1R,3R)-3-(5-Cyclopentyl-1,3-thiazol-2-yl)-2,2-dimethylcyclopropyl]pyridine-2-sulfonamide To a solution of (1R,3R)-3-[6-(tert-butylsulfamoyl)pyridin-3-yl]-N-(2-cyclopentyl-2-oxoethyl)-2,2-dimethylcyclopropanecarboxamide (66.6 mg, 0.153 mmol) in acetonitrile (1 mL) was added Lawesson's reagent (186 mg, 0.459 mmol) and the reaction mixture warmed to 80° C. and allowed to stir for 18 h. The reaction mixture was allowed to cool then diluted with ethyl acetate, filtered through a pad of silica gel (washing with ethyl acetate), and concentrated under reduced pressure. The residue was purified by silica gel chromatography, eluting with a gradient of ethyl acetate:heptane—0:100 to 50:50. The product-containing fractions were concentrated under reduced pressure. The residue was dissolved in trifluoroacetic acid (1 mL) and the reaction mixture warmed to 60° C. and allowed to stir for 2 h. The reaction mixture was allowed to cool and concentrated under reduced pressure. The residue was taken up in DMSO (1.5 mL), filtered, and purified by preparative HPLC eluting with a gradient of acetonitrile:water:trifluoroacetic acid—20:80:0.1 to 65:35:0.1. The product-containing fractions were concentrated under reduced pressure and the residue dissolved in dichloromethane and excess PS-diisopropylethylamine resin added. The mixture was aged for 10 min then filtered, washing with dichloromethane), and the filtrate was concentrated under reduced pressure to afford the title compound. MS: m/z=378.2 [M+H]. $^1$H NMR (600 MHz, CDCl$_3$) δ 8.58 (s, 1H), 7.94 (d, J=8.2 Hz, 1H), 7.74 (dd, J=8.0, 1.4 Hz, 1H), 7.35 (s, 1H), 5.07 (s, 2H), 3.22 (q, J=8.0 Hz, 1H), 2.87 (d, J=5.9 Hz, 1H), 2.65 (d, J=6.0 Hz, 1H), 2.13 (m, 1H), 1.81 (m, 2H), 1.69 (m, 2H), 1.61 (m, 3H), 1.24 (s, 3H), 1.00 (s, 3H).

Example 10

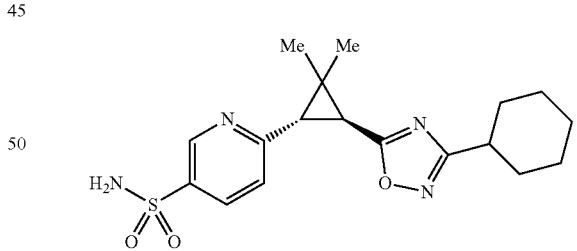

6-[(1S,3S)-3-(3-Cyclohexyl-1,2,4-oxadiazol-5-yl)-2,2-dimethylcyclopropyl]pyridine-3-sulfonamide Step A: N-tert-Butyl-6-[(1S,3S)-3-(3-cyclohexyl-1,2,4-oxadiazol-5-yl)-2,2-dimethylcyclopropyl]pyridine-3-sulfonamide To a solution of (1S,3S)-3-[5-(tert-butylsulfamoyl)pyridin-2-yl]-2,2-dimethylcyclopropanecarboxylic acid (Intermediate 7) (175 mg, 0.536 mmol) in 1,4-dioxane (3 mL) was added 1,1'-carbonyldiimidazole (109 mg, 0.670 mmol) and the reaction mixture warmed to 50° C. and allowed to stir for 2 h. N-Hydroxycyclohexanecarboximidamide (95 mg, 0.67 mmol) was added and the reaction mixture warmed to 100° C. and allowed to stir for 18 h. The reaction mixture was allowed to cool then concentrated under reduced pressure. The residue was purified by silica gel chromatography, eluting with a gradient of ethyl acetate:heptane—0:100 to 25:75 to afford the title compound. MS: m/z=433.3 [M+H].

Step B: 6-[(1S,3S)-3-(3-Cyclohexyl-1,2,4-oxadiazol-5-yl)-2,2-dimethylcyclopropyl]pyridine-3-sulfonamide To a vessel containing N-tert-butyl-6-[(1S,3S)-3-(3-cyclohexyl-1,2,4-oxadiazol-5-yl)-2,2-dimethylcyclopropyl] pyridine-3-sulfonamide (135 mg, 0.312 mmol) was added trifluoroacetic acid (3 mL) and the reaction mixture warmed to 60° C. and allowed to stir for 4 h. The reaction mixture was allowed to cool then concentrated under reduced pressure. The residue was dissolved in dichloromethane and excess PS-diisopropylethylamine resin was added. The mixture was aged for 10 min, filtered (washing with dichloromethane), and the filtrate concentrated under reduced pressure. The residue was purified by silica gel chromatography, eluting with a gradient of ethyl acetate:ethanol:heptane—0:0:100 to 19:6:75 to afford the title compound. MS: m/z=377.2 [M+H]. $^1$H NMR (600 MHz, DMSO-d$_6$) δ 8.87 (d, J=2.1 Hz, 1H), 8.09 (dd, J=8.2, 2.3 Hz, 1H), 7.73 (d, J=8.3 Hz, 1H), 7.55 (s, 2H), 3.14 (d, J=5.9 Hz, 1H), 3.05 (d, J=5.8 Hz, 1H), 2.81-2.66 (m, 1H), 1.90 (d, J=13.2 Hz, 2H), 1.71 (d, J=13.1 Hz, 2H), 1.63 (d, J=12.5 Hz, 1H), 1.48-1.41 (m, 2H), 1.41-1.31 (m, 2H), 1.28 (s, 3H), 1.22 (d, J=12.0 Hz, 1H), 1.08 (s, 3H).

Example 11

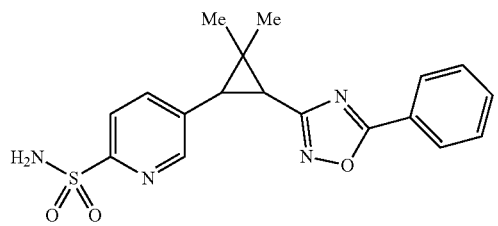 [SMILES: CC1(C)C(c2ccc(S(N)(=O)=O)nc2)C1c1noc(-c2ccccc2)n1]

5-[trans-2,2-Dimethyl-3-(5-phenyl-1,2,4-oxadiazol-3-yl)cyclopropyl]pyridine-2-sulfonamide To a solution of benzoic acid (21.5 mg, 0.176 mmol) in N,N-dimethylformamide (2 mL) were added HATU (67 mg, 0.18 mmol) and diisopropylethylamine (0.031 mL, 0.18 mmol) and the reaction mixture allowed to stir for 10 min. trans-N'-Hydroxy-2,2-dimethyl-3-(6-sulfamoylpyridin-3-yl)cyclopropanecarboximidamide (Intermediate 8) (50 mg, 0.176 mmol) was added and the reaction mixture allowed to stir for 30 min. The reaction mixture was warmed to 80° C. and allowed to stir for 5 h. The reaction mixture was allowed to cool to ambient temperature and purified by preparative HPLC, eluting with a gradient of acetonitrile:water:ammonium hydroxide—35:65:0.05 to 65:35:0.05 to afford the title compound. MS: m/z=371.2 [M+H]. $^1$H NMR (400 MHz, CD$_3$OD): δ 8.66 (s, 1H); 8.13-8.15 (m, 2H); 7.96-7.97 (m, 2H); 7.55-7.67 (m, 3H), 2.96 (d, J=6.0 Hz, 1H); 2.74 (d, J=6.0 Hz, 1H); 1.35 (s, 3H); 1.05 (s, 3H).

Example 12

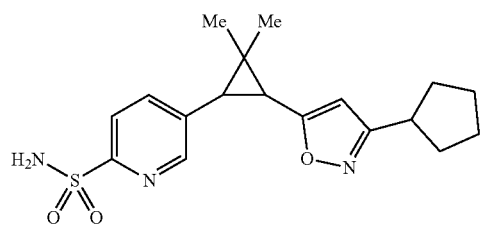 [SMILES: CC1(C)C(c2ccc(S(N)(=O)=O)nc2)C1c1cc(C2CCCC2)no1]

5-[trans-3-(3-Cyclopentylisoxazol-5-yl)-2,2-dimethylcyclopropyl]pyridine-2-sulfonamide To a solution of 5-(trans-3-ethynyl-2,2-dimethylcyclopropyl)pyridine-2-sulfonamide (Intermediate 9) (25 mg, 0.10 mmol) in methanol (2.4 mL) and water (0.6 mL) at ambient temperature were added cyclopentanecarbaldehyde oxime (17.0 mg, 0.150 mmol) and [bis(trifluoroacetoxy)iodo]benzene (86 mg, 0.200 mmol) and the reaction mixture allowed to stir for 18 h. The reaction mixture was filtered and purified by preparative HPLC, eluting with a gradient of acetonitrile:water:trifluoroacetic acid—36:64:0.1 to 66:34:0.1 to afford the title compound. MS: m/z=362.0 [M+H]. $^1$H NMR (400 MHz, CD$_3$OD): δ 8.62 (s, 1H); 7.89-7.99 (m, 2H); 6.22 (s, 1H); 3.09-3.13 (m, 1H); 2.70-2.76 (m, 1H); 2.62-2.68 (m, 1H); 2.06 (br s, 2H); 1.64-1.85 (m, 6H); 1.22 (s, 3H); 0.99 (s, 3H).

Example 13

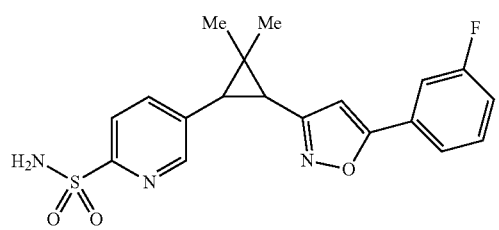 [SMILES: CC1(C)C(c2ccc(S(N)(=O)=O)nc2)C1c1cc(-c2cccc(F)c2)on1]

5-{trans-3-[5-(3-Fluorophenyl)isoxazol-3-yl]-2,2-dimethylcyclopropyl}pyridine-2-sulfonamide, Enantiomer B Step A: 5-{trans-3-[5-(3-Fluorophenyl)isoxazol-3-yl]-2,2-dimethylcyclopropyl}pyridine-2-sulfonamide To a solution of 5-{3-[(hydroxyimino)methyl]-2,2-dimethylcyclopropyl}pyridine-2-sulfonamide (Intermediate 10) (120 mg, 0.45 mmol) in N,N-dimethylformamide (2 mL) at ambient temperature was added NCS (59.5 mg, 0.45 mmol) and pyridine (0.0036 mL, 0.045 mmol) and the reaction mixture allowed to stir for 1 h. A solution of 1-ethynyl-3-fluorobenzene (80 mg, 0.67 mmol) in N,N-dimethylformamide (2 mL) was added and then the mixture was warmed to 85° C. and allowed to stir for 1 h. Triethylamine (0.06 mL, 0.45 mmol) was added and the reaction mixture allowed to stir for 1 h. The reaction mixture was allowed to cool then purified by preparative HPLC, eluting with a gradient of acetonitrile:water:trifluoroacetic acid—45:55:0.1 to 75:25:0.1 to afford the title compound. MS: m/z=388.1 [M+H].

Step B: 5-{trans-3-[5-(3-Fluorophenyl)isoxazol-3-yl]-2,2-dimethylcyclopropyl}pyridine-2-sulfonamide, Enantiomer B Racemic 5-{trans-3-[5-(3-fluorophenyl)isoxazol-3-yl]-2,2-dimethylcyclopropyl}pyridine-2-sulfonamide was resolved by SFC utilizing a ChiralPak OJ-H column, eluting with ethanol:carbon dioxide:ammonium hydroxide—30:70:0.1. The first major peak to elute was 5-{trans-3-[5-(3-fluorophenyl)isoxazol-3-yl]-2,2-dimethylcyclopropyl}pyridine-2-sulfonamide, enantiomer A, and the second major peak to elute was 5-{trans-3-[5-(3-fluorophenyl)isoxazol-3-yl]-2,2-dimethylcyclopropyl}pyridine-2-sulfonamide, enantiomer B, the title compound. MS: m/z=388.0 [M+H]. $^1$H NMR (400 MHz, CD$_3$OD): δ 8.68 (s, 1H); 7.94-8.01 (m, 2H); 7.67-7.72 (m, 1H); 7.52-7.64 (m, 2H); 7.22-7.25 (m, 1H); 6.93 (s, 1H); 2.81 (d, J=6.0 Hz, 1H); 2.65 (d, J=6.5 Hz, 1H); 1.27 (s, 3H); 1.06 (s, 3H).

The examples appearing in the following tables were prepared by analogy to the above examples, as described or prepared as a result of similar transformations with modifications known to those skilled in the art. The requisite starting materials were described herein, commercially available, known in the literature, or readily synthesized by one skilled in the art. Straightforward protecting group strategies were applied in some routes.

TABLE EX-A

| Example | X | R | MS [M + H] |
|---|---|---|---|
| A1 | Me | 5-phenyl-1,2,4-oxadiazol-3-yl | 371.2 |
| A2 | Me | 3-(4-trifluoromethylpyridin-3-yl)-1,2,4-oxadiazol-5-yl | 440.1 |
| A3 | Me | 3-cyclopentyl-1,2,4-oxadiazol-5-yl | 363.2 |
| A4 | Me | 5-cyclopentyl-oxazol-2-yl | 362.2 |
| A5 | Me | 5-phenylthiazol-2-yl | 386.1 |
| A6 | Me | 3-(5-chloro-2-methoxyphenyl)-1,2,4-oxadiazol-5-yl | 435.1 |
| A7 | Me | 3-(3-fluorophenyl)-1,2,4-oxadiazol-5-yl | 389.1 |
| A8 | Me | 3-(2,4-difluorophenyl)-1,2,4-oxadiazol-5-yl | 407.1 |
| A9 | Me | 3-(5-fluoropyridin-3-yl)-1,2,4-oxadiazol-5-yl | 390.1 |
| A10 | Me | 3-(3-trifluoromethylphenyl)-1,2,4-oxadiazol-5-yl | 439.1 |

TABLE EX-A-continued

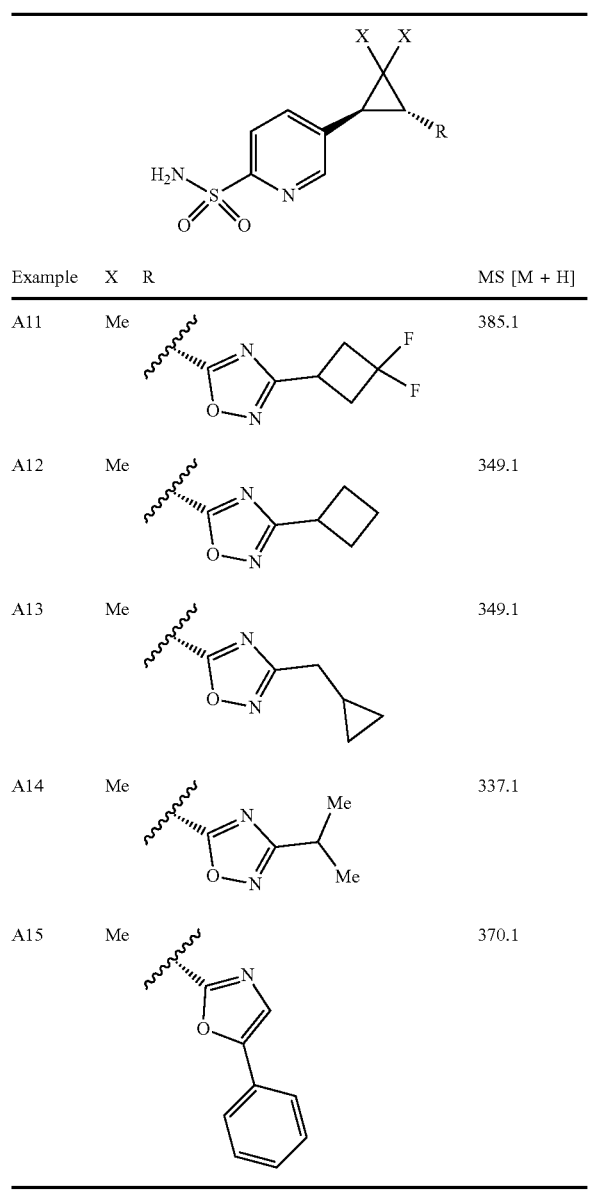

| Example | X | R | MS [M + H] |
|---|---|---|---|
| A11 | Me | (3,3-difluorocyclobutyl)-1,2,4-oxadiazole | 385.1 |
| A12 | Me | (cyclobutyl)-1,2,4-oxadiazole | 349.1 |
| A13 | Me | (cyclopropylmethyl)-1,2,4-oxadiazole | 349.1 |
| A14 | Me | (isopropyl)-1,2,4-oxadiazole | 337.1 |
| A15 | Me | (5-phenyl)oxazole | 370.1 |

TABLE EX-B

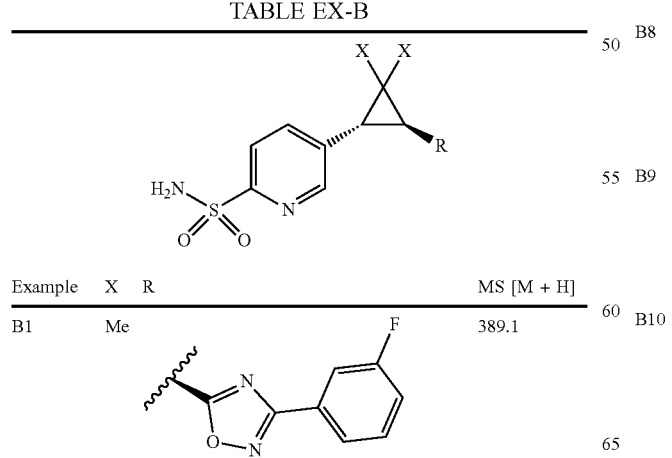

| Example | X | R | MS [M + H] |
|---|---|---|---|
| B1 | Me | 3-(3-fluorophenyl)-1,2,4-oxadiazole | 389.1 |

TABLE EX-B-continued

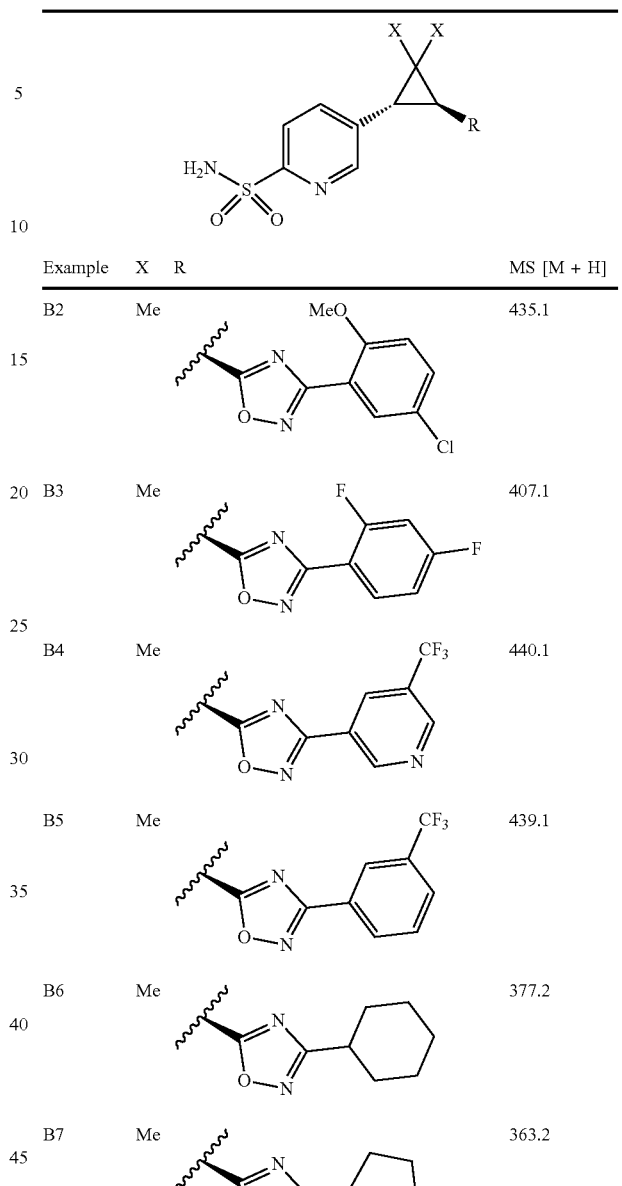

| Example | X | R | MS [M + H] |
|---|---|---|---|
| B2 | Me | 3-(2-methoxy-5-chlorophenyl)-1,2,4-oxadiazole | 435.1 |
| B3 | Me | 3-(2,4-difluorophenyl)-1,2,4-oxadiazole | 407.1 |
| B4 | Me | 3-(5-trifluoromethylpyridin-3-yl)-1,2,4-oxadiazole | 440.1 |
| B5 | Me | 3-(3-trifluoromethylphenyl)-1,2,4-oxadiazole | 439.1 |
| B6 | Me | 3-cyclohexyl-1,2,4-oxadiazole | 377.2 |
| B7 | Me | 3-cyclopentyl-1,2,4-oxadiazole | 363.2 |
| B8 | Me | 3-(3,3-difluorocyclobutyl)-1,2,4-oxadiazole | 385.1 |
| B9 | Me | 3-cyclobutyl-1,2,4-oxadiazole | 349.1 |
| B10 | Me | 3-(cyclopropylmethyl)-1,2,4-oxadiazole | 349.1 |

TABLE EX-B-continued

[Structure: 5-(cyclopropyl-R substituted)pyridine-2-sulfonamide with X,X on cyclopropane]

| Example | X | R | MS [M + H] |
|---------|---|---|------------|
| B11 | Me | [1,2,4-oxadiazole with cyclopropyl] | 335.1 |
| B12 | Me | [1,2,4-oxadiazole with C(Me)₃] | 351.2 |
| B13 | Me | [1,2,4-oxadiazole with CH(Me)₂] | 337.1 |
| B14 | Me | [oxazole with cyclopentyl] | 362.2 |
| B15 | Me | [thiazole with phenyl] | 386.1 |
| B16 | Me | [thiazole with cyclopentyl] | 378.2 |

TABLE EX-C

[Structure: 5-(cyclopropyl-R substituted)pyridine-2-sulfonamide with X,X on cyclopropane]

| Example | X | R | Stereochemistry Comment | MS [M + H] |
|---------|---|---|-------------------------|------------|
| C1 | Me | [1,2,4-oxadiazole with 2,6-difluoro-fluorophenyl] | trans, racemic | 424.9 |
| C2 | Me | [1,2,4-oxadiazole with cyclopentyl] | trans, racemic | 363.1 |
| C3 | Me | [isoxazole with 3-fluorophenyl] | trans, racemic | 388.1 |
| C4 | Me | [benzoxazole] | trans, racemic | 344.2 |
| C5 | H | [1,2,4-oxadiazole with phenyl] | trans, racemic | 343.1 |
| C6 | Me | [1,2,4-oxadiazole with phenyl] | trans, racemic | 371.2 |
| C7 | Me | [benzoxazole] | trans, single enantiomer | 343.4 |
| C8 | H | [1,2,4-oxadiazole with 3-fluorophenyl] | trans, racemic | 361.1 |

TABLE EX-C-continued

Structure: sulfonamide-pyridine-cyclopropane(X,X)-R

| Example | X | R | Stereochemistry Comment | MS [M + H] |
|---|---|---|---|---|
| C9 | H | 3-cyclopentyl-1,2,4-oxadiazol-5-yl | trans, racemic | 335.2 |
| C10 | Me | 5-cyclohexyl-1,2,4-oxadiazol-3-yl | trans, racemic | 377.0 |
| C11 | Me | 5-(1-(trifluoromethyl)cyclopropyl)-1,2,4-oxadiazol-3-yl | trans, racemic | 403.0 |
| C12 | Me | 5-(2,6-difluorophenyl)-1,2,4-oxadiazol-3-yl | trans, racemic | 407.0 |
| C13 | Me | 5-(3-fluorophenyl)isoxazol-3-yl | trans, single enantiomer | 388.0 |

TABLE EX-D

Structure: thiazole-sulfonamide-cyclopropane(X,X)-R

| Example | X | R | Stereochemistry Comment | MS [M + H] |
|---|---|---|---|---|
| D1 | Me | benzo[d]oxazol-2-yl | trans, racemic | 350.0 |
| D2 | Me | 3-cyclobutyl-1,2,4-oxadiazol-5-yl | trans, racemic | 355.1 |
| D3 | Me | 3-(5-fluoropyridin-3-yl)-1,2,4-oxadiazol-5-yl | trans, racemic | 396.1 |

TABLE EX-D-continued

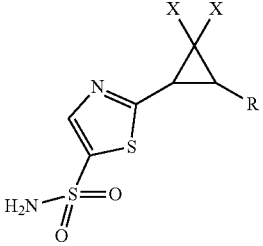

| Example | X | R | Stereochemistry Comment | MS [M + H] |
|---|---|---|---|---|
| D4 | Me | 5-(3-phenyl-1,2,4-oxadiazol) | trans, racemic | 377.1 |
| D5 | Me | 5-(3-isopropyl-1,2,4-oxadiazol) | trans, racemic | 343.2 |
| D6 | Me | 5-(3-(3,3-difluorocyclobutyl)-1,2,4-oxadiazol) | trans, racemic | 391.1 |
| D7 | Me | 5-(3-(2-methoxy-5-chlorophenyl)-1,2,4-oxadiazol) | trans, racemic | 441.1 |
| D8 | H | 5-(3-phenyl-1,2,4-oxadiazol) | trans, racemic | 349.1 |
| D9 | Me | 5-(3-phenyl-1,2,4-oxadiazol) | R,R | 377.1 |

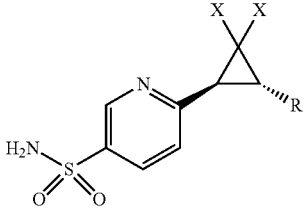

| Example | X | R | MS [M + H] |
|---|---|---|---|
| E1 | Me | 5-(3-(3-fluorophenyl)-1,2,4-oxadiazol) | 389.1 |
| E2 | Me | 5-(3-cyclopentyl-1,2,4-oxadiazol) | 363.2 |

TABLE EX-E-continued

Structure: pyridine with sulfonamide (H2N-SO2-) at one position and a cyclopropyl group (with two X substituents on one carbon and R on the adjacent carbon) at another position.

| Example | X | R | MS [M + H] |
|---|---|---|---|
| E3 | Me | 5-(3-phenyl-1,2,4-oxadiazol-5-yl) | 371.1 |
| E4 | Me | 5-[3-(2-methoxy-5-chlorophenyl)-1,2,4-oxadiazol-5-yl] | 435.1 |
| E5 | Me | 5-[3-(2,4-difluorophenyl)-1,2,4-oxadiazol-5-yl] | 407.1 |
| E6 | Me | 5-[3-(3-trifluoromethylphenyl)-1,2,4-oxadiazol-5-yl] | 439.1 |
| E7 | Me | 5-(3-cyclohexyl-1,2,4-oxadiazol-5-yl) | 377.2 |

TABLE EX-F

Same core structure as above.

| Example | X | R | MS [M + H] |
|---|---|---|---|
| F1 | Me | 5-[3-(3-fluorophenyl)-1,2,4-oxadiazol-5-yl] | 389.1 |
| F2 | Me | 5-[3-(5-trifluoromethylpyridin-3-yl)-1,2,4-oxadiazol-5-yl] | 440.1 |
| F3 | Me | 5-(3-cyclopentyl-1,2,4-oxadiazol-5-yl) | 363.1 |
| F4 | Me | 5-[3-(2-methoxy-5-chlorophenyl)-1,2,4-oxadiazol-5-yl] | 435.1 |
| F5 | Me | 5-[3-(2,4-difluorophenyl)-1,2,4-oxadiazol-5-yl] | 407.1 |
| F6 | Me | 5-[3-(3-trifluoromethylphenyl)-1,2,4-oxadiazol-5-yl] | 439.1 |
| F7 | Me | 5-[3-(cyclopropylmethyl)-1,2,4-oxadiazol-5-yl] | 349.1 |
| F8 | Me | 5-(3-cyclopropyl-1,2,4-oxadiazol-5-yl) | 335.1 |
| F9 | Me | 5-(3-tert-butyl-1,2,4-oxadiazol-5-yl) | 351.1 |
| F10 | Me | 5-(3-phenyl-1,2,4-oxadiazol-5-yl) | 371.1 |

TABLE EX-F-continued

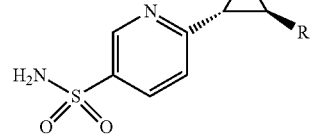

| Example | X | R | MS [M + H] |
|---|---|---|---|
| F11 | Me | (5-fluoropyridin-3-yl)-1,2,4-oxadiazol-5-yl | 390.1 |
| F12 | Me | (3,3-difluorocyclobutyl)-1,2,4-oxadiazol-5-yl | 385.1 |
| F13 | Me | (cyclobutyl)-1,2,4-oxadiazol-5-yl | 349.1 |
| F14 | Me | (isopropyl)-1,2,4-oxadiazol-5-yl | 337.1 |

TABLE EX-G

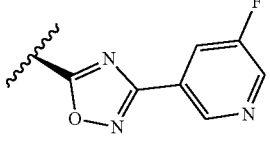

| Example | X | R | Stereochemistry Comment | MS [M + H] |
|---|---|---|---|---|
| G1 | Me | benzoxazol-2-yl | trans, racemic | 343.4 |
| G2 | Me | (3-phenyl)-1,2,4-oxadiazol-5-yl | trans, racemic | 371.2 |

TABLE EX-G-continued

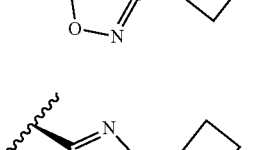

| Example | X | R | Stereochemistry Comment | MS [M + H] |
|---|---|---|---|---|
| G3 | Me | (1-methyl)-1,2,4-oxadiazol-5-yl with Me | trans, racemic | 337.2 |
| G4 | Me | (cyclobutyl)-1,2,4-oxadiazol-5-yl | trans, racemic | 349.2 |
| G5 | Me | (3,3-difluorocyclobutyl)-1,2,4-oxadiazol-5-yl | trans, racemic | 385.2 |
| G6 | H | (3-phenyl)-1,2,4-oxadiazol-5-yl | trans, racemic | 343.1 |
| G7 | H | (cyclopentyl)-1,2,4-oxadiazol-5-yl | trans, racemic | 335.1 |

The utility of the compounds in accordance with the present invention as positive allosteric modulators of α7 nicotinic acetylcholine receptor activity may be demonstrated by methodology known in the art. Direct activation of α7 (agonism), and potentiation of acetylcholine-evoked α7 currents was determined as follows:

Automated Patch-Clamp Electrophysiology Functional Assay (Assay A)

Automated patch-clamp electrophysiology was performed using the IonFlux HT (Fluxion Biosciences Inc., San Francisco, Calif.) in the whole-cell, population patch configuration. Test compounds were assessed for their ability to modulate the function of the α7 nicotinic acetylcholine receptor both in the presence, and in the absence of the natural α7 agonist acetylcholine. A HEK cell line stably expressing both human RIC-3 and human α7 (PrecisION hnAChR α7/RIC-3, Eurofins Pharma, St. Charles, Mo.) was cultured in 175 cm² triple-layer tissue culture flasks to no more than 90% confluency in DMEM/F-12 growth media supplemented with 10% heat-inactivated fetal bovine serum, 1% non-essential amino acids, 0.625 μg/mL Puromycin, and 400 μg/mL Geneticin. Immediately prior to assay, cells were detached by first aspirating growth media, rinsing with Dulbecco's phosphate buffered saline, and then adding 10 mL of Accutase (Innovative Cell Technologies, San Diego, Calif.) to the flask and then incubating at 37° C. for 5 minutes. Detached cells were then recovered by the addition of 40 mL of CHO-serum-free media supplemented with 25 mM HEPES, and rocked gently in a 50 mL conical tube for 20 minutes prior to patch-clamp assay. After recovery, cells were pelleted by centrifugation at 1,000 RPM for 1 minute in a compact bench top centrifuge; recovery media was aspirated and cells were resuspended in external recording solution (150 mM NaCl, 5 mM KCl, 2 mM $CaCl_2$, 1 mM $MgCl_2$, 10 mM HEPES, 12 mM dextrose) to a density of $5.0 \times 10^6$ cells/mL. The cell suspension was added to the cell inlet wells on an IonFlux HT population patch plate which had previously been rinsed and primed with deionized $H_2O$. Test compounds were serially diluted in DMSO and then resuspended to the final test concentration in external recording solution, with, or without 40 µM acetylcholine added to the external recording solution; test compounds were then transferred to the IonFlux HT population patch plate. Internal recording solution (110 mM $TrisPO_4$, 28 mM TrisBase, 0.1 mM $CaCl_2$, 2 mM $MgCl_2$, 11 mM EGTA, 4 mM MgATP) was added to the internal recording solution inlet wells on the IonFlux HT patch plate previously loaded with cells and test compounds, and the plate loaded into the IonFlux HT instrument. A protocol was executed on the IonFlux HT to trap the cells, break into the cells, and establish the whole-cell recording configuration; cells were voltage-clamped at a holding potential of −60 mV for the duration of the experiment, all experiments were conducted at room temperature, and the IonFlux HT injection pressure was 8 psi for solution applications. Upon establishing the whole-cell configuration, external recording solution was perfused into the recording chambers for 120 seconds and then 40 µM acetylcholine was applied for 1 second and immediately washed off with external recording solution for 60 seconds. The 40 µM acetylcholine-evoked α7 current served as the current response to which subsequent test compound effects, in the presence, or in the absence of 40 µM acetylcholine would be quantified relative to. Next, test compounds were evaluated at multiple concentrations for their ability to induce, or modulate α7 current responses; three concentrations of test compound were evaluated in ascending dose fashion per recording. To assess test compound agonist activity, test compound diluted in external recording solution was applied starting from the lowest concentration of test compound being tested in the concentration series, for 58 seconds; the first 20 seconds of the 58 second compound application period coincided with a data collection sweep which was 20 seconds in duration, and collected at a rate of 5,000 samples/second. To assess test compound positive allosteric modulator activity, immediately following the 58 second test compound only application period, the same concentration of test compound, diluted in external recording solution containing 40 µM acetylcholine was applied for 1 second; in this way, the test compound and the natural receptor agonist acetylcholine were co-applied, and potentiating effects of test compounds observed. The 1 second application of test compound diluted in external solution containing 40 µM acetylcholine coincided with a data collection sweep which was 20 seconds in duration, and collected at a rate of 5,000 samples/second, after which, external recording solution only was applied for 42 seconds. Following this 42 second wash with external recording solution only, the next highest concentration of the test compound in the concentration series was applied in the absence and then in the presence of acetylcholine as previously described, and data collected as previously described. After test compound agonist, and positive allosteric modulator activity were assessed at three ascending concentrations, the experiment was terminated and leak subtraction performed using the IonFlux HT data analysis software. Peak current amplitudes and the area under the curve (AUC) were both quantified for each current sweep using proprietary software and test compound effects where quantified as follows.

Test compound agonist activity was calculated as:

% Agonism=$(Y/X) \times 100$

Test compound potentiator activity was calculated as:

% Potentiation=$[(Z/X) \times 100]-100$

X=Peak current amplitude (or AUC) evoked by 40 µM acetylcholine
Y=Peak current amplitude (or AUC) evoked by test compound diluted in external recording solution
Z=Peak current amplitude (or AUC) evoked by test compound diluted in external recording solution containing 40 µM acetylcholine As such, test compounds which evoked the same current amplitude as 40 µM acetylcholine alone would exhibit a calculated % Agonism of 100%. Test compounds co-applied with 40 µM acetylcholine which evoked a current amplitude 2× the current evoked from 40 µM acetylcholine alone would exhibit a calculated % Potentiation of 100%, whereas test compounds co-applied with 40 µM acetylcholine which evoked the same current amplitude as 40 µM acetylcholine alone would be characterized as exhibiting no potentiation.

Agonist and potentiation data, derived by peak current amplitude or area under the curve (AUC) were graphed and fit using a 4-parameter logistic fit based on the Levenberg-Marquardt algorithm where y=A+((B−A)/(1+((C/x)^D))) where:
A=Minimum
B=Maximum
C=$EC_{50}$
D=Slope
x=test compound concentration
y=% Agonism or % Potentiation Potency data for selected compounds of the present invention in the automated patch-clamp electrophysiology functional assay (Assay A) are represented in the table below:

| Example | α7 nAChR Potency |
| --- | --- |
| 1 | B |
| 2 | B |
| 3 | B |
| 4 | B |
| 5 | C |
| 6 | C |
| 7 | C |
| 8 | C |
| 9 | C |
| 10 | B |
| 11 | C |
| 12 | C |
| 13 | C |
| A1 | C |
| A2 | C |
| A3 | C |
| A4 | C |
| A5 | C |
| A6 | C |
| A7 | C |
| A8 | C |
| A9 | C |
| A10 | C |

| Example | α7 nAChR Potency |
| --- | --- |
| A11 | C |
| A12 | C |
| A13 | C |
| A14 | C |
| A15 | C |
| B1 | B |
| B2 | C |
| B3 | C |
| B4 | C |
| B5 | C |
| B6 | B |
| B7 | B |
| B8 | C |
| B9 | C |
| B10 | C |
| B11 | C |
| B12 | C |
| B13 | C |
| B14 | C |
| B15 | C |
| B16 | C |
| C1 | C |
| C2 | C |
| C3 | B |
| C4 | D |
| C5 | C |
| C6 | C |
| C7 | C |
| C8 | B |
| C9 | C |
| C10 | C |
| C11 | C |
| C12 | C |
| C13 | C |
| D1 | C |
| D2 | C |
| D3 | C |
| D4 | B |
| D5 | C |
| D6 | D |
| D7 | C |
| D8 | C |
| D9 | C |
| E1 | C |
| E2 | C |
| E3 | C |
| E4 | D |
| E5 | C |
| E6 | C |
| E7 | C |
| F1 | C |
| F2 | C |
| F3 | B |
| F4 | C |
| F5 | C |
| F6 | C |
| F7 | C |
| F8 | C |
| F9 | C |
| F10 | C |
| F11 | C |
| F12 | C |
| F13 | C |
| F14 | C |
| G1 | C |
| G2 | C |
| G3 | C |
| G4 | C |
| G5 | C |
| G6 | C |
| G7 | C |

*Potency defined as A ($EC_{50} \leq 0.1$ μM); B (0.1 μM < $EC_{50} \leq 0.5$ μM); C (0.5 μM < $EC_{50} \leq 5$ μM); D (5 μM < $EC_{50} \leq 50$ μM)

Electrophysiology $EC_{50}$ values for selected compounds of the present invention in the automated patch-clamp electrophysiology functional assay (Assay A) are provided in the table below:

| Example | α7 nAChR $EC_{50}$ (nM) |
| --- | --- |
| 1 | 450 |
| 2 | 480 |
| 3 | 380 |
| 4 | 400 |
| 5 | 3400 |
| 6 | 590 |
| 7 | 640 |
| 8 | 1500 |
| 9 | 720 |
| 10 | 480 |
| 11 | 990 |
| 12 | 1100 |
| 13 | 770 |
| A1 | 1500 |
| A2 | 1400 |
| A3 | 2900 |
| A4 | 3200 |
| A5 | 690 |
| A6 | 1500 |
| A7 | 650 |
| A9 | 5000 |
| A11 | 3000 |
| A14 | 570 |
| A15 | 1600 |
| B1 | 310 |
| B2 | 1700 |
| B4 | 2500 |
| B5 | 3000 |
| B7 | 370 |
| B9 | 620 |
| B10 | 1600 |
| B12 | 1600 |
| B14 | 590 |
| B15 | 1100 |
| B16 | 1500 |
| C1 | 580 |
| C2 | 920 |
| C3 | 430 |
| C4 | 5100 |
| C5 | 1100 |
| C7 | 1600 |
| C8 | 390 |
| C10 | 2100 |
| C11 | 1500 |
| C12 | 1200 |
| C13 | 1100 |
| D1 | 2000 |
| D2 | 1200 |
| D3 | 1600 |
| D4 | 360 |
| D5 | 4200 |
| D7 | 1200 |
| D8 | 1000 |
| D9 | 1700 |
| E1 | 4000 |
| E2 | 3200 |
| E4 | 5400 |
| E5 | 1300 |
| F1 | 1100 |
| F2 | 3300 |
| F3 | 340 |
| F5 | 1700 |
| F6 | 2700 |
| F7 | 1500 |
| F8 | 1400 |
| F10 | 1100 |
| F11 | 3400 |
| F12 | 1900 |
| F14 | 1600 |
| G1 | 900 |
| G2 | 970 |

-continued

| Example | α7 nAChR EC$_{50}$ (nM) |
|---|---|
| G5 | 3600 |
| G6 | 1300 |
| G7 | 3000 |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A compound having the formula I:

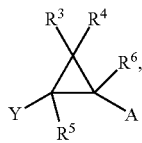
(I)

or a pharmaceutically acceptable salt thereof, wherein:

Y is selected from

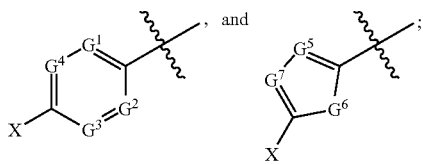
, and

X is selected from

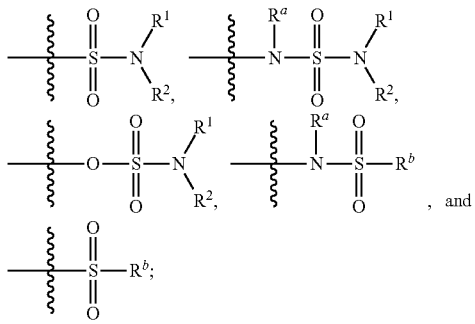
, and $G^1$ is $CR^9$, or N;
$G^2$ is $CR^9$, or N;
$G^3$ is $CR^9$, or N;
$G^4$ is is $CR^9$, or N;
provided that at least one of $G^1$-$G^4$ is N and at least two of $G^1$-$G^4$ are $CR^9$;
$G^5$ is $CR^9$, or N;
$G^6$ is O, or S;
$G^7$ is $CR^9$, or N;
A is heteroaryl which is optionally substituted with 1 to 4 R groups each independently selected from OH, oxo, amino, amido, carboxyl, keto, cyano, alkoxy, $S(O)_m$-alkyl, halogen, aminoalkyl, hydroxyalkyl, alkyl, cycloalkyl, alkynyl, aryl, heteroaryl, and heterocyclyl, wherein said amino, amido, carboxyl, keto, alkoxy, $S(O)_m$-alkyl, aminoalkyl, hydroxyalkyl, alkyl, cycloalkyl, alkynyl, aryl, heteroaryl and heterocyclyl are optionally substituted with one or more substituents independently selected from halogen, OH, oxo, $CF_3$, $OCF_3$, CN, $(C_1-C_6)$alkyl, $O(C_1-C_4)$alkyl, $S(O)_m$-$(C_1-C_4)$alkyl, $C=O(C_1-C_4)$alkyl, $(C=O)NR^7R^8$, $(C=O)OR^7$, $(C_2-C_4)$alkynyl, $(C_3-C_6)$cycloalkyl, $O(C_3-C_6)$cycloalkyl, $C=O(C_3-C_6)$cycloalkyl, aryl, heteroaryl and heterocyclyl, wherein said alkyl, cycloalkyl, aryl, heteroaryl and heterocyclyl are optionally independently substituted with one or more halogen, $CF_3$, OH and oxo;

$R^1$ is H or $(C_1-C_4)$alkyl;
$R^2$ is H or $(C_1-C_4)$alkyl;
$R^3$ is H, halogen, $(C_1-C_4)$alkyl, wherein said alkyl is optionally substituted with one or more halogen;
$R^4$ is H, halogen or $(C_1-C_4)$alkyl, wherein said alkyl is optionally substituted with one or more halogen;
or, $R^3$ and $R^4$ optionally can come to together to form a cyclopropyl, cyclobutyl, cyclopentyl or cyclohexyl ring wherein said ring may be optionally substituted with one or more substituents independently selected from OH, halogen, or $(C_1-C_4)$alkyl;
$R^5$ is H or $(C_1-C_4)$alkyl;
$R^6$ is H or $(C_1-C_4)$alkyl;
$R^7$ and $R^8$ are independently selected from H, $(C_1-C_6)$alkyl, cycloalkyl, aryl, heteroaryl and heterocyclyl, wherein said alkyl, cycloalkyl, aryl, heteroaryl and heterocyclyl are optionally substituted with one or more substituents independently selected from halogen, OH, $CF_3$, $(C_1-C_4)$alkyl, $O(C_1-C_4)$alkyl, cycloalkyl, CN, aryl, heteroaryl, and heterocyclyl, wherein said alkyl, cycloalkyl, aryl, heteroaryl and heterocyclyl are optionally substituted with one or more substituents independently selected from halogen, OH, $CF_3$, $(C_1-C_4)$alkyl, $O(C_1-C_4)$alkyl, and CN;
$R^9$ is H or $(C_1-C_4)$alkyl;
$R^a$ is H or $(C_1-C_4)$alkyl;
$R^b$ is H or $(C_1-C_4)$alkyl; and
m is 0, 1, or 2.

2. The compound of claim 1, or a pharmaceutically acceptable salt thereof, wherein X is

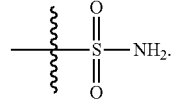 [SMILES: *S(N)(=O)=O]

3. The compound according to claim 2, or a pharmaceutically acceptable salt thereof, wherein $R^9$ is H or methyl.

4. The compound according to claim 3, or a pharmaceutically acceptable salt thereof, wherein A is heteroaryl which is optionally substituted with 1 to 3 R groups independently selected from halogen, CN, $(C_1-C_6)$alkyl, $O(C_1-C_6)$alkyl, $NR^7R^8$, $(C_3-C_6)$cycloalkyl, aryl, heteroaryl and heterocyclyl, wherein said alkyl, $NR^7R^8$, $(C_3-C_6)$cycloalkyl, aryl, heteroaryl and heterocyclyl are optionally substituted with one or more substituents independently selected from halogen, CN, $(C_1-C_4)$alkyl, $(C=O)O(C_1-C_4)$alkyl and phenyl, wherein said alkyl is optionally substituted with one or more halogen.

5. The compound according to claim 4, or a pharmaceutically acceptable salt thereof, wherein $R^5$, $R^6$, $R^a$ and $R^b$ are independently H or methyl.

6. The compound according to claim 5, or a pharmaceutically acceptable salt thereof, wherein $R^3$ and $R^4$ are independently H, F, or methyl.

7. The compound according to claim 6, or a pharmaceutically acceptable salt thereof, wherein $R^7$ and $R^8$ are independently selected from H, $(C_1-C_6)$alkyl, cyclopentyl and phenyl wherein said alkyl and phenyl are optionally substituted with halogen or phenyl.

8. The compound of claim 1 having the formula:

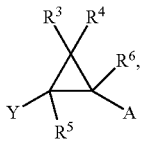
(I)

or a pharmaceutically acceptable salt thereof, wherein:
Y is selected from

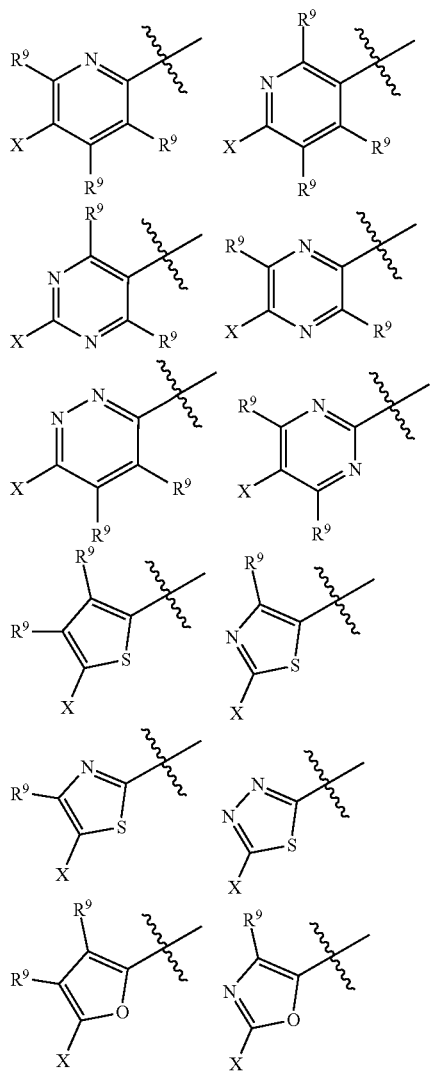

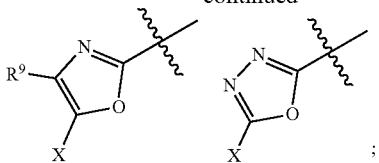

X is

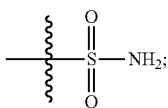

A is selected from oxazolyl, thiazolyl, oxadiazolyl, thiadiazolyl, isoxazolyl, benzoxazolyl, isothiazolyl, triazolyl, pyrazolyl, quinazolinyl, oxazolopyridinyl, quinoxalinyl, imidazopyridazinyl, benzothiazolyl, naphthyridinyl, pyrazolopyridinyl, cinnolinyl, isoquinolyl, thienopyridinyl, indazolyl, furopyridinyl, pyridinyl, pyrimidinyl, pyridazinyl and pyrazinyl each optionally substituted with 1-2 R groups independently selected from $(C_1-C_6)$alkyl, $O(C_1-C_6)$alkyl, $NR^7R^8$, $(C_3-C_6)$cycloalkyl, aryl, heteroaryl and heterocyclyl, wherein each are optionally substituted with one or more substituents independently selected from halogen, $CF_3$, CN, $(C_1-C_4)$alkyl, $O(C_1-C_6)$alkyl, $(C=O)O(C_1-C_4)$alkyl and phenyl;

$R^3$ is H or methyl;
$R^4$ is H or methyl;
$R^5$ is H or methyl;
$R^6$ is H or methyl;
$R^7$ and $R^8$ are independently selected from H, $(C_1-C_6)$alkyl, $(C_3-C_6)$cycloalkyl, aryl, heteroaryl and heterocyclyl; and
$R^9$ is independently H or methyl.

9. The compound of claim 8 having the formula I, or a pharmaceutically acceptable salt thereof, wherein;
Y is selected from

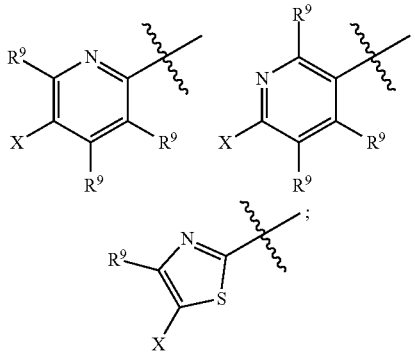

X is

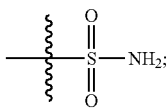 [SMILES: *S(N)(=O)=O]

A is selected from oxazolyl, thiazolyl, oxadiazolyl, thiadiazolyl, isoxazolyl, and benzoxazolyl, each optionally substituted with 1 R group selected from $(C_1$-$C_6)$alkyl, $O(C_1$-$C_6)$alkyl, $NR^7R^8$, $(C_3$-$C_6)$cycloalkyl, phenyl, pyridinyl, morpholinyl, imidazolyl, pyrazolyl, oxadiazolyl, pyrrolidinyl, piperazinyl, triazolyl and tetrahydropyranyl wherein each are optionally substituted with one or more substituents independently selected from halogen, $CF_3$, CN, $(C_1$-$C_4)$alkyl, $O(C_1$-$C_6)$alkyl, $(C_3$-$C_6)$cycloalkyl, $(C=O)O(C_1$-$C_4)$alkyl and phenyl;

$R^3$ is H or methyl;
$R^4$ is H or methyl;
$R^5$ is H or methyl;
$R^6$ is H or methyl;
$R^7$ and $R^8$ are independently selected from H, $(C_1$-$C_6)$ alkyl, cyclopentyl and phenyl, wherein each alkyl, cyclopentyl, and phenyl are optionally substituted with one or more substituents independently selected from halogen and phenyl; and
$R^9$ is H or methyl.

10. The compound of claim 1 which is selected from the group consisting of
5-[trans-3-(1,3-Benzoxazol-2-yl)-2,2-dimethylcyclopropyl]pyridine-2-sulfonamide;
5-{trans-3-[5-(2,4-Difluorophenyl)-1,3,4-thiadiazol-2-yl]-2,2-dimethylcyclopropyl}pyridine-2-sulfonamide;
5-[(1S,3S)-2,2-Dimethyl-3-(3-phenyl-1,2,4-oxadiazol-5-yl)cyclopropyl]pyridine-2-sulfonamide;
5-[trans-2-(3-Phenyl-1,2,4-oxadiazol-5-yl)cyclopropyl]pyridine-2-sulfonamide;
6-Methyl-5-[trans-2-(3-phenyl-1,2,4-oxadiazol-5-yl)cyclopropyl]pyridine-2-sulfonamide;
2-[(1S,3S)-2,2-Dimethyl-3-(3-phenyl-1,2,4-oxadiazol-5-yl)cyclopropyl]-1,3-thiazole-5-sulfonamide;
5-[(1R,3R)-3-(3-Cyclohexyl-1,2,4-oxadiazol-5-yl)-2,2-dimethylcyclopropyl]pyridine-2-sulfonamide;
5-[(1S,3S)-2,2-Dimethyl-3-(5-phenyl-1,3-oxazol-2-yl)cyclopropyl]pyridine-2-sulfonamide;
5-[(1R,3R)-3-(5-Cyclopentyl-1,3-thiazol-2-yl)-2,2-dimethylcyclopropyl]pyridine-2-sulfonamide;
6-[(1S,3S)-3-(3-Cyclohexyl-1,2,4-oxadiazol-5-yl)-2,2-dimethylcyclopropyl]pyridine-3-sulfonamide;
5-[trans-2,2-Dimethyl-3-(5-phenyl-1,2,4-oxadiazol-3-yl)cyclopropyl]pyridine-2-sulfonamide;
5-[trans-3-(3-Cyclopentylisoxazol-5-yl)-2,2-dimethylcyclopropyl]pyridine-2-sulfonamide;
5-{trans-3-[5-(3-Fluorophenyl)isoxazol-3-yl]-2,2-dimethylcyclopropyl}pyridine-2-sulfonamide;
5-[(1R,3R)-2,2-Dimethyl-3-(3-phenyl-1,2,4-oxadiazol-5-yl)cyclopropyl]pyridine-2-sulfonamide;
5-[(1R,3R)-2,2-Dimethyl-3-{[5-(trifluoromethyl)pyridin-3-yl]-1,2,4-oxadiazol-5-yl}cyclopropyl]pyridine-2-sulfonamide;
5-[(1R,3R)-3-(3-Cyclopentyl-1,2,4-oxadiazol-5-yl)-2,2-dimethylcyclopropyl]pyridine-2-sulfonamide;
5-[(1R,3R)-3-(5-Cyclopentyl-1,3-oxazol-2-yl)-2,2-dimethylcyclopropyl]pyridine-2-sulfonamide;
5-[(1R,3R)-2,2-Dimethyl-3-(5-phenyl-1,3-thiazol-2-yl)cyclopropyl]pyridine-2-sulfonamide;
5-{(1R,3R)-3-[3-(5-Chloro-2-methoxyphenyl)-1,2,4-oxadiazol-5-yl]-2,2-dimethylcyclopropyl}pyridine-2-sulfonamide;
5-{(1R,3R)-3-[3-(3-Fluorophenyl)-1,2,4-oxadiazol-5-yl]-2,2-dimethylcyclopropyl}pyridine-2-sulfonamide;
5-{(1R,3R)-3-[3-(2,4-Difluorophenyl)-1,2,4-oxadiazol-5-yl]-2,2-dimethylcyclopropyl}pyridine-2-sulfonamide;
5-{(1R,3R)-3-[3-(5-Fluoropyridin-3-yl)-1,2,4-oxadiazol-5-yl]-2,2-dimethylcyclopropyl}pyridine-2-sulfonamide;
5-[(1R,3R)-2,2-Dimethyl-3-{3-[3-(trifluoromethyl)phenyl]-1,2,4-oxadiazol-5-yl}cyclopropyl]pyridine-2-sulfonamide;
5-{(1R,3R)-3-[3-(3,3-Difluorocyclobutyl)-1,2,4-oxadiazol-5-yl]-2,2-dimethylcyclopropyl}pyridine-2-sulfonamide;
5-[(1R,3R)-3-(3-Cyclobutyl-1,2,4-oxadiazol-5-yl)-2,2-dimethylcyclopropyl]pyridine-2-sulfonamide;
5-{(1R,3R)--[3-(Cyclopropylmethyl)-1,2,4-oxadiazol-5-yl]-2,2-dimethylcyclopropyl}pyridine-2-sulfonamide;
5-{(1R,3R)-2,2-Dimethyl-3[3-(propan-2-yl)-1,2,4-oxadiazol-5-yl]cyclopropyl}pyridine-2-sulfonamide;
5-[(1R,3R)-2,2-Dimethyl-3-(5-phenyl-1,3-oxazol-2-yl)cyclopropyl]pyridine-2-sulfonamide;
5-{(1S,3S)-3-[3-(3-Fluorophenyl)-1,2,4-oxadiazol-5-yl]-2,2-dimethylcyclopropyl}pyridine-2-sulfonamide;
5-{(1S,3S)-3[3-(5-Chloro-2-methoxyphenyl)-1,2,4-oxadiazol-5-yl]-2,2-dimethylcyclopropyl}pyridine-2-sulfonamide;
5-{(1S,3S)-3[3-(2,4-Difluorophenyl)-1,2,4-oxadiazol-5-yl]-2,2-dimethylcyclopropyl}pyridine-2-sulfonamide;
5-[(1S,3S)-2,2-Dimethyl-3-{3-[5-(trifluoromethyl)pyridin-3-yl]-1,2,4-oxadiazol-5-yl}cyclopropyl]pyridine-2-sulfonamide;
5-[(1S,3S)-2,2-Dimethyl-3-{3-[3-(trifluoromethyl)phenyl]-1,2,4-oxadiazol-5-yl}cyclopropyl]pyridine-2-sulfonamide;
5-[(1S,3S)-3-(3-Cyclohexyl-1,2,4-oxadiazol-5-yl)-2,2-dimethylcyclopropyl]pyridine-2-sulfonamide;
5-[(1S,3S)-3-(3-Cyclopentyl-1,2,4-oxadiazol-5-yl)-2,2-dimethylcyclopropyl]pyridine-2-sulfonamide;
5-{(1S,3S)-3-[3-(3,3-Difluorocyclobutyl)-1,2,4-oxadiazol-5-yl]-2,2-dimethylcyclopropyl}pyridine-2-sulfonamide;
5-[(1S,3S)-3 -(3-Cyclobutyl- 1,2,4-oxadiazol-5-yl)-2,2-dimethylcyclopropyl]pyridine-2-sulfonamide;
5-{(1S,3S)-3-[3(Cyclopropylmethyl)-1,2,4-oxadiazol-5-yl]-2,2-dimethylcyclopropyl}pyridine-2-sulfonamide;
5-[(1S,3S)-3-(3-Cyclopropyl-1,2,4-oxadiazol-5-yl)-2,2-dimethylcyclopropyl]pyridine-2-sulfonamide;
5-[(1S,3S)-3-(3-tert-Butyl-1,2,4-oxadiazol-5-yl)-2,2-dimethylcyclopropyl]pyridine-2-sulfonamide;
5-{(1S,3S)-2,2-Dimethyl-3-[3(propan-2-yl)-1,2,4-oxadiazol-5-yl]cyclopropyl}pyridine-2-sulfonamide;
5-[(1S,3S)-3-(5-Cyclopentyl-1,3-oxazol-2-yl)-2,2-dimethylcyclopropyl]pyridine-2-sulfonamide;
5-[(1S,3S)-2,2-Dimethyl-3-(5-phenyl- 1,3-thiazol-2-yl)cyclopropyl]pyridine-2-sulfonamide;
5-[(1S,3S)-3-(5-Cyclopentyl-1,3-thiazol-2-yl)-2,2-dimethylcyclopropyl]pyridine-2-sulfonamide; 5-{trans-2,2-Dimethyl-3-[5-(2,3,6-trifluorophenyl)-1,2,4-oxadiazol-3-yl]cyclopropyl}pyridine-2-sulfonamide;
5-[trans-3-(5-Cyclopentyl-1,2,4-oxadiazol-3-yl)-2,2-dimethylcyclopropyl]pyridine-2-sulfonamide;
5-{trans-3-[3-(3-Fluorophenyl)isoxazol-5-yl]-2,2-dimethylcyclopropyl}pyridine-2-sulfonamide;
5-[trans-3-(1,3-Benzoxazol-2-yl)-2,2-dimethylcyclopropyl]pyridine-2-sulfonamide;
5-[trans-2-(3-Phenyl-1,2,4-oxadiazol-5-yl)cyclopropyl]pyridine-2-sulfonamide;
5-[trans-2,2-Dimethyl-3-(3-phenyl-1,2,4-oxadiazol-5-yl)cyclopropyl]pyridine-2-sulfonamide;
5-[trans-3-(1,3-Benzoxazol-2-yl)-2,2-dimethylcyclopropyl]pyridine-2-sulfonamide;

5-{trans-2-[3-(3-Fluorophenyl)-1,2,4-oxadiazol-5-yl]cyclopropyl}pyridine-2-sulfonamide;
5-[trans-2-(3-Cyclopentyl-1,2,4-oxadiazol-5-yl)cyclopropyl]pyridine-2-sulfonamide;
5-[trans-3-(5-Cyclohexyl-1,2,4-oxadiazol-3-yl)-2,2-dimethylcyclopropyl]pyridine-2-sulfonamide;
5-(trans-2,2-Dimethyl-3-{5-[1-(trifluoromethyl)cyclopropyl]-1,2,4-oxadiazol-3-yl}cyclopropyl)pyridine-2-sulfonamide;
5-{trans-3-[5-(2,6-Difluorophenyl)-1,2,4-oxadiazol-3-yl]-2,2-dimethylcyclopropyl}pyridine-2-sulfonamide;
5-{trans-3-[5-(3-Fluorophenyl)isoxazol-3-yl]-2,2-dimethylcyclopropyl}pyridine-2-sulfonamide;
2-[trans-3-(1,3-Benzoxazol-2-yl)-2,2-dimethylcyclopropyl]-1,3-thiazole-5-sulfonamide;
2-[trans-3-(3-Cyclobutyl-1,2,4-oxadiazol-5-yl)-2,2-dimethylcyclopropyl]-1,3-thiazole-5-sulfonamide;
2-{trans-3-[3-(5-Fluoropyridin-3-yl)-1,2,4-oxadiazol-5-yl]-2,2-dimethylcyclopropyl}-1,3-thiazole-5-sulfonamide;
2-[trans-2,2-Dimethyl-3-(3-phenyl-1,2,4-oxadiazol-5-yl)cyclopropyl]-1,3-thiazole-5-sulfonamide;
2-{trans-2,2-Dimethyl-3-[3-(propan-2-yl)-1,2,4-oxadiazol-5-yl]cyclopropyl}-1,3-thiazole-5-sulfonamide;
2-{trans-3-[3-(3,3-Difluorocyclobutyl)-1,2,4-oxadiazol-5-yl]-2,2-dimethylcyclopropyl}-1,3-thiazole-5-sulfonamide;
2-{trans-3-[3-(5-Chloro-2-methoxyphenyl)-1,2,4-oxadiazol-5-yl]-2,2-dimethylcyclopropyl}-1,3-thiazole-5-sulfonamide;
2-[trans-2-(3-Phenyl-1,2,4-oxadiazol-5-yl)cyclopropyl]-1,3-thiazole-5-sulfonamide;
2-[(1R,3R)-2,2-Dimethyl-3-(3-phenyl-1,2,4-oxadiazol-5-yl)cyclopropyl]-1,3-thiazole-5-sulfonamide;
6-{(1R,3R)-3-[3-(3-Fluorophenyl)-1,2,4-oxadiazol-5-yl]-2,2-dimethylcyclopropyl}pyridine-3-sulfonamide;
6-[(1R,3R)-3-(3-Cyclopentyl-1,2,4-oxadiazol-5-yl)-2,2-dimethylcyclopropyl]pyridine-3-sulfonamide;
6-[(1R,3R)-2,2-Dimethyl-3-(3-phenyl-1,2,4-oxadiazol-5-yl)cyclopropyl]pyridine-3-sulfonamide
6-{(1R,3R)-3-[3-(5-Chloro-2-methoxyphenyl)-1,2,4-oxadiazol-5-yl]-2,2-dimethylcyclopropyl}pyridine-3-sulfonamide;
6-{(1R,3R)-3-[3(2,4-Difluorophenyl)-1,2,4-oxadiazol-5-yl]-2,2-dimethylcyclopropyl}pyridine-3-sulfonamide;
6-[(1R,3R)-2,2-Dimethyl-3-{3-[3-(trifluoromethyl)phenyl]-1,2,4-oxadiazol-5-yl}cyclopropyl]pyridine-3-sulfonamide;
6-[(1R,3R)-3-(3-Cyclohexyl-1,2,4-oxadiazol-5-yl)-2,2-dimethylcyclopropyl]pyridine-3-sulfonamide;
6- {(1S,3S)-3-[3-(3-Fluorophenyl)-1,2,4-oxadiazol-5-yl]-2,2-dimethylcyclopropyl}pyridine-3-sulfonamide;
6-[(1S,3S)-2,2-Dimethyl-3-{3-[5-(trifluoromethyl)pyridin-3-yl]-1,2,4-oxadiazol-5-yl}cyclopropyl]pyridine-3-sulfonamide;
6-[(1S,3S)-3-(3-Cyclopentyl-1,2,4-oxadiazol-5-yl)-2,2-dimethylcyclopropyl]pyridine-3-sulfonamide.
6-{(1S,3S)-3-[3-(5-Chloro-2-methoxyphenyl)-1,2,4-oxadiazol-5-yl]-2,2-dimethylcyclopropyl}pyridine-3-sulfonamide;
6-{(1S,3S)-3-[3-(2,4-Difluorophenyl)-1,2,4-oxadiazol-5-yl]-2,2-dimethylcyclopropyl}pyridine-3-sulfonamide;
6-[(1S,3S)-2,2-Dimethyl-3-{3-[3-(trifluoromethyl)phenyl]-1,2,4-oxadiazol-5-yl}cyclopropyl]pyridine-3-sulfonamide;
6-{(1S,3S)-3-[3-(Cyclopropylmethyl)-1,2,4-oxadiazol-5-yl]-2,2-dimethylcyclopropyl}pyridine-3-sulfonamide;
6-[(1S,3S)-3-(3-Cyclopropyl-1,2,4-oxadiazol-5-yl)-2,2-dimethylcyclopropyl]pyridine-3-sulfonamide;
6-[(1S,3S)-3-(3-tert-Butyl-1,2,4-oxadiazol-5-yl)-2,2-dimethylcyclopropyl]pyridine-3-sulfonamide;
6-[(1S,3S)-2,2-Dimethyl-3-(3-phenyl-1,2,4-oxadiazol-5-yl)cyclopropyl]pyridine-3-sulfonamide;
6-{(1S,3S)-3-[3-(5-Fluoropyridin-3-yl)-1,2,4-oxadiazol-5-yl]-2,2-dimethylcyclopropyl}pyridine-3-sulfonamide;
6-{(1S,3S)-3-[3-(3,3-Difluorocyclobutyl)-1,2,4-oxadiazol-5-yl]-2,2-dimethylcyclopropyl}pyridine-3-sulfonamide;
6-[(1S,3S)-3-(3-Cyclobutyl-1,2,4-oxadiazol-5-yl)-2,2-dimethylcyclopropyl]pyridine-3-sulfonamide;
6-{(1S,3S)-2,2-Dimethyl-3-[3-(propan-2-yl)-1,2,4-oxadiazol-5-yl]cyclopropyl}pyridine-3-sulfonamide;
6-[trans-3-(1,3-Benzoxazol-2-yl)-2,2-dimethylcyclopropyl]pyridine-3-sulfonamide;
6-[trans-2,2-Dimethyl-3-(3-phenyl-1,2,4-oxadiazol-5-yl)cyclopropyl]pyridine-3-sulfonamide;
6-{trans-2,2-Dimethyl-3-[3-(propan-2-yl)-1,2,4-oxadiazol-5-yl]cyclopropyl}pyridine-3-sulfonamide;
6-[trans-3-(3-Cyclobutyl-1,2,4-oxadiazol-5-yl)-2,2-dimethylcyclopropyl]pyridine-3-sulfonamide;
6-{trans-3-[3-(3,3-Difluorocyclobutyl)-1,2,4-oxadiazol-5-yl]-2,2-dimethylcyclopropyl}pyridine-3-sulfonamide;
6-[trans-2-(3-Phenyl-1,2,4-oxadiazol-5-yl)cyclopropyl]pyridine-3-sulfonamide; and
6-[trans-2-(3-Cyclopentyl-1,2,4-oxadiazol-5-yl)cyclopropyl]pyridine-3-sulfonamide.
or a pharmaceutically acceptable salt thereof.

11. A pharmaceutical composition comprising (i) a pharmaceutically acceptable carrier and (ii) a compound of claim 1 or a pharmaceutically acceptable salt thereof.

12. The pharmaceutical composition of claim 11, further comprising a second therapeutic agent selected from the group consisting of acetylcholinesterase inhibitors; NMDA receptor antagonists; antipsychotics; MAO-B inhibitors; and levodopa.

13. A compound of claim 1, or a pharmaceutically acceptable salt thereof, for use in therapy.

* * * * *